(12) United States Patent
Yates et al.

(10) Patent No.: US 11,959,923 B2
(45) Date of Patent: Apr. 16, 2024

(54) FLUIDIC SEPARATION AND DETECTION

(71) Applicant: Cambridge Enterprise Limited, Cambridge (GB)

(72) Inventors: Emma Yates, Cambridgeshire (GB); Christopher Dobson, Cambridgeshire (GB); Therese Herling, Cambridgeshire (GB); Tuomas Pertti Jonathan Knowles, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 524 days.

(21) Appl. No.: 17/314,254

(22) Filed: May 7, 2021

(65) Prior Publication Data
US 2021/0318330 A1 Oct. 14, 2021

Related U.S. Application Data

(63) Continuation of application No. 16/377,837, filed on Apr. 8, 2019, now Pat. No. 11,029,315, which is a
(Continued)

(30) Foreign Application Priority Data
Nov. 14, 2013 (GB) .................................... 1320146

(51) Int. Cl.
*G01N 33/68* (2006.01)
*B01L 3/00* (2006.01)
(Continued)

(52) U.S. Cl.
CPC .... *G01N 33/6845* (2013.01); *B01L 3/502753* (2013.01); *G01N 15/0266* (2013.01);
(Continued)

(58) Field of Classification Search
CPC ..... B01L 2200/0631; B01L 2200/0636; B01L 2300/0816; B01L 2300/0861;
(Continued)

(56) References Cited

U.S. PATENT DOCUMENTS 5,716,852 A 2/1998 Yager et al.
5,932,100 A 8/1999 Yager et al.
(Continued)

FOREIGN PATENT DOCUMENTS

WO WO 03/066191 A1 8/2003
WO WO 2010/004236 A1 1/2010
(Continued)

OTHER PUBLICATIONS

International Search Report for PCT/GB2014/053385, Completed by the European Patent Office on Feb. 9, 2015, 4 Pages.
(Continued)

*Primary Examiner* — Jennifer Wecker
(74) *Attorney, Agent, or Firm* — Wolf, Greenfield & Sacks, P.C.

(57) ABSTRACT

Flow apparatuses comprising a separation channel, a downstream flow separator, a detection zone, an observation zone, and a waste channel. The separation channel has first and second flows in contact and allows lateral movement of components between contacting first and second flows. The downstream flow separator is in communication with the separation channel and diverts a part of the first fluid flow, the second fluid flow, or both, from the separation channel. The detection zone comprises a detection channel downstream of and in communication with the flow separator and configured to receive a plurality of diverted flows from the flow separator and a label channel configured to label the diverted flows from the flow separator. The observation zone is configured to record an analytical signal indicative of the
(Continued)

quantity and the electrical properties of the component. The waste channel is at the downstream end of the observation zone.

19 Claims, 30 Drawing Sheets

Related U.S. Application Data continuation of application No. 15/922,082, filed on Mar. 15, 2018, now Pat. No. 10,295,545, which is a continuation of application No. 15/036,455, filed as application No. PCT/GB2014/053385 on Nov. 14, 2014, now Pat. No. 9,952,222.

(51) Int. Cl.
| | | |
|---|---|---|
| G01N 15/02 | (2006.01) | |
| G01N 27/447 | (2006.01) | |
| G01N 33/50 | (2006.01) | |
| G01N 33/52 | (2006.01) | |
| G01N 15/00 | (2006.01) | |

(52) U.S. Cl.
CPC .......... *G01N 27/447* (2013.01); *G01N 33/50* (2013.01); *G01N 33/52* (2013.01); *B01L 2200/0631* (2013.01); *B01L 2200/0636* (2013.01); *B01L 2300/0816* (2013.01); *B01L 2300/0861* (2013.01); *B01L 2300/0867* (2013.01); *B01L 2300/087* (2013.01); *B01L 2300/0883* (2013.01); *B01L 2400/0421* (2013.01); *G01N 2015/0038* (2013.01); *G01N 2015/0288* (2013.01)

(58) Field of Classification Search
CPC ....... B01L 2300/0867; B01L 2300/087; B01L 2300/0883; B01L 2400/0421; B01L 3/502753; G01N 15/0266; G01N 2015/0038; G01N 2015/0288; G01N 27/447; G01N 33/50; G01N 33/52; G01N 33/6845
See application file for complete search history.

(56) References Cited

U.S. PATENT DOCUMENTS

| | | | |
|---|---|---|---|
| 5,948,684 | A | 9/1999 | Weigl et al. |
| 5,972,710 | A | 10/1999 | Weigl et al. |
| 6,033,546 | A | 3/2000 | Ramsey |
| 6,171,865 | B1 | 1/2001 | Weigl et al. |
| 6,368,871 | B1 | 4/2002 | Christel et al. |
| 6,454,945 | B1 | 9/2002 | Weigl et al. |
| 6,468,761 | B2 | 10/2002 | Yang et al. |
| 6,541,213 | B1 | 4/2003 | Weigl et al. |
| 6,582,963 | B1 | 6/2003 | Weigl et al. |
| 7,011,791 | B2 | 3/2006 | Weigl et al. |
| 7,271,007 | B2 | 9/2007 | Weigl et al. |
| 7,276,170 | B2 * | 10/2007 | Oakey ............... B01L 3/502715 204/554 |
| 7,666,660 | B2 | 2/2010 | Krylov et al. |
| 7,807,454 | B2 | 10/2010 | Oh |
| 9,409,173 | B2 | 8/2016 | Estes et al. |
| 9,952,222 | B2 | 4/2018 | Yates et al. |
| 9,958,369 | B2 | 5/2018 | Cohen et al. |
| 10,010,882 | B2 | 7/2018 | Hobbs et al. |
| 10,295,545 | B2 | 5/2019 | Yates et al. |
| 10,386,332 | B2 | 8/2019 | Herling et al. |
| 10,620,102 | B2 | 4/2020 | Mueller et al. |
| 10,670,504 | B2 | 6/2020 | Cohen et al. |
| 11,029,315 | B2 | 6/2021 | Yates et al. |
| 11,033,905 | B2 | 6/2021 | Douglas et al. |
| 2001/0026929 | A1 | 10/2001 | Yang |
| 2002/0186263 | A1 | 12/2002 | O'Connor et al. |
| 2006/0252054 | A1 | 11/2006 | Lin |
| 2006/0263903 | A1 | 11/2006 | Chien |
| 2007/0160474 | A1 | 7/2007 | Iida |
| 2008/0302732 | A1 | 12/2008 | Soh |
| 2009/0014360 | A1 | 1/2009 | Toner |
| 2009/0155927 | A1 | 6/2009 | Higashino |
| 2010/0032349 | A1 | 2/2010 | Shinoda |
| 2011/0020459 | A1* | 1/2011 | Achrol ............... B01L 3/502753 435/287.1 |
| 2011/0264380 | A1 | 10/2011 | Cottet et al. |
| 2012/0135507 | A1 | 5/2012 | Kim et al. |
| 2012/0174650 | A1 | 7/2012 | Ariessohn |
| 2016/0008811 | A1 | 1/2016 | Laser |
| 2017/0052147 | A1 | 2/2017 | Herling et al. |
| 2019/0201903 | A1 | 7/2019 | Douglas et al. |
| 2019/0234530 | A1 | 8/2019 | Douglas et al. |
| 2019/0247853 | A1 | 8/2019 | Douglas et al. |
| 2019/0247855 | A1 | 8/2019 | Douglas et al. |
| 2019/0331692 | A1 | 10/2019 | Yates et al. |
| 2019/0344267 | A1 | 11/2019 | Knowles et al. |
| 2020/0254448 | A1 | 8/2020 | Douglas et al. |
| 2020/0254455 | A1 | 8/2020 | Zhang et al. |
| 2020/0298236 | A1 | 9/2020 | Knowles et al. |

FOREIGN PATENT DOCUMENTS

| | | | |
|---|---|---|---|
| WO | WO 2012/106663 | A1 | 8/2012 |
| WO | WO 2014/064438 | A1 | 5/2014 |
| WO | WO 2015/071681 | A1 | 5/2015 |
| WO | WO 2020/058715 | A1 | 3/2020 |
| WO | WO 2020/128518 | A1 | 6/2020 |

OTHER PUBLICATIONS

Ahmad Can. J. Biochem. Cell Biol. 1985, vol. 63, pp. 1058-1063, "Thermodynamic characterization of the partially denatured states of ribonuclease A in calcium chloride and lithium chloride1".

Almgren et al. Journal of Colloid and Interface Science 1998, vol. 202, pp. 222-231, "SDS Micelles at High Ionic Strength. A Light Scattering, Neutron Scattering, Fluorescence Quenching, and CryoTEM Investigation".

Alvarez-Coque et al. Analytical Biochemistry 1989, vol. 178, pp. 1-7, "Formation and Instability of o-Phthalaldehyde Derivatives of Amino-Acids".

Benson et al. PNAS USA Feb. 1975, vol. 72, No. 2, pp. 619-622, "o-Phthaladehyde Fluorogenic Detection of Primary Amines in the Picomole Range. Comparison with Flurescamine and Ninhydrin, amino-acid analysis peptide analysis".

Biancalana et al. Biochimica et Biophysica Acta Jul. 2010, vol. 1804, No. 7, pp. 1405-1412, "Molecular Mechanism of Thioflavin-T Binding to Amyloid Fibrils".

Brandts et al. Journal of the American Chemical Society Sep. 13, 1967, vol. 89, No. 19, pp. 4826-4838, "The Thermodynamics of Protein Denaturation. III. The Denaturation of Ribonuclease in Water and in Aqueous Urea and Aqueous Ethanol Mixtures".

Brody et al. Sensors and Actuators A 1997, vol. 58, pp. 13-18, "Diffusion-based extraction in a microfabricated device".

Cheng et al. Lab Chip 2011, vol. 11, pp. 2316-2318, "Biocompatible multi-address 3D cell assembly in microfluidic devices using spatially programmable gel formation".

Cohen et al. Journal of Molecular Biology 2012, vol. 421, pp. 160-171, "From Macroscopic Measurements to Microscopic Mechanisms of Protein Aggregation".

Flockhart, Journal of Colloid Science 1957, vol. 12, pp. 557-565, "The Critical Micelle Concentration of Sodium Dodecyl Sulfate in Ethanol-Water Mixtures".

Ge et al. Journal of Biomaterials Science, Polymer Edition 1998, vol. 9, No. 2, pp. 131-150, "Bovine serum albumin adsorption onto immobilized organotrichlorosilane surface Influence of the phase separation on protein adsorption patterns".

Hatch et al. Nature Biotechnology May 2001, vol. 19, pp. 461-465, "A rapid diffusion immunoassay in a T-sensor".

(56) References Cited

OTHER PUBLICATIONS

Hellstrand et al. ACS Chemical Neuroscience 2010, vol. 1, pp. 13-18, "Amyloid B-Protein Aggregation Produces Highly Reproducible Kinetic Data and Occurs by a Two-Phase Process".
Herling et al. Applied Physics Letters 2013, vol. 102, pp. 184102-184102-4, "Integration and characterization of solid wall electrodes in microfluidic devices fabricated in a single photolithography step".
Hirota et al. Protein Science 1997, vol. 6, pp. 416-421, "Cooperative a-helix formation of b-lactoglobulic and melittin induced by hexafluoroisopropanol".
Ivanova et al. PNAS Nov. 10, 2009, vol. 106, No. 45, pp. 18990-18995, "Molecular basis for insulin fibril assembly".
Jacobs et al. Analytical Biochemistry 1986, vol. 156, pp. 334-340, "Stability of o-Phthalaldehyde-Derived Isoindoles".
Jacobson et al. Anal. Chem. 1994, vol. 66, pp. 3472-3476, "Microchip Capillary Electrophoresis with an Integrated Postcolumn Reactor".
Jacobson et al. Anal. Chem. 1994, vol. 66, pp. 4127-4132, "Precolumn Reactions with Electrophoretic Analysis Integrated on a Microchip".
Jimenez et al. PNAS Jul. 9, 2002, vol. 99, No. 14, pp. 9196-9201, "The protofilament structure of insulin amyloid fibrils".
Kamholz et al. Biophysical Journal Apr. 2001, vol. 80, pp. 1967-1972, "Optical Measurement of Transverse Molecular Diffusion in a Microchannel".
Kang et al. Lab Chip 2008, vol. 8, pp. 176-178, "Analysis of pressure-driven air bubble elimination in a microfluidic device".
Kim et al. Biochip Journal Mar. 2008, vol. 2, No. 1, 11 Pages, "Soft Lithography for Microfluidics a Review".
Knowles et al. Science Dec. 11, 2009, vol. 326, pp. 1533-1537, "An Analytical Solution to the Kinetics of Breakable Filament Assembly".
Kohlheyer et al. Lab Chip 2006, vol. 6, pp. 374-380, "Free-flow zone electrophoresis and isoelectric focusing using a microfabricated glass device with ion permeable membranes".
Lauga et al. Chapter 15 in Handbook of Experimental Fluid Dynamics Sep. 28, 2005, 27 Pages, "Microfluidics the No-Slip Boundary Condition".
Lee et al. Lab Chip 2009, vol. 9, pp. 479-482, "Effective mixing in a microfluidic chip using magnetic particles".
Levine, Protein Science 1993, vol. 2, pp. 404-410, "Thioflavine T interaction with synthetic Alzheimer's disease b-amyloid peptides: Detection of amyloid aggregation in solution".
Liu et al. Anal. Chem. 2000, vol. 72, pp. 4608-4613, "Electrophoretic Separation of Proteins on a Microchip with Noncovalent, Postcolumn Labeling".
Mok et al. Methods 2011, vol. 54, pp. 67-75, "Sedimentation velocity analysis of amyloid oligomers and fibrils using fluorescence detection".
Monahan et al. Anal. Chem. 2001, vol. 73, pp. 3193-3197, "A Method for Filling Complex Polymeric Microfluidic Devices and Arrays".
Nakamura et al. Analytical Letters 1982, vol. 15, No. A17, pp. 1393-1410, "On the Stability of Isoindole-Type Fluorophores Derived from O-Phthalaldehyde, Primary Amino Compounds and Thiols".
Nettleton et al. Biophysical Journal Aug. 2000, vol. 79, pp. 1053-1065, "Characterization of the Oligomeric States of Insulin in Self-Assembly and Amyloid Fibril Formation by Mass Spectrometry".
Oguri et al. Journal of Chromatography A 1997, vol. 787, pp. 253-260, "Determination of amino acids by high-performance capillary electrophoresis with on-line mode in-capillary derivatization".
Otzen, Biochimica et Biophysica Acta 2011, vol. 1814, pp. 562-591, "Protein-surfactant interactions a tale of many states".
Otzen, Biophysical Journal Oct. 2002, vol. 83, pp. 2219-2230, "Protein Unfolding in Detergents Effect of Micelle Structure, Ionic Strength, pH, and Temperature".
Powers et al. Biopolymers 1993, vol. 33, pp. 927-932, "Enhanced Solubility of Proteins and Peptides in Nonpolar Solvents Through Hydrophobic Ion Pairing".
Rida et al. Anal. Chem. 2004, vol. 76, pp. 6239-6246, "Manipulation of Self-Assembled Structures of Magnetic Beads for Microfluidic Mixing and Assaying".
Roth et al., Journal of Chromatography 1973, vol. 83, pp. 353-356, "Column Chromatography of Amino Acids with Fluorescence Detection".
Roth, Analytical Chemistry Jun. 1971, vol. 43, No. 7, pp. 880-882, "Fluorescence Reaction for Amino Acids".
Saito et al. Anal. Chem. 1994, vol. 66, pp. 134-138, "Kinetic Study of the Stability of the o-Phthalaldehyde-Spermine Fluorophore Formed by On-Column Derivatization".
Schuck, Analytical Biochemistry 2003, vol. 320, pp. 104-124, "On the analysis of protein self-association by sedimentation velocity analytical ultracentrifugation".
Shi et al. J. Sep. Sci. 2008, vol. 31, pp. 1144-1150, "Analysis of amino acids in human vascular endothelial ECV-304 cells by microchip electrophoresis with fluorescence detection".
Song et al. 9th International Conference on Miniaturized Systems for Chemical and Life Sciences Oct. 9-13, 2005, XP040568368, pp. 1025-1027, "Continuous PI-Based Sorting of Proteins and Peptides in a Microfluidic Chip using Diffusion Potential".
Song et al. Anal. Chem. 2006, vol. 78, pp. 3528-3536, "Continuous-Flow pl-Based Sorting of Proteins and Peptides in a Microfluidic Chip Using Diffusion Potential".
Squires, Reviews of Modern Physics Jul. 2005, vol. 77, pp. 977-1026, "Microfluidics Fluid physics at the nanoliter scale".
Sternson et al. Analytical Biochemistry 1985, vol. 144, pp. 233-246, "Rational Design and Evaluation of Improved o-Phthalaldehyde-like Fluorogenic Reagents".
Stone et al. Annu. Rev. Fluid Mech. 2004, vol. 36, pp. 381-411, "Engineering Flows in Small Devices Microfluidics Toward a Lab-on-a-Chip".
Takahashi et al. Electrochemistry Communications 2003, vol. 5, pp. 175-177, "A valveless switch for microparticle sorting with laminar flow streams and electrophoresis perpendicular to the direction of fluid stream".
Tan et al. Biomicrofluidics 2010, vol. 4, 9 Pages, "Oxygen plasma treatment for reducing hydrophobicity of a sealed polydimethylsiloxane microchannel".
Turgeon et al. Anal Bioanal Chem 2009, vol. 394, pp. 187-198, "Micro free-flow electrophoresis theory and applications".
Walsh et al. FEBS Journal 2009, vol. 276, pp. 1266-1281, "A facile method for expression and purification of the Alzheimers disease-associated amyloid b-peptide".
Waugh, J. Am. Chem. Soc. 1946, vol. 68, pp. 247-250, "A Fibrous Modification of Insulin. I. The Heat Precipitate of Insulin".
Wetter et al. Journal of Biological Chemistry 1951, vol. 192, pp. 237-242, "Immunological Studies on Egg White Proteins IV. Immunochemical and Physical Studies of Lysozyme".
Whitesides, Nature Jul. 27, 2006, vol. 442, pp. 368-373, "The origins and the future of microfluidics".
Whittingham et al. Journal of Molecular Biology 2002, vol. 318, pp. 479-490, "Insulin at pH 2: Structural Analysis of the Conditions Promoting Insulin Fibre Formation".
Wong et al. J. Am. Chem. Soc. 1985, vol. 107, pp. 6421-6422, "Reaction of o-Phthalaldehyde with Alanine and Thiols: Kinetics and Mechanism".
Yoshimura et al. Anal. Biochem. 1987, vol. 164, pp. 132-137, "Kinetic Analysis of the Fluorescence Reaction of Histamine with Orthophthalaldehyde".
Zawieja et al. Analytical Biochemistry 1984, vol. 142, pp. 182-188, "Analysis of Picogram Quantities of Protein in Subnanoliter-Size Samples".
PCT/GB2014/053385, Feb. 9, 2015, International Search Report and Written Opinion.

* cited by examiner

FIG. 15A
FIG. 15B
FIG. 15C
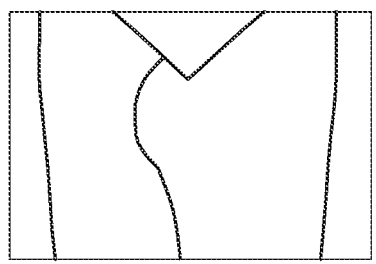
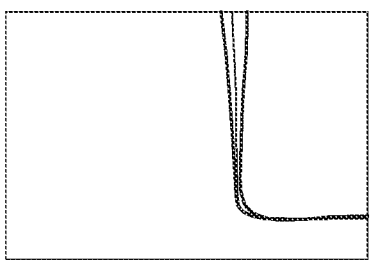
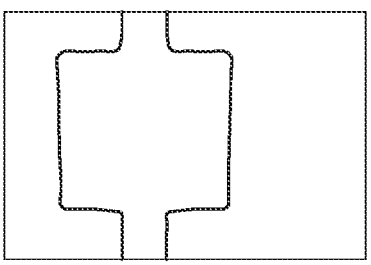
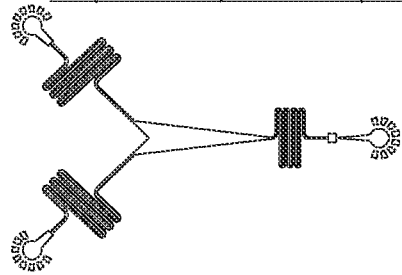
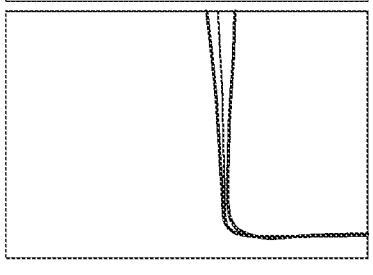
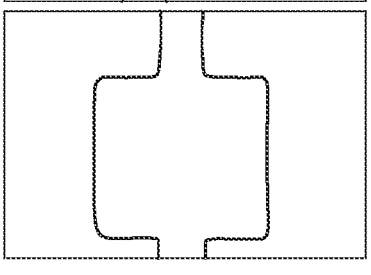
FIG. 15D
FIG. 15E
FIG. 15F
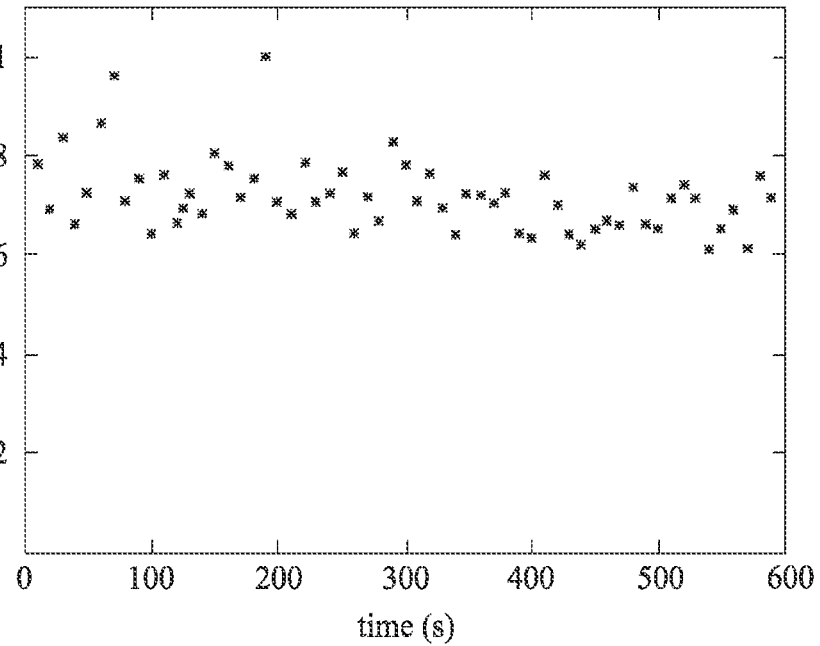
FIG. 15G

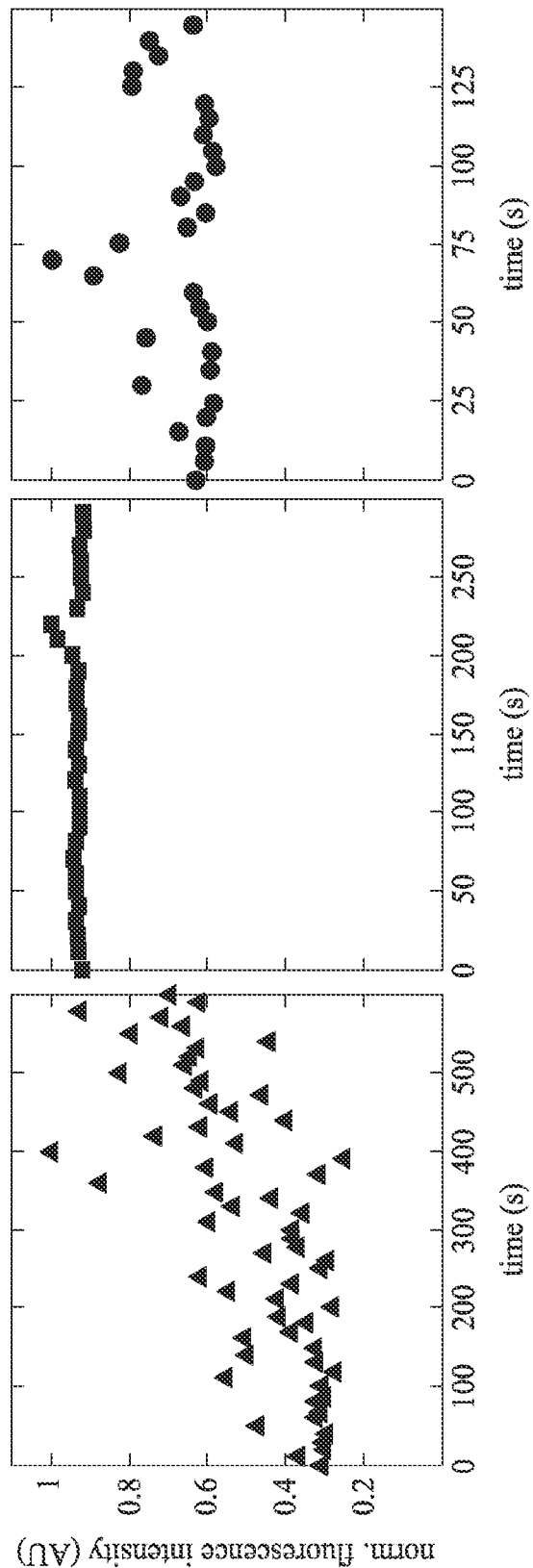

FLUIDIC SEPARATION AND DETECTION

RELATED APPLICATION

This application is a continuation of U.S. application Ser. No. 16/377,837, filed on Apr. 8, 2019, which is a continuation of U.S. application Ser. No. 15/922,082, filed on Mar. 15, 2018, which is a continuation of U.S. application Ser. No. 15/036,455, filed on May 13, 2016, which is a national phase application of PCT App. No. PCT/GB2014/053385 filed on Nov. 14, 2014, which claims the benefit and priority of GB App. No. 1320146.2, filed on Nov. 14, 2013, the contents of each of which are hereby incorporated by reference in their entirety.

FIELD OF THE INVENTION

The present invention relates to flow methods, such as flow diffusion methods, and flow apparatus for analysing component mixtures, such as mixtures of polypeptides.

BACKGROUND

The study of protein-protein interactions is an area of considerable interest. However, protein interactions are typically perturbed by traditional measurement and detection schemes. Existing methods for examining protein-protein interactions include FRET, NMR, EPR, SPR, ESI-MS, size exclusion chromatography, and native PAGE. Each of these methods requires that either one of the interacting partners is modified in some way, such as through the installation of a fluorescent label or immobilization on a surface, or that the entire complex is sieved through a matrix. These steps disrupt the transient interactions under observation, with the risk that some of the agglomerated species may be destroyed in the process of separation and labelling.

The separation and detection of components within fluid flows, such as microfluidic flows, presents a number of challenges. Given the recent increased interest in fluidic techniques for the reaction, separation and detection of components, there is interest in developing methods and devices that allow components to be separated and analysed in a continuous flow system.

The present inventors have recently described improved methods for distributing a component, including a component in a multicomponent mixture, across laminar flows in a fluidic device (see PCT/GB2013/052757). The distribution of components across the laminar flows is measured at multiple flow times by fluorescent spectroscopy. From these measurements it is possible to identify components of different size within the flows. The worked examples show the use of the methods described for the identification of Aβ(1-42) aggregation events, including the formation of oligomers and fibril clusters from the original monomeric species.

However, this work necessarily requires the use of components that are fluorescently active, or are provided with a fluorescent label. In the latter case, the behaviour of the component with the label may be affected by that label. The inventors' earlier work does not describe the purification of a component from the combined laminar flows, nor does it suggest how this might be achieved. Thus, although monomer and oligomer protein species are identified, they are not removed from the flow.

In-flow labelling and separation techniques are known in the art and have been well described by the Ramsey group (e.g. Liu et al. *Anal. Chem.* 2000, 72, 4608; Jacobson et al. *Anal. Chem.* 1994, 66, 4127; Jacobson et al. *Anal. Chem.* 1994, 66, 3472). For example, the group have described the electrophoretic separation of proteins on a flow device with covalent and noncovalent labelling (Liu et al.). Here, the group acknowledge the problem of labelling proteins prior to separation, particularly in electrophoretic separation experiments. Within a flow device, the group suggest downstream labelling of components after separation, rather than upstream labelling prior to separation. Electrophoretic techniques are used to draw components through the device. Here, the electrophoretic techniques separate components temporally based on their migration speed through a capillary. In this way, components having different charge-to-size ratios are distributed along the fluid flow. By way of example, the group show the separation of α-lactalbumin, β-lactoglobulin B and β-lactoglobulin A. The efficiency of the labelling techniques is not discussed and it is nowhere suggested that the components are quantitatively labelled.

The present inventors have now established an alternative fluidic method for separating components, for example proteins in the native state, and then subsequently analysing separated components under conditions that are optimised for detection.

SUMMARY OF THE INVENTION

The present invention provides a method of analysing a component using fluidic techniques. The method takes a distribution of the component across contacting fluid flows, such as laminar fluid flows, and separates a portion of that distribution for analysis. The distribution of the component is obtainable by diffusion or electrophoretic movement of the component from one fluid flow into a neighbouring fluid flow, such as laminar fluid flows. The distribution of the component permits the separation of the component from other components within the fluid flow. The analysis may include the step of labelling the component for ease of detection.

The method of the invention is a quantitative process that allows the steps of component separation and component analysis to be independently undertaken, and under conditions that are optimal for each. The separation step may be performed under native conditions to allow an understanding of the component and its environment, including its relationship with other components in a multicomponent mixture. The subsequent analysis may include denaturing and labelling steps to permit accurate identification and characterisation of separated component. It is therefore unnecessary to process and label a component prior to its separation.

The separation step allows a component of interest to be spatially separated from other components across a fluid flow. The separation of components is on the basis of the intrinsic properties of each component, including size or charge. Suitably separated component is collected in a flow diversion step, and the diverted flow is analysed under flow conditions, advantageously all on one fluidic substrate. The invention allows components to be separated under steady-state, permitting long exposure times for the efficient detection of low concentration samples.

The flow techniques of the invention may incorporate post-separation procedures for preparing a diverted component for analysis. Quantitative labelling procedures, such as the fluorescent labelling procedures described herein, allow the concentration of a component to be directly determined from the recorded analytical signal.

The methods and apparatus of the invention may be used to analyse components in a multicomponent mixture. Further, the methods and apparatus are suitable for analysing the association and dissociation of components within a mixture. The techniques described herein allow aggregation events between polypeptide components to be studied, including transient protein-protein interactions and the behaviour of non-obligatory protein complexes formed by proteins and multiple possible binders. Accordingly, the present invention provides an alternative strategy to analysing aggregation and dissociation events compared to traditional disruptive detection schemes. The analysis of association and dissociation events provides an opportunity to non-disruptively quantify relative binding kinetics.

By way of example, the present case shows that insulin aggregation events may be monitored over time. The method of the invention provides information about the depletion of monomer and small oligomers in an insulin aggregation reaction, where such information was not previously directly accessible. The method of the invention may also be used to probe aggregation events in response to a stimulus, such as pH change, as shown herein. The worked examples also show that diffusive methods may be used to study the dimerization of β-lactoglobulin.

The methods of the invention also allow the hydrodynamic radius of a component to be determined, including the hydrodynamic radii of component populations of a heterogeneous multicomponent mixture.

Accordingly, in a general aspect of the invention there is provided a method of analysing a component distributed across contacting first and second fluid flows, such as first and second laminar flows, the method comprising the step of diverting a part of the first fluid flow, a part of the second fluid flow, or parts of the first fluid flow and the second fluid flow, wherein the diverted part comprises the component; and analysing the component in the diverted part of the fluid flow.

In a first aspect of the invention there is provided a method for analysing a component, the method comprising the steps of:
(iii) providing a distribution of a component across contacting first and second fluid flows, such as laminar fluid flows;
(iv) diverting a part of the first fluid flow, a part of the second fluid flow, or parts of the first fluid flow and the second fluid flow, wherein the diverted part comprises the component;
(v) optionally labelling the component in the diverted part of the fluid flow; and
(vi) analysing the component in the diverted part of the fluid flow.

In one embodiment, the method comprises the preliminary steps of:
(i) providing the component in a first fluid flow;
(ii) contacting the fluid flow with a second fluid flow, such as to generate a laminar flow; and step (iii) is permitting the component to join the second fluid flow, thereby to obtain a distribution of the component across the first and second fluid flows.

In one embodiment, step (ii) comprises contacting the fluid flow with a plurality of second fluid flows, such as to generate a laminar flow of the second fluid flows on either side of the first fluid flow.

In one embodiment, step (iii) comprises the diffusion of the component into the second fluid flow or the electrophoretic movement of the component into the second fluid flow.

In one embodiment, step (iv) is diverting a part of the second fluid flow, wherein the diverted part comprises the component.

In one embodiment, step (v) is present. In one embodiment, step (v) is fluorescent labelling of the component.

In one embodiment, the component is or comprises a polypeptide, a polynucleotide or a polysaccharide.

In one embodiment, the component is a protein.

In one embodiment, the component is a component of a multicomponent mixture.

The present invention also provides a flow apparatus adapted for use in the method of the invention, including the method of the first aspect of the invention.

Thus, in a further aspect of the invention there is provided a flow apparatus for detecting a component in a mixture, the apparatus comprising a separation channel for first and second flows in contact, and the separation channel is in fluid communication with a downstream flow separator, and a detection zone which is downstream and in fluid communication with the flow separator, wherein the separation channel is adapted to permit lateral movement of components between contacting first and second flows and the flow separator is adapted to divert a part of the first fluid flow, a part of the second fluid flow, or parts of the first fluid flow and the second fluid flow, from the separation channel.

In a further aspect of the invention there is provided a method of labelling a component, the method comprising the steps of:
(iii) providing a distribution of a component across contacting first and second fluid flows, such as a laminar flow;
(iv) diverting at least part of the first fluid flow, at least part of the second fluid flow, or at least parts of the first fluid flow and the second fluid flow, wherein the diverted part comprises the component;
(v) labelling the component in the diverted part of the fluid flow; and optionally
(vi) analysing the component in the diverted part of the fluid flow.

In one embodiment, the method comprises the preliminary steps of:
(i) providing the component in a first fluid flow;
(ii) contacting the fluid flow with a second fluid flow, such as to generate a laminar flow;
and step (iii) is permitting the component to join the second fluid flow, thereby to obtain a distribution of the component across the first and second fluid flows.

In one embodiment, step (iv) is diverting at least part of the second fluid flow.

DESCRIPTION OF THE FIGURES

FIG. 1013 the hydrodynamic radii expected for the observed intensity ratio.

FIG. 15A-FIG. 15B includes brightfield images and fluorescence images FIG. 15E and FIG. 15F of channels within the microfluidic device shown schematically in FIG. 15D, having a treated PDMS channel surfaces;

FIG. 15A is the image of the junction at the upstream end of the convergent channel; FIG. 15B is the image of the downstream end of the convergent channel; FIG. 15C is the image of the downstream detection zone; FIG. 15E is the image of the downstream end of the convergent channel; FIG. 15F is the image of the downstream detection zone; and FIG. 15G shows the recorded normalised fluorescence intensity (AU) measure over time (s), showing that a stable flow is provided in the channel.

FIG. 21A-FIG. 21C shows the change in normalised fluorescence (AU) over time (s) for bovine insulin passed through its IEP in a fluidic device where FIG. 21A is a standard PDMS fluidic device according to an embodiment of the invention; FIG. 21B is a standard PDMS fluidic device that has been subjected to an additional plasma treatment; and FIG. 21C is a standard black PDMS fluidic device that has been subjected to an additional plasma treatment.

FIG. 22E shows the relationship between protein concentration (nM) and recorded fluorescence intensity (AU) for the BSA protein, showing that nM protein concentrations hold to the linear fit.

DETAILED DESCRIPTION OF THE INVENTION

Figure 1A:
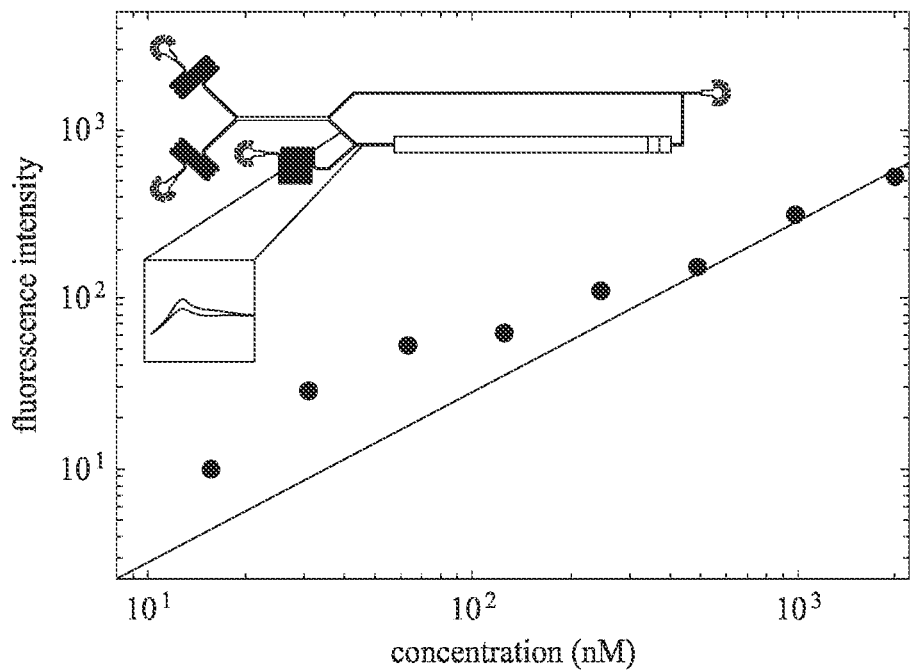
FIG. 1A shows the change in fluorescence intensity with the change in bovine serum albumin concentration as measured in a fluidic device (shown inset) according to an embodiment of the present invention. The BSA was labelled after diffusion across a fluid flow and flow separation. The formation of fluorescence intensity as the protein and labelling solutions contact one another is shown. Background-corrected fluorescence intensity was measured and plotted as a function of protein concentration. A detection limit of approximately 15 nM was observed.

The present invention provides methods and apparatus for analysing a component in a fluid, including a component in a multicomponent mixture. The method of the invention includes the step of diverting a part of a flow of contacting first and second fluids, and analysing the diverted flow. The diverted part of the flow is a portion of the lateral distribution of the component across the first and second fluid flows. The analysis step is performed advantageously in line with the diverting step and the separation step, where present.

Typically, the distribution of the component across first and second flows is obtainable by diffusive transport of the component from the first fluid flow into the second fluid flow. However, other techniques that allow the lateral movement of a component from a first fluid flow to a second fluid flow may be used. For example, electrophoretic techniques may be used to obtain a distribution of a component across the first and second fluid flows.

The present invention allows a component to be separated and diverted in its native state, for example together with other components that are also in their native states. Thus, the lateral distribution of a component or a plurality of components is representative of the diffusive or electrophoretic characteristics of those components in the native state. Where the component is part of a multicomponent mixture, the proportion of each component in the lateral distribution is representative of the relative proportions of those components in the native state.

The methods of the invention are also suitable for use in analysing components at very low concentrations. The methods of the invention make use of very small sample sizes also, which means that a component may be detected at attomol levels of sensitivity. The molecular size of components may be determined over a four order of magnitude concentration range, while tolerating heterogeneous mixtures of unlabelled species.

As described herein, the methods of the invention may be used to analyse aggregation events and dissociation events.

After diversion of a part of the lateral distribution, it is not necessary to retain a component in its native state. The subsequent analysis steps may be performed under conditions that are optimal for identification and quantification.

Microdevices for analysing components are known, however such devices are not adapted for the separation of one or more components across a channel. The present inventors have found that the development of a distribution of a component across a flow is a useful separation strategy that may be employed as a precursor step to the analysis of a component of interest. The combination of the separation and analysis steps on a microfluidic device provides an improved method for studying components, particular those components that are present within complex multicomponent mixtures.

General Methods

The method of the first aspect of the invention generally looks to analyse, such as characterise or quantify, a component in a solution.

A first fluid flow comprising one or more components is brought into contact with a second fluid flow in a separation channel, such as to generate a laminar flow. The contacted flows are permitted to flow along the separation channel and components in the first fluid flow are permitted to move into the second fluid flow, to provide a distribution of the components across the first and second fluid flows. A part of the first fluid flow, a part of the second fluid flow, or parts of the first and second fluid flows are diverted into a diversion channel and then permitted to flow into an analysis channel for analysis. The diverted flow in the diversion channel may be permitted to contact a reagent flow, provided from a reagent channel, prior to analysis. The reagent flow provides reagents for mixture, and optionally reaction, with a component, thereby to allow improved detection and characterisation of the component.

The separation channel, diversion channel and analysis channels and reagent channel, where present, are parts of a fluidic device. The fluidic device, particularly the analysis channel, is adapted for use with a detector for the components.

The flow rate of each flow is maintained at a substantially constant level during the separation, diversion and analysis steps. The separation, diversion and analysis steps may be undertaken only when a stable flow is established in the channels of each section.

The component may be or comprise a polypeptide, a polynucleotide or a polysaccharide. In one embodiment, the component is or comprises a polypeptide. In one embodiment, the component is or comprises a protein.

The component may be part of a multicomponent mixture. The separation step may therefore be used to at least partially separate the component from other components. For example, the techniques described herein allow for separation based on size or charge-to-size ratio, amongst others.

In one embodiment, the multicomponent mixture comprises agglomerations of components, including proteins, such as monomer, dimer and trimer species, or other higher order agglomerations. Thus, the techniques described herein may be used to separate and analyse protein-protein interactions. This is shown in the worked examples for the protein insulin.

Fluid Flows

The present invention provides methods of separation and analysis for a component provided in a fluid flow. In one embodiment, a reference to a fluid flow is a reference to a liquid flow.

A fluid flow may be an aqueous flow. An aqueous flow may include other solvents, such as DMSO, alkyl alcohol and the like.

The devices of the invention may be adapted for use with fluid flows, and may be adapted for use with aqueous fluid flows.

In embodiments of the invention, the component is initially provided in a first fluid flow. The component is preferably dissolved in the first fluid.

In one embodiment, the first fluid allows a component or components to remain in its native state. Where the component is a biomolecule, such as a protein, the fluid flow may be a suitable buffer. Thus, the salt content and pH, amongst others, may be selected to retain the component in its native state.

The second fluid flow may be identical to the first fluid flow, except that the second fluid flow does not contain the component.

The first and second fluid flows are brought into contact, and component in the first flow is permitted to move into the second flow to generate a distribution of the component across first and second fluid flows. The contacting flows may be a laminar flow of the first flow with the second flow.

In some embodiments, a labelling flow is brought into contact with a diverted flow. The labelling flow is typically a liquid flow, such as an aqueous flow, containing reagents suitable for labelling a component.

In some embodiments, a denaturing flow is brought into contact with a diverted flow. The denaturing flow is typically a liquid flow, such as an aqueous flow, containing reagents suitable for denaturing a component.

Separation

The method of the invention includes the step of providing a distribution of a component across the first and second fluid flows. The distribution is typically a non-uniform distribution of the component across the first and second fluid flows.

The method of the invention may include the preliminary step of distributing a component across the fluid flows. Thus, the component is provided in a first fluid flow, and the component is permitted to join the second fluid flow, thereby to provide a lateral distribution of the component across the first and second fluid flows. As described herein, the distribution may comprise the diffusion of the component into the second fluid flow or electrophoretic movement of the component into the second fluid flow.

Other Lateral distribution techniques may be used.

The distribution is the lateral distribution of the component or a multicomponent mixture comprising the component.

A lateral distribution may be contrasted with a distribution of components along the fluid flow. For example, it is known in the art that fluidic methods may be used to separate components in a fluid flow based on the Taylor dispersion of a species in a fluid channel. For example, US 2011/264380 describes methods for determining the hydrodynamic radius of a polydisperse species. The species to be analysed is mixed with a monodisperse standard. The resulting mixture is added to a carrier fluid flowing along a capillary tube and the Taylor profile of the mixture as it exits the capillary is recorded.

As noted previously, the Ramsey group have described electrophoretic methods for separating proteins, however, the proteins are separated along the fluid flow and there is no non-uniform distribution of the components across the flow. This may be regarded as a temporal rather than a spatial distribution. As noted previously, in contrast, the present invention allows components to be spatially separated under steady-state, permitting long exposure times for the efficient detection of low concentration samples.

The separation approaches described herein are largely insensitive to the nature of the solvent conditions used in the flows. Thus, it is possible to study biological molecules, such as proteins, under their native conditions. In this way the behaviour of a component in the separation step is a characteristic of that component in its native state. There is no need for the analysis to include a calibration step to convert the behaviour of a component under foreign conditions to an expected behaviour under natural conditions.

Where the component is a part of a mixture (a multicomponent mixture), the component and other components of the mixture may be disturbed across the channel, thereby to provide a distribution profile for all components across the first and second fluid flows.

The diverting step may be performed before the component has reached the boundary of the second fluid flow (i.e. the channel wall). Where the component is part of a multicomponent mixture, the diverting step may be performed before any component in the multicomponent mixture has reached the boundary of the second fluid flow.

The distribution profile is dependent upon the technique for distributing the component, and the time permitted for the distribution. Typically, the time permitted for distribution is such that components in the first fluid flow have not reached the boundary of the second fluid flow, as noted above. The flow residency time of the first and second flows in the separation channel may be selected such that components in the first fluid flow do not have time to reach the boundary under the separation conditions employed.

In one embodiment, the distribution of the component may be diffusion from the first flow to the second flow. The rate of diffusive transport is proportional to the diffusion coefficient D of the component and inversely proportional to the hydrodynamic radius $r_n$. Thus, smaller components are expected to diffuse across the second fluid flow at a greater rate than larger components. Accordingly, in the diversion step, the diversion of a part of the second fluid flow close to the boundary of the second fluid flow at the wall will collect those components having a smaller size. The diversion of a part of the second fluid flow close to the laminar boundary with the first fluid flow will allow collection of those components having a larger size. It follows that the diversion of a part of the second fluid flow that is between the laminar boundary and the channel boundary will allow collection of those components of intermediate size.

The size of the components diverted will depend upon the location of the flow separator in the separation channel. The range of components that are diverted will depend upon the relative size of the diverted part compared to the total width of the first or second fluid flow, and the part of the flow that is diverted.

The diversion step may collect a part of the first fluid flow. Using a diffusion separation technique, the smaller components in the first fluid flow are expected to deplete more rapidly than the larger components as the smaller components diffuse into the second fluid flow at a greater rate.

In one embodiment, the distribution of the component may be electrophoretic movement from the first flow to the second flow. The rate of electrophoretic transport is proportional to the charge-to-size ratio of the component. Thus, components having a large charge and/or a small size are expected to have a greater electrophoretic movement compared to those components having a smaller charge and/or size.

Where electrophoresis is used to separate components, the second fluid flow is typically provided at both sides of the first fluid flow. During electrophoresis negatively charged species may be deflected into one of the second fluid flows, whilst positively charged species are deflected into the other fluid flow.

Thus, components having a high charge-to-size ratio are expected to move (divert or deflect) across the second fluid flow at a greater rate than components having a low charge-to-size ratio. Accordingly, in the diversion step, the diversion of a part of the second fluid flow close to the boundary of the second fluid flow at the wall will collect those components having a high charge-to-size ratio. The diversion of a part of the second fluid flow close to the laminar boundary with the first fluid flow will allow collection of those components having a low charge-to-size ratio. It follows that the diversion of a part of the second fluid flow that is between the laminar boundary and the channel boundary will allow collection of those components of intermediate charge-to-size ratio.

The charge-to-size ratio of the components diverted will depend upon the location of the flow separator in across the separation channel. The range of components that are diverted will depend upon the relative size of the diverted part compared to the total width of the first or second fluid flow, and the part of the flow that is diverted. It will be appreciated that the diversion of a part of the second fluid flow may collect only those species that have a negative or positive charge.

The flow separator may also be placed to collect a part of one of the second fluid flows, thereby to collect either positively-charged or negatively-charged components.

Described above are diffusive and electrophoretic methods for distributing a component across first and second fluid flows. Alternative methods for the distribution of a component may be used. Examples include isoelectric point determination, ultracentrifugation, and magnetic separation, for example of metalloproteins.

The method of the invention comprises the step of diverting a part of the first or second flows, or diverting parts of the first and second fluid flows.

The diverting step does not include the step of diverting all of the first fluid flow or all of the second fluid flow.

US 2006/0263903 describes a flow apparatus suitable for measuring the diffusion of a component from one fluid flow to another fluid flow. The component is provided in a first fluid flow which is permitted to contact a second fluid flow at a cross-junction. The first and second fluid flows form a laminar flow, and component is permitted to diffuse from the first fluid flow to the second fluid flow. The contact time between the first and second fluid flows is generally short, and the first and second flows are subsequently separated. The second fluid flow is analysed to determine the quantity of component present.

In contrast to the methods described in US 2006/0263903, the present invention does not divert all of the second or first fluid flows. Instead, the method of the present invention diverts a part of the first fluid flow, a part of the second fluid flow, or parts of the first and second fluid flows.

The analysis of a part of a fluid flow allows the user to determine the quantity and identity of material in a portion of the diffusion profile. This information is not available to a user of the device of US 2006/0263903.

U.S. Pat. No. 6,468,761 discusses labelling of products before or after a separation step with a latent fluorophore. The use of a denaturating agent to enable the quantitative labelling of the component is not discussed.

Kamholz et al. describe a flow apparatus suitable for measuring the diffusion of a component from one fluid flow to another fluid flow. The device is common in the art and is also described in Brody et al. and Hatch et al. Such apparatus are used to bring together a component fluid flow and a blank fluid flow. The component and blank fluid flows form a laminar flow, and component is permitted to diffuse from the component fluid flow to the blank fluid flow. The component and blank fluid flows are not subsequently separated, and the diffusion of the component is measured (e.g. by fluorescence) across the whole of the blank fluid flow.

The separation step may be distinguished over chromatographic and Taylor separation methods, and the alternative electrophoretic techniques (capillary electrophoresis) of the Ramsey group, where components are separated along the fluid flow. Such techniques may be regarded as separating components in time. In contrast, the separation methods employed in the present case separate components in space.

In one embodiment, a component is permitted to partially diffuse across a fluid flow, for example from one flow to another flow.

In one embodiment, the first fluid flow is provided as a central flow between two laminar second fluid flows. Thus, a component in the first fluid flow may be distributed into one or both of the second fluid flows.

In one embodiment, the distribution of a component or components across the flows is measured. The distribution of a component or components may be measured at a plurality of locations along the fluid flow. The measurements are made before the laminar flow is diverted. Where diffusion distribution techniques are used, each location represents a particular diffusion time. Such measurements may be made only when the component has an inherent functionality that allows it to be detected. Where a component lacks such functionality, it may be provided with functionality in a later labelling step.

In the present invention the step described above is not necessary as information relating to the distribution of the component may be recorded from the diverted flow, as described herein.

Diversion

The method of the present invention includes the step of diverting a part of the first and/or second fluid flows. The diverted part of the fluid flow contains component, and the analysis of the component is undertaken in the diverted part of the fluid flow, which is separated from the remaining portion of the first and second fluid flows.

The diversion step takes a part of the first fluid flow, or a part of the second fluid flow, or parts of the first and second fluid flows. In one embodiment, the diversion step takes a part of the second fluid flow.

The diversion step does not take all of the first fluid flow or all of the second fluid flow. Where reference is made to the diversion of parts of the first and second fluid flows, this is a reference to the diversion of a part of the first fluid flow and a part of the second fluid flow. The diversion of this part of the laminar flow includes the boundary where the first fluid flow and the second fluid flow contact.

The diversion step separates a part of the fluid flow for subsequent analysis. The part of the fluid flow taken represents a portion of the lateral distribution profile established in the separation step. The diversion step is the separation of a fraction of the total width of the fluid flow, or a fraction of the width of the first or second fluid flow. The fraction of the fluid flow that is diverted is not particularly limited and is selected based on the component for analysis, and, where present, other components in a multicomponent mixture.

The diverting step refers to the separation of a portion of the flows that corresponds to a part of the first fluid flow and/or second fluid flow. When the first and second fluid flows first contact there is a clear distinction between first and second fluid flows. The former carries the components, and the latter carries no components. At the downstream end of the separation channel components from the first fluid flow move across into the second fluid flow to generate a distribution of components across the first and second fluid flows.

In the present case, a reference to the diversion of a fluid flow is a reference to a particular cross section portion of the contacting first and second fluid flows, such as a particular region in the channel. That region of the channel is said to be a part of the first fluid flow if it corresponds to a region in the channel at the upstream part of the channel, such as the junction, where the first fluid flow first contacts the second fluid flow.

For example, when the first and second flows first contact, a contacting flow may be established at the upstream part of the channel where the first fluid flow occupies half of the channel width and the second fluid flow occupies the remaining half of the channel width. A diverted part of the fluid flow may be referred to as a diverted part of the first fluid flow if that part is taken from the half of the channel width that was originally occupied by the first fluid flow. In this situation the demarcation between first and second fluid flows is simply the centre line in the channel.

The location of the first and second fluids at the downstream end of the contacting flows may be determined from the distribution of components held with a first fluid flow. For example, in a diffusive distribution, a very large component will have negligible diffusion into the second fluid flow. At the downstream end the very large component will be predominantly retained in the first fluid flow (see, for example, FIG. 8 which shows that there is a minimal diffusion of components having a large hydrodynamic radius into the second flow, in a separation step according to an embodiment of the invention). In an electrophoretic separation an uncharged component will have a negligible deflection in response to the applied filed, and therefore will not substantially move out of the first fluid flow.

In one embodiment, the diversion step diverts at least 5%, at least 10%, at least 15%, at least 20%, at least 25%, at least 30% of the first fluid flow, the second fluid flow or the first and second fluid flows.

In one embodiment, the diversion step diverts at most 40%, at most 50%, at most 60%, at most 75%, at most 85% of the first fluid flow, the second fluid flow or the first and second fluid flows.

In one embodiment, the diversion step diverts an amount of the first fluid flow, the second fluid flow or the first and second fluid flows from a range where the lower and upper values for the range are selected from the minimum and maximum values given above.

In one embodiment, the diversion step diverts a part of the second fluid flow.

In one embodiment, the part of the second fluid flow that is diverted may be the part that extends from the boundary of the second fluid flow with the first fluid flow across at most 5%, 10%, 15%, 25%, 50 or 75% of the width of the second fluid flow.

In one embodiment, the part of the second fluid flow that is diverted may be the part that extends from the boundary of the second fluid flow with the channel wall, across at most 5%, 10%, 15%, 25%, 50% or 75% of the width of the second fluid flow.

In one embodiment, the part second fluid flow that is diverted does not include the part that extends from the boundary of the second fluid flow with the first fluid flow or the part that extends from the boundary of the second fluid flow with the channel wall. Thus, the diverted part is an intermediate part of the second fluid flow. This intermediate part may be at most 5%, 10%, 15%, 25%, 50% or 75% of the width of the second fluid flow.

The part of the fluid flow that is directed will depend upon the identity of the component to be detected and the nature of the separation step.

As noted in the separation section above, diffusion and electrophoretic separation techniques may be used to obtain a distribution of a component or components across the first and second fluid flows. The part of the fluid flow that is diverted may be chosen in order to analyse components having a property of interest, e.g. a particular size or a particular charge-to-size ratio.

The methods of the invention may be used to collect components that differ in the property of interest. The part of the first or second fluid flow that is collected may be changed in order to divert alternative components. The separation techniques may also be adapted to alter the distribution of components at point where the flows are diverted. For example, the diffusion time in a diffusion separation may be altered with changes in flow rate, or changes in the length of the separation channel (as described in PCT/GB2013/052757). The deflection of components in an electrophoretic separation may be altered with changes in flow rate or changes in the applied field (for example as described by Herling et al.)

It is not necessary to separate the combined flows as a fraction of the flow height (or depth). In the device of the invention, the fluid flows may be separated by appropriate placement of exit channels at the downstream end of the separation channel. A diversion channel may be located at an appropriate lateral location, to divert fluid from the required part of the first or second fluid flow (or flows) from the separation channel.

The remaining parts of the laminar flow that are not diverted may be collected, or those parts may be analysed, as described in further detail below.

A portion of the fluid flow in the separation channel is permitted to flow into a diversion channel. The fluid in the diversion channel is in fluid communication with a detection zone, such as a detection channel of the detection zone, where component delivered into the diversion channel from the separation channel may be analysed.

In one embodiment of the invention a plurality of fluid flow parts is diverted. At least one diverted part of the laminar fluid flow is analysed. Where a diverted part of the laminar flow includes a part of the second fluid flow, that diverted part is analysed.

Each diverted flow is a part of the first fluid flow, a part of the second fluid flow, or parts of the first fluid flow and the second fluid flow. One of the diverted parts comprises a component. Where the first fluid flow comprises a plurality of components, each of the plurality of fluid flow parts may contain a component.

The diverted flow is subsequently analysed downstream as described below.

In one embodiment of the invention, a diverted part of the first and second flows is recombined with other parts of the flow after analysis. Thus, all components in the original first and second fluid flows may be collected for further analysis and use.

Fluidic devices for the diversion of flow streams are known in the art, but these devices are not adapted for use in diverting a part of a flow containing a distribution of a component across that flow.

For example, US 2002/0186263 describes a microfluidic device having multiple fraction collectors arranged in series along a flow channel. The device is designed so that each fraction collector (which is simply a valve) is capable of directing all of the flow in a channel into a side channel. There is no suggestion that a part of the fluid flow is diverted. Also, there is no mention of a distribution of a component, such as a non-uniform distribution of the component, across a channel and there is no mention of diffusive or electrophoretic techniques.

US 2010/0032349 describes a fluidic device for generating droplets from a fluid flow. There is no mention of diffusive or electrophoretic separation. Although the document describes the separation of the formed droplets at a downstream end of the device, the separation occurs along the direction of the fluid flow, and not across the fluid flow, as required by the methods of the present case. US 2010/0032349 does not refer to laminar fluid flows or component distribution across fluids, and there is no clear description of a step where a part of a fluid flow is diverted from another.

US 2012/135507 is concerned primarily with the nature of a substrate used in a flow apparatus and the use of the flow apparatus to selectively capture bacteria using magnetic beads. The document does not describe diffusive or electrophoretic separation, and there is no indication that there is a non-uniform distribution of components across a laminar flow. Indeed, US 2012/0135507 does not appear to disclose the use of laminar flowing fluids. Where the document refers to separation, this appears to mean only that the magnetic beads are drawn apart in the fluid flow, and there is no discussion about what proportions of the fluid flow are diverted.

WO 2010/004236 describes a material separation flow device. The flow device includes a flow barrier, which prevents material from entering a branch channel from a main channel. Thus, a flow is provided having a component within it. The flow is permitted to move along a channel and the channel has a branch. The branch may take part of the flow, for example containing a component of interest, to an analytical device.

WO 2010/004236 explains that it is sometimes helpful to prevent a component from entering the branch. In order to do this a barrier flow is provided at the side of the main flow, and across the branch in order to prevent a component in the main flow from entering into the branch. Thus, where a second flow is provided it is intended to prevent a component from crossing into the branch. Components of interest may only be drawn into the branch when induced to do so, for example when a voltage is applied at the branch side to electrokinetically direct the flow of the component downstream.

WO 2010/004236 is for use in the collection of components that have been separated along the length of a flow channel. WO 2010/004236 does not describe the separation and collection of components across the channel.

As mentioned previously, US 2006/0263903 describes the step of generating a laminar fluid flow at a cross point, and the subsequent separation of that laminar flow. The laminar flow is generated from a component-containing flow and a blank flow. At the cross point component is permitted to diffuse into the blank flow. The separation involves the diversion of all of the blank flow (which now contains some small amount of component) from the remaining component-containing flow. US 2006/0263903 does not describe the step of diverting a part (only) of the component flow or the blank flow. US 2006/0263903 is apparently only suitable for use with a single component, and there is no suggestion that it could or would be suitable for separating multicomponent mixtures.

Analysis

In step (v) of the method of the invention, the diverted part of the fluid flow, comprising a component, is analysed.

The analysis step may include the preliminary step of preparing the diverted part of the fluid flow, including preparing the component, for analysis.

In some embodiments, the method of the invention includes the step of permitting the component to join the second fluid, wherein the component is in a native state. In this form the component may not be suitable for analysis. Thus, the method of the invention may include the step of preparing the component for analysis, which may include or involve the denaturing of the component.

Advantageously, the distribution of a component or components may occur under native conditions, and the subsequent analysis steps may be undertaken under alternative conditions for optimal characterisation of the components.

Typically, the component is analysed by spectroscopy including UV/vis and fluorescent spectroscopy, and preferably by fluorescent spectroscopy. Fluorescent spectroscopy is particularly attractive as it affords high signal to noise ratios.

In one embodiment, the diverted flow is contacted with a reagent flow, and one or more reagents within the reagent flow are permitted to mix, optionally to react, with a component in the diverted flow. After appropriate mixing and reaction, an analysis is performed. The component may be analysed within the fluid flow. The reagent may be a label or may generate a detectable label upon reaction.

In one embodiment of the invention the component is labelled after separation, for example after diversion. The labelling process is a part of the detection step for the analysis of the component.

The addition of the label may be necessary to detect the separated component. For example, the component may not possess suitable or sufficient functionality to allow its detection by spectroscopy. For example, where a component has no or few chromophore groups, it may be beneficial to label the component with one or more chromophores prior to analysis.

In one embodiment, the component is provided with one or more chromophore labels, such as fluorophore labels, after separation.

In one embodiment, the label is a latent label. A latent label is a label that is spectroscopically active, such as fluorescently active, only when it is associated with the component. Otherwise, the label is spectroscopically inactive. Thus a latent label is detectable only when it is associated with the component, and label that has not formed an association with the component remains spectroscopically inactive. It follows that the detection of the component is simplified, as it is not necessary to remove unreacted label from the fluid flow, or to discount the contribution of the label to the recorded spectroscopic signal.

For example, and as described herein, a reaction with a component may remove a group present on the label that quenches its fluorescence, the reaction thereby removing the quench. In another example, the label, such as a fluorophore group, is formed during the labelling reaction, for example through the formation of an extended conjugated system.

In one embodiment, the label is covalently bonded to the component. Thus, the labelling step includes the formation of one or more covalent bonds between the label and the component. The covalent bond may be formed with an amino, hydroxy or thiol group on the component. Where the component is a polypeptide, such as a protein, the covalent bond may be formed with the amino acid residue side chain functionality.

In other embodiment, non-covalent labels may be used, which may be specific or nonspecific to the component. Examples of non-covalent labels for components are described by the Ramsey group (see, for example, Liu et al. *Anal. Chem.* 2000, 72, 4068).

In one embodiment, the label reacts with amino functionality of the component, such as primary amino functionality (—NH$_2$). Where the component is or comprises a polypeptide, such as a protein, the label may react with lysine residues of the polypeptide. Labels for reaction with hydroxyl (—OH), carboxyl (—COOH) and thiol (—SH) functionality may also be used. Where the component is or comprises a polypeptide, such as a protein, the label may react with serine or threonine, aspartic acid or glutamic acid, or cysteine residue of the polypeptide, for example.

In one embodiment, the label is derived from ortho-phthalaldehyde or an ortho-phthalaldehyde-containing compound. Such are particularly useful for labelling amino functionality, and are especially useful for labelling polypeptides, as described herein.

The present inventors have found that ortho-phthalaldehyde (OPA) may be conveniently used as a latent covalent label in a flow method of the invention. OPA may be reacted with one or more amino groups of the component to form a detectable fluorescent label. OPA is preferably reacted with a component amino group in the presence of a thiol containing reagent, such as an alkyl thiol, such as β-mercapto ethanol (BME).

In one embodiment, the labelling reaction is a substantially quantitative reaction. Thus, in one embodiment, substantially all the diverted component is labelled. Further, where a component contains a plurality of groups that are capable of reacting with the label, substantially all of those groups react with the label. Thus, the recorded spectroscopic signal may be used to directly quantify the component in the flow. Moreover, a high degree of labelling (i.e. all components labelled and/or components having multiple labels) generally improves the detection of the component in the fluid flow. This is particularly important under flow conditions where the component in present at very low concentrations.

The labelling reaction should be suitable for use in a flow system. Thus, it is important that the labelling reaction occur in a relatively short time frame, as the residency time of the fluid in the device is not large. The present inventors have found that the OPA label reacts rapidly with components such as proteins, and is therefore suitable for use in the flow methods described herein.

In one embodiment, the labelling reaction time is at most 5 s, at most 2 s, at most 1.5 s or at most 1 s. The labelling reaction time may refer to the time taken to label at least 50 mole %, at least 80 mole % or at least 90 mole % of components, preferably 90 mole %. In one embodiment, the labelling reaction time may refer to the reaction half-time.

The present inventors have found that certain labels may be unstable under the flow conditions that are used in the methods of the present invention. Thus, the label may degrade over time, which has the effect of reducing the detected signal intensity during the analysis step. Thus, there is a risk that the recorded concentration of a component is less than the actual component concentration within a sample.

For example, it is known that the fluorophore formed from the reaction of ortho-phthalaldehyde (OPA) with an amino group, for example an amino group present in a polypeptide amino acid residue, lacks high chemical stability (see Jacobs et al.; Daito et al. and Nakamura et al.).

The methods of the present case allow a labelled component to be analysed very soon after the labelling step is complete. The labelling step may be regarded as complete when the signal intensity of the labelled component reaches a maximum. The appropriate analytical measurements for quantifying or identifying a component may be made at about the time the signal intensity reaches a maximum, or very soon after.

In the methods of the invention, the inventors have found that a latent label, such as ortho-phthalaldehyde (OPA), rapidly reacts with a component to generate labelled component. The labelling step may be complete within as little as three seconds, as judged by the increase in signal intensity, such as fluorescence intensity, to a maximum intensity during the labelling reaction. It follows that the analysis of the component occur at around three seconds from the start of the labelling reaction, or very soon after. Such analysis is entirety feasible using the fluidic systems described herein.

In one embodiment, the method of the invention includes a labelling step (v) prior to an analytical step (vi), and the analytical step is performed very soon after the initiation of the labelling step. For example, the analysis step may be performed within at most 1 second, at most 2 seconds, at most 3 seconds, at most 5 seconds, at most 10 seconds, at most 20 seconds or at most 30 seconds of the initiation of the labelling step.

The initiation of the labelling step may refer to the point in time when the component in a fluid flow is first permitted to contact a labelling reagent, for example at a fluid junction.

In some embodiments, it is not necessary to label a component, as the component may inherently possess functionality that is detectable using the spectroscopic methods described above, such as fluorescence spectroscopy. For example, where a component possesses fluorescently active groups these may be used for the fluorescent detection of that component.

Components that are or comprise polypeptides may possess the amino acids tryptophan, tyrosine and phenylalanine, the side chains of which have fluorescent activity. However, the presence of these residues may not be sufficient to allow the detection of the component. For example, the tyrosine and phenylalanine fluorescent activity is very weak, and is therefore hard to detect. Where there are few tryptophan, tyrosine and phenylalanine amino acid residues within the polypeptide, the fluorescent signal may be weak. In these cases it may be preferable to provide a fluorescent label having a greater fluorescent activity. The OPA-derived label is an example of a label that may be used.

Where the method of the invention includes the step of labelling the diverted component, the diverted flow is contacted with a fluid flow comprising the label (the label fluid flow) optionally together with associated reagents for the labelling reaction. The diverted flow and the label fluid flow are brought together at a junction downstream of the flow separator.

The component and label are permitted to intermix within the fluid flows thereby to label the component. The label flow and diverted flow may be permitted to flow along a mixing channel to ensure adequate time for labelling within the device, for example to allow for adequate time for labelling prior to spectroscopic analysis.

In one general embodiment, the secondary, tertiary and/or quaternary structure of the component, such as the secondary or tertiary structure, preferably tertiary structure, is altered after the separation step, prior to analysis.

Using the labelling methods described herein, the present inventors have found that is it not necessary to disrupt the secondary structure of a component, and it is sufficient to alter the tertiary and/or quaternary structure, where present, in order to allow appropriate labelling.

In one embodiment, the component is denatured prior to analysis.

The denaturing step is intended to make available functional groups on and within the component that may assist in the labelling and/or detection of the component. For example, where the component is a polypeptide, such as a protein, the denaturing step may expose amino, hydroxy and thiol functionality for reaction with a label.

The denaturing of the component may be effected by the addition of a denaturing reagent into the fluid flow. For example, where the component is a polypeptide SDS may be used as a denaturing reagent.

The denaturing step is not limited to the use of denaturing reagents and environmental changes, such as temperatures, may be used to achieve a denaturation.

The component may be denatured prior to labelling. Separation of the denaturing and labelling steps may be undertaken in order to minimise the precipitation of the component, which may occur during a combined denaturing and labelling step.

Where the denaturing step makes use of a denaturing reagent, the denaturing reagent may be provided in a fluid flow (denaturing flow) that is contacted with the diverted flow. The diverted flow and the denaturing fluid flow are brought together at a junction downstream of the flow separator. The component and denaturing reagent are permitted to intermix within the fluid flows thereby to denature the component. The denaturing flow and diverted flow may be permitted to flow along a mixing channel to ensure adequate time for denaturing within the device, for example to allow for adequate time for denaturing prior to contact with a labelling flow (where used) or prior to spectroscopic analysis.

Where the method also includes the step of labelling the component, the labelling step is undertaken downstream of the denaturing step.

Alternatively, the component may be denatured and labelled in one combined step. A combined denatured and labelled step may be used where there is little risk of precipitation of the components. Thus, in one embodiment, the label fluid flow additionally comprises the denaturing reagent. As shown herein, the junction where the diverted flow and the labelling flow (containing denaturant) are permitted to contact may be adapted to deal with denaturing problems. Thus, the surfaces of the fluid channels at the junction may be such that repel components in the fluid, for example hydrophilic surfaces may be used to prevent hydrophobic components adhering to the channel surfaces.

Where the diverted flow is contacted with a label flow or a denaturing flow, it is preferred that the contents of a flow are permitted to rapidly mix with the contents of the flow with which it is contacted. The rapid mixing is to ensure rapid labelling or denaturing of the component. This should be contrasted with the step of contacting the first fluid flow and the second fluid flow, where it is not necessary or desirable to rapidly distribute the component across both the first and second flows. For example, in a diffusion separation step, the early establishment of a uniform distribution of components in the separation channel is undesirable, as this will not allow components to be separated. For the diffusion separation it is necessary to establish a non-uniform distribution profile across the first and second fluid flows.

Flow Apparatus

The present invention provides a flow apparatus adapted for use in the methods of the invention. The flow apparatus permits first and second fluid flows to contact and form a laminar flow. The flow apparatus is adapted to divert a part of the first fluid flow, a part of the second fluid flow, or parts of the first fluid flow and the second fluid flow into a downstream diversion channel. The diversion channel is in fluid communication with an analysis channel and it follows that the flow from the diversion channel is provided into the analysis channel for analysis. Optionally, the fluid flow from the diversion channel is permitted to contact a reagent fluid flow, which is provided from an upstream reagent channel.

The flow device of the present invention may be an integrated device, such as a monolithic device, having an integrated network of channels. Thus, the device has no dead volume and band broadening is limited.

The flow apparatus makes use of small fluidic channels, particularly microfluidic channels, and therefore very small sample volumes may be analysed. Thus, components provided in fluids of less than a microliter volume may be analysed by the methods described herein. Furthermore, fluid flow techniques can also be used to analyse very dilute samples, by appropriate increases in the measurement times.

As described herein, the flow apparatus of the second aspect of the invention comprises a separation channel for first and second flows, and the separation channel is in fluid communication with a downstream flow separator, and a detection zone which is downstream and in fluid communication with the flow separator, wherein the separation channel is adapted to permit lateral movement of components between first and second flows and the flow separator is adapted to divert a part of the first fluid flow, a part of the second fluid flow, or parts of the first fluid flow and the second fluid flow, from the separation channel.

The cross sections of the separation channel, the diversion channel and the detection channel are typically in the micrometre range, and the fluidic device for use in the method of the first aspect of the invention may therefore be referred to as a microfluidic device.

The present invention also provides the microfluidic device as described herein.

The use of microfluidic channels to hold the first fluid and second fluid flows ensures that the flows take place at low Reynolds numbers. Under the diffusive separation steps described herein, convection and diffusion are the only relevant mechanisms of mass transport within the system. Accordingly, this allows accurate numerical calculations to be performed for each component of a given size, as described in further detail herein. Where electrophoretic methods are used for separation, convection and electrophoresis are the only relevant mechanisms of mass transport within the system.

The separation channel has suitable dimensions allowing for the generation and maintenance of a laminar flow of two (or three) streams within. The laminar flow of two streams means that the flows are side by side and are stable. Thus, there are typically no regions where the fluids recirculate, and the turbulence is minimal. Typically such conditions are provided by small channels, such as microchannels.

The general dimensions of the channels in the device are selected to provide reasonable mobilisation rates and analysis times. The dimensions of the device may also be selected to reduce the amount of fluid required for a sufficient analysis run.

Devices for use in the diffusion of a component across fluid flows, such as for use in dispersive measurements, are well known in the art, and are described, for example, by Kamholz et al. (*Biophysical Journal* 80(4): 1967-1972, 2001).

Devices for use in the electrophoresis of a component across fluid flows are well known in the art, and are described, for example, by Herling et al. (*Applied Physics Letters* 102, 184102-4 (2013)). Thus, the separation channel may be provided with electrodes alongside the channel length for deflecting (distributing) charged components across the channel. This is distinguishable from the devices described by the Ramsey group, where electrodes are placed at the channel ends, in order to distribute components along the channel length.

The separation channel is a channel having suitable dimensions allowing for the generation of a stable fluid flow and for achieving an adequate separation of components across the flow.

The separation channel is the region where the first fluid flow is brought into contact with the second fluid flow.

A reference to a separation channel herein is a reference to a channel having a substantially rectangular cross section. Thus, the separation channel may be formed of a substantially flat base with walls which extend substantially vertically therefrom, and optionally a top cover. Typically, the base and the walls are formed into a silicone substrate. The cover may be a glass cover, for example a standard glass slide or a borosilicate wafer.

Typically, other channels within the device, such as the flow separator, are also substantially rectangular.

The separation channel is in fluid communication with one or more reservoirs for the supply of first fluid. The separation channel is in fluid communication with one or more reservoirs for the supply of second fluid.

Typically the flow apparatus comprises a first supply channel and a second supply channel, which channels are in fluid communication with the downstream separation channel. The first supply channel is for holding the first fluid flow and the second supply channel is for providing the second fluid flow. The first and second supply channels meet at a junction with the downstream separation channel, which is adapted to hold the first and second fluid flows in a laminar flow. The channels provide fluid communication between the reservoirs and the separation channel.

In one embodiment, the separation channel comprises a first large cross section channel and a second small cross section channel that is downstream and in fluid communication with the large cross section channel.

The present inventors have found that the use of a large cross section channel at the junction where the first and second fluids first contact minimises fluid stagnation. Such channels are described in PCT/GB2013/052757.

The flow of fluids is along the longitudinal axis of the separation channel. The movement of a component or components from the first flow into the second flow, such as the diffusion of the component or components, is transverse to the longitudinal axis of flow, across the width of the channel.

The flow apparatus of the present invention may incorporate the flow device of the inventors' earlier work, as described in PCT/GB2013/052757, the contents of which are hereby incorporated by reference in their entirety.

The flow apparatus includes a flow separator downstream from and in fluid communication with the separation channel. The flow separator is a channel that is located across a part of the separation channel to collect a part of the laminar flow, and in particular to collect a part of the first fluid flow, a part of the second fluid flow or parts of the first and second fluid flows. The location and the width of the channel are selected depending upon the part of the laminar flow that is to be collected and the proportion of the flow that is to be collected.

The flow separator diverts a part of the flow from the separation channel. The flow separator provides the diverted flow to, and is in fluid communication with, a downstream detection zone.

The detection zone comprises a detection fluid channel for holding the fluid flow from the upstream flow separator. The detection zone may comprise the analytical device for analysing component that is held in the detection fluid channel.

In one embodiment, the detection fluid channel is in communication with one or more upstream flow supply channels, which fluid channels are downstream of the flow separator. The flow supply channels are for supplying label and denaturing reagent into the detection fluid channel. Each of the supply channels may be in communication with an upstream reservoir for holding the relevant agents such as label and denaturing reagent.

As described herein, label and denaturing reagent may be provided together in one fluid flow. Thus, a single supply channel may be provided upstream of the detection channel. The supply channel contacts the detection channel at a junction.

As described herein, label and denaturing reagent may be provided in separate fluid flows. Thus, a first supply channel may be provided for delivery of denaturing reagent into the detection channel. A second supply channel may be provided for delivery of label into the detection channel. The first and second supply channel contact the detection channel at first and second junctions respectively. The first junction is located upstream of the second junction.

Where the diverted flow is permitted to mix with a label flow and/or a denaturing flow in the detection channel, the detection channel may be provided with a mixing zone to ensure adequate mixing of component in the diverted flow with the label and/or denaturing reagent. The mixing zone may simply refer to an elongation of the detection channel that provides sufficient flow residency time for the fluids to allow for mixing and reaction of the component. The mixing zone may have a non-linear path to enhance mixing. The use of such channel architectures is well known to those of skill in the art.

The analytical device is not particularly limited and includes those device that are suitable for use with flow apparatus, and particularly microfluidic devices. A plurality of analytical devices may be provided to determine different physical and chemical characteristics of the component. The analytical devices may be arranged sequentially or in parallel.

The analytical device may be selected in combination with a component label in mind, or the inherent spectroscopic properties of the component in mind.

In one embodiment, the analytical device is a fluorimeter.

In one embodiment, the analytical device is a dry mass measuring device, such as a quartz crystal microbalance. The methods and devices of the present invention may be used together with the dry mass methods and apparatus of GB 1320127.2.

In one embodiment, the device comprises a reservoir for collecting the flow output from the analytical zone.

In one embodiment, the device comprises a reservoir for collecting the non-diverted flow from the separation channel.

The flow output from the analytical zone and the non-diverted flow from the separation channel may be collected together in a reservoir.

Components in the reservoir may be collected for further use and analysis.

The device of the invention allows fluids to flow through a separation channel, a flow separator and a detection zone. The establishment of flow through a fluidic device, such as a microfluidic device, is well known to those of skill in the art. For example, the fluid flows may be provided by syringe pumps that are the reservoirs for the various fluid channels. Alternatively, fluid flow may be established by gravity feed of fluids into the device. In another alternative, fluid flow may be established by drawing liquids through the device from the fluid exits in the device, for example using a syringe pump.

A device of the invention may incorporate or use one or more of these different flow systems.

The devices of the invention may be prepared in part using standard photolithographic techniques, such as described herein.

The channel surfaces of the fluid device may be adapted to prevent components from adhering to the surfaces. Thus, in one embodiment, the channel surfaces limit or prevent absorption of a component onto the surface.

In one embodiment, the channels within the fluidic device are hydrophilic or hydrophobic. The present inventors have found that the use of hydrophilic channel surfaces, particularly in the detection zone, prevent the absorption of hydrophobic components, such as hydrophobic proteins, thereby improving the analysis of components in the device. Similarly, hydrophobic channels may be used to prevent the absorption of hydrophilic components.

In particular the inventors have found that the use of hydrophilic or hydrophobic channel surfaces is beneficial at the stage of labelling and denaturing the component. The amount of insoluble material that is generated in the labelling step is minimised.

Hydrophilic channels may be prepared using techniques familiar to those in the art. For example, where the channels in a device are prepared from PDMS, the material may be plasma treated to render the surfaces hydrophilic. Here, the plasma treatment generates hydrophilic silanol groups on the surface of the channels. Such techniques are described by Tan et al. (*Biomicrofluidics* 4, 032204 (2010)).

In one embodiment, a channel in the microfluidic device, such as a channel in the detection zone, has a hydrophilic or hydrophobic surface.

In one embodiment, a channel in the microfluidic device, such as a channel in the detection zone, has hydroxyl groups at its surface. In one embodiment, a channel in the microfluidic device, such as a channel in the detection zone, has silanol groups at its surface.

In Flow Labelling

In a further aspect of the invention, the present inventors have established a method for labelling components in a fluidic device, and more particularly within a fluid flow. The components are provided in a non-uniform distribution across laminar first and second fluid flows. As described previously the separation of components across the first and second fluid flows may be undertaken under conditions where the component is retain in its native state. Once distributed, the components may then be labelled for subsequent analysis.

The labelling method comprises the steps of:
(iii) providing a distribution of a component across contacting first and second flows, such as first and second laminar flows;
(iv) diverting at least part of the first fluid flow, at least part of the second fluid flow, or at least parts of the first fluid flow and the second fluid flow, wherein the diverted part comprises the component;
(v) labelling the component in the diverted part of the fluid flow; and optionally
(vi) analysing the component in the diverted part of the fluid flow.

In one embodiment, the method comprises the preliminary steps of:
(i) providing the component in a first fluid flow;

(ii) contacting the fluid flow with a second fluid flow, such as to generate a laminar flow; and step (iii) is permitting the component to join the second fluid flow, thereby to obtain a distribution of the component across the first and second fluid flows.

In one embodiment, step (iv) is diverting at least part of the second fluid flow.

In one embodiment, step (vi) is present.

The present inventors have found that the labelling and analysis steps are most effective when the labelling step introduces a fluorogenic label to the component of interest. The labelling is also most effective when the label is a covalent label, as this eliminates the effect of varying component concentration and conformational motifs on dye binding affinity. It is also advantageous to label all the appropriate reactive groups, regardless of the component sequence, structure, or concentration. The labelling is also most effective when it is rapid, and reaches completion (for example, at a quantitative level) on the second to minute timescale of a microfluidic experiment.

The present case describes the use of ortho-phthalaldehyde (OPA) for generating a labelled component.

Other embodiments of this aspect of the invention are as described above for the methods of analysing a component.

Exemplary Methods and Devices of the Invention

The present invention provides methods for separating and analysing components in a fluid flow, preferably using the microfluidic apparatus described herein. Set out below, with reference to the accompanying figures, is a description of various embodiments of the invention.

The device of the invention is for separating and detecting a component in a mixture. The apparatus comprises a separation channel for first and second laminar flows, and the separation channel is in fluid communication with a downstream flow separator. A detection zone is provided, which is downstream and in fluid communication with the flow separator. The separation channel is adapted to permit lateral movement of components between contacting flows, such as laminar flows, and the flow separator is adapted to divert a part of the first fluid flow, a part of the second fluid flow, or parts of the first fluid flow and the second fluid flow, from the separation channel. The detection zone is adapted to allow the analysis of a component in a fluid channel of the detection zone.

Shown inset to FIG. 1A is a schematic of a microfluidic device according to one embodiment of the invention. The device is shown in further detail in FIG. 13. The device is suitable for separating components by diffusive methods. The device comprises a separation channel 1 in fluid communication with a downstream flow separator 7, which is in fluid communication with a downstream detection zone 9.

The device is provided with a separation channel 1, which is supplied by an upstream first fluid flow channel 2 and an upstream second fluid flow channel 3. The first and second flow channels join at a junction 4. The first and second channels are supplied by upstream reservoirs 5 and 6 respectively. The first reservoir 5 provides a fluid containing a component, optionally together with other components, for example as part of a multicomponent mixture. The first fluid is permitted to exit the reservoir and flow along the first fluid channel. At the junction 4, the first fluid flow is permitted to contact a second fluid flow, which is provided from the second reservoir 6 via the second fluid channel.

The first and second fluid flows may develop into a laminar flow in the separation channel 1. As the flow passes down the separation channel 1, component in the first fluid flow is permitted to diffuse into the second fluid flow. Components or different size (different hydrodynamic radius) diffuse at different rates, thereby generating a diffusion profile across the first and second fluid flows. Smaller components will diffuse more rapidly towards to boundary of the second fluid flow at the channel wall compared to larger components.

As described herein, the junction 4 of the first and second fluid flow channels may be a channel having a large cross section, which subsequently develops into a downstream small cross section channel (this is not shown in FIG. 13, but is visible in the device shown in FIG. 5A.

At the downstream end of the separation channel 1, there is provided a flow separator 7. The flow separator diverts a part of the first or second fluid flows, or parts of both the first and second fluid flows. The flow separator of FIG. 13 is intended to divert a part of the second fluid flow, and more particularly, the part of the second fluid flow that is associated with the components of a smaller size (i.e. those that have diffused more rapidly towards the boundary of the second fluid flow at the channel wall).

The flow separator 7 is placed across a part of the second fluid flow to collect a part of the second fluid flow. Diverted flow passes into a detection channel 8 of the downstream detection zone 9.

The diverting step is typically undertaken before component in the first fluid flow has diffused to the boundary of the second fluid flow at the channel wall. Thus, the diffusion profile of the component is non uniform across the first and second fluid flows (because the component has not reached an equilibrium distribution across the first and second fluid flows).

The remaining part of the laminar flow is collected and permitted to flow to a downstream exit reservoir 10 via a collection channel 11.

The detection zone 9 comprises a detection channel 8 which is in fluid communication with the upstream flow separator 7. The detection channel 8 is also in fluid communication with an upstream labelling channel 12, which joins the detection channel 8 at a junction 13. The labelling channel is supplied from an upstream labelling reservoir 14. A labelling mixture, optionally containing a denaturant, is provided in the labelling reservoir 14 and is permitted to join the flow in the detection channel at the junction 13, via the labelling channel 12. In this way, a labelling agent may be provided into the flow that is diverted from the separation channel 1 (diverted flow).

The labelling flow joins enters the detection channel 8 and the labelling agent labels the component. The labelling flow and the diverted flow are permitted to intermix for sufficient time to allow for the labelling of the component. The fluid in the detection channel 8 is then analysed in an analytical region 15 of the detection zone 9, for example using fluorescent spectroscopy. Once the analysis is complete, the fluid in the detection channel is permitted to exit the detection zone 9 and is collected in a downstream exit reservoir 10. The detection channel 8 joins the collection channel 11, thereby to recombine the fluid flows from the separation channel 1.

Yet another adaptation of the device is shown in FIG. 12, where the detection channel 8 is in fluid communication with an upstream labelling channel 12 and an upstream denaturing channel 18. Each of the labelling and denaturing channels 12 and 18 joins the detection channel 8 at junctions 13 and 19 respectively. The junction 19 of the denaturing channel is upstream of the junction of the labelling channel 13 with the detection channel 8. Diverted fluid in the detection channel 8 is first contacted with denaturant provided from the denaturing channel 18, thereby to denature a component in the diverted flow. The flow is then subsequently contacted with a labelling flow from the labelling channel 12, thereby to label the (denatured) component in the flow. The distance between the junctions 12 and 18 is sufficient to allow the complete denaturing of the component in the fluid flow.

Figure 13:
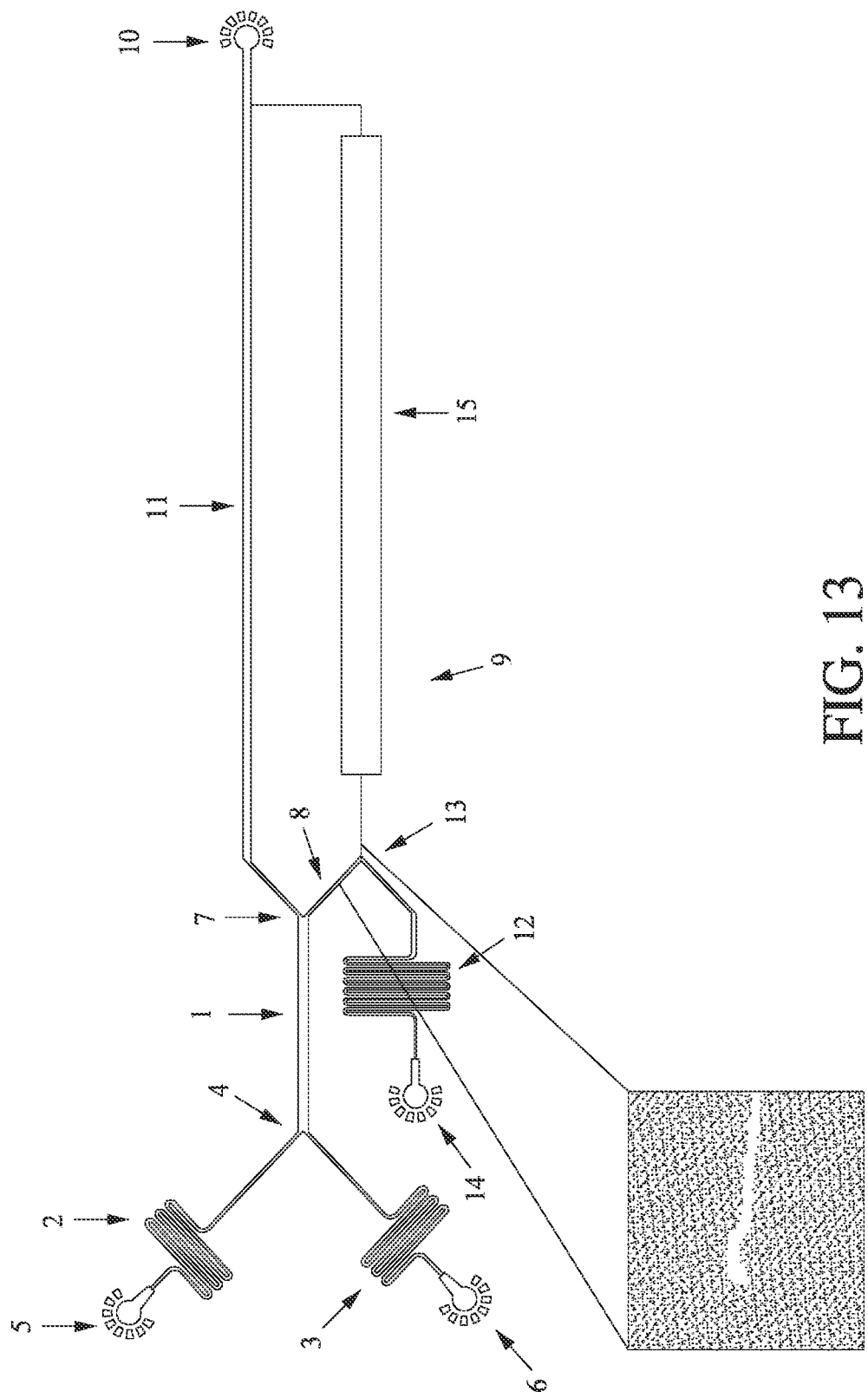
FIG. 13 is an enlarged schematic of the diffusion microfluidic device of FIG. 1A.

In other embodiments, the denaturant and label are provided together in the labelling flow, such as shown in FIG. 7 and FIG. 13.

Figure 7A:
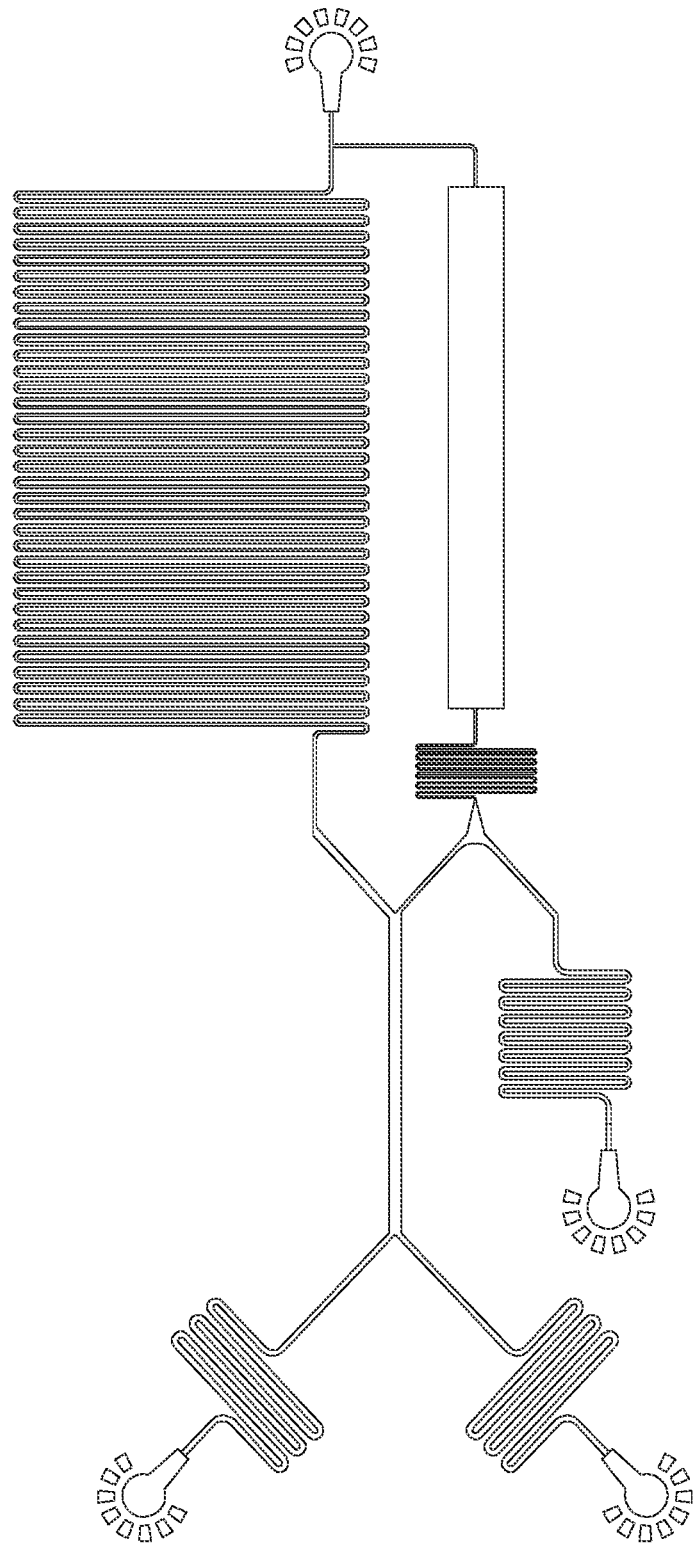
FIG. 7A-7C shows a schematic of a diffusion microfluidic device according to a further embodiment of the invention.

An adaptation of the device of FIG. 1A and FIG. 13 is shown in FIG. 7A. Here, the detection channel 7 has a mixing zone downstream of the junction 13. The mixing zone allows labelling material to mix with the diverted flow from the separation zone for a sufficient time to allow labelling prior to analysis in the analysis channel 15 of the detection zone 9.

Figure 10A:
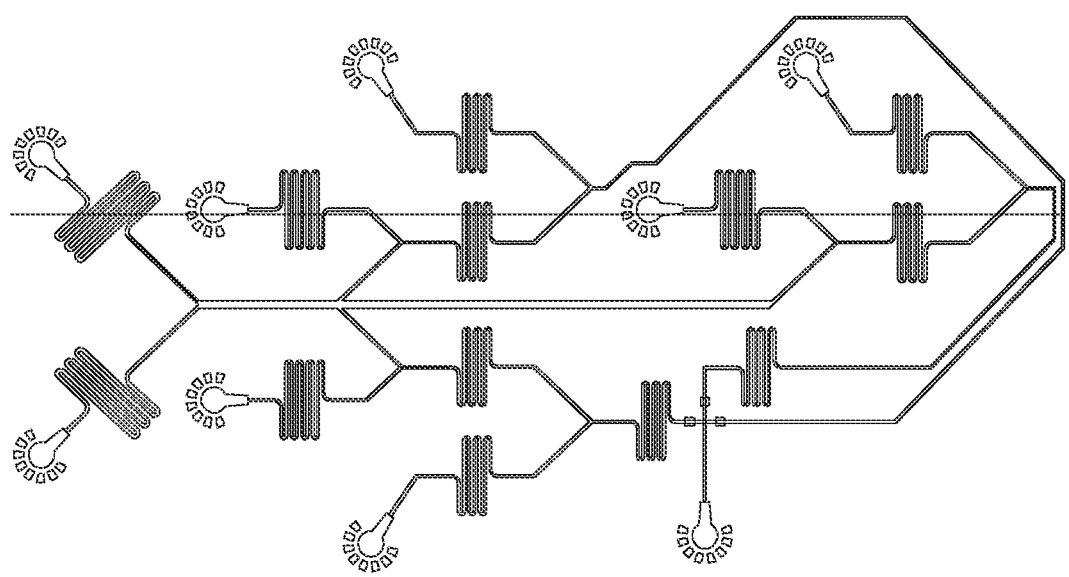
FIG. 10A shows a schematic of a diffusion microfluidic device according to an embodiment of the invention, where the device diverts a plurality of parts of the first and second fluid flows, and further where component in each diverted flow is labelled after diversion and subsequently analysed.
Figure 10B:
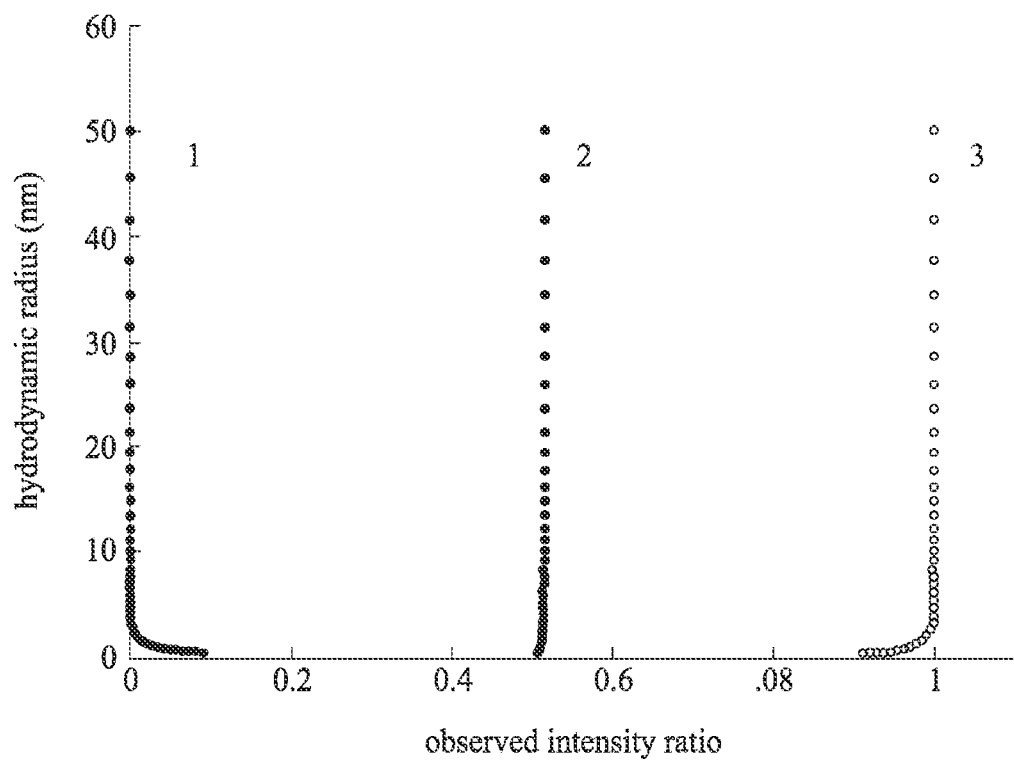

A further adaptation of the device of FIG. 1A and FIG. 13 is shown in FIG. 10. In this device, a portion of the flow from the separation channel 1 is diverted as before, denatured and labelled in separate steps, and analysed as above.

The remaining portion of the flow is collected as a further divided plurality of flows. Components in each of these additionally diverted flows is also labelled and analysed, as described in relation to the diverted flow. In this way, the fluid flow in the separation channel 1 is separated into three flows, where each of the three flows has a different mixture of components, which is representative of components having different diffusion properties. All the components in the flow are subsequently analysed, in their separated form. Thus, the device of the invention also for the separation and complete analysis of all the components provided in in the first fluid flow.

Figure 14:
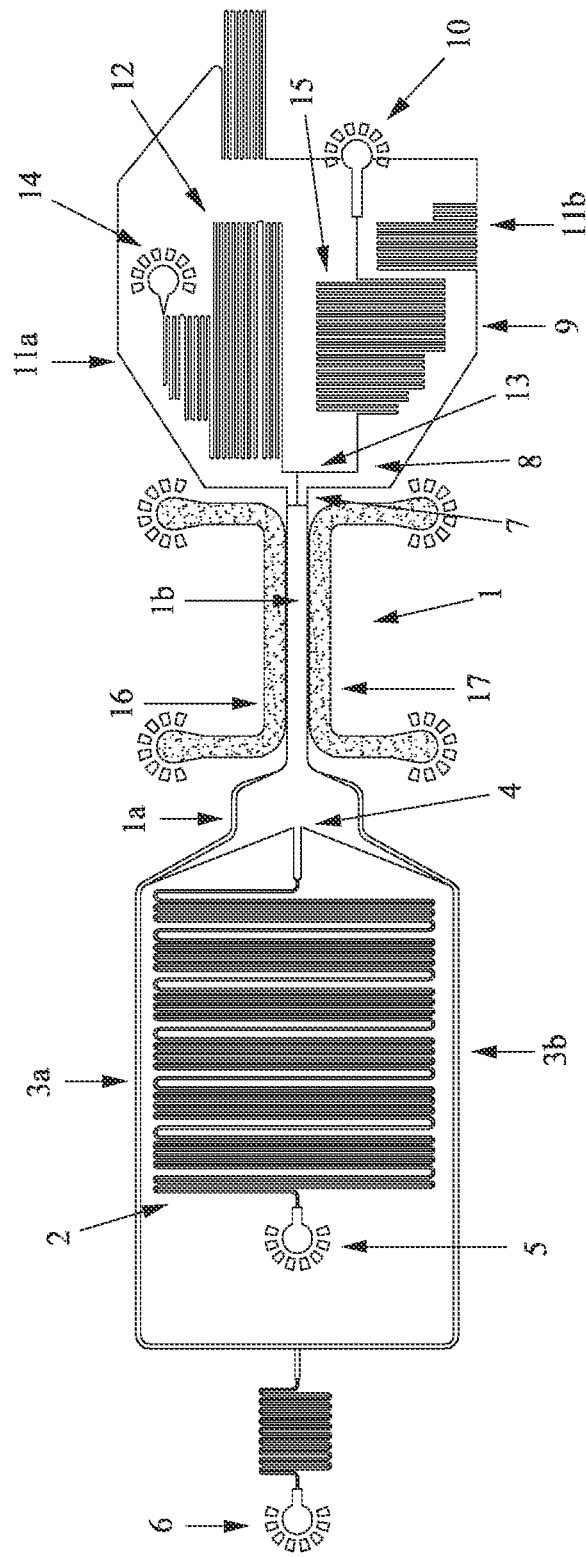
FIG. 14 is an enlarged schematic of the diffusion microfluidic device of FIG. 5A.

Another device of the invention is shown in FIG. 14. The device is suitable for separating components by electrophoretic methods. The device comprises a separation channel 1 in fluid communication with a downstream flow separator 7, which is in fluid communication with a downstream detection zone 9.

The device is provided with a separation channel 1, having a region of large cross section 1a and a downstream region of small cross section 1b, which is supplied by an upstream first fluid flow channel 2 and upstream second fluid flow channels 3a and 3b. The first and second channels join at a junction 4. The first and second channels are supplied by upstream reservoirs 5 and 6 respectively. The first reservoir 5 provides a fluid containing a component, tonally together with other components. The first fluid is permitted to exit the reservoir and flow along the first fluid channel. At the junction 4, the first fluid flow is permitted to contact a second fluid flow, which is provided from the second reservoir 6 via the second fluid channels 3a and 3b.

The use of a large cross section channel at a fluid junction is associated with decreased stagnation at the junction. See, for example, PCT/GB2013/052757.

The first and second fluid flows may develop into a laminar flow in the separation channel 1. The second fluid flows are provided either side of the first fluid flow. Electrodes 16 and 17 are provided either side of the separation channel 1. The electrodes are in electrical communication with a power supply (not shown). In use, the electrodes provide an electric field across the separation channel 1, such as the small cross section region 1a of the separation channel 1.

As the flow passes down the separation channel 1, component in the first fluid flow is deflected into the second fluid flow in a response to the applied electric field. The direction and degree of deflection are dependent upon the charge and the charge-to-size ratio of the component or components in the first fluid flow.

Components of different charge are deflected in directed directions, either towards electrode 16 or towards electrode 17. Components differing in their charge-to-size ratio (and having the same charge) are deflected by different amounts into the second fluid flow.

Components having a higher charge and/or smaller size will be deflected to a greater degree towards to boundary of the second fluid flow at the channel wall compared to components having a smaller charge and/or larger size.

At the downstream end of the separation channel 1, there is provided a flow separator 7. The flow separator diverts a part of the first or second fluid flows, or parts of both the first and second fluid flows. The flow separator of FIG. 13 is intended to divert a part of the second fluid flow, and more particularly, the part of the second fluid flow that is associated with the components having a particular charge (i.e. those attracted towards electrode 16) and having a smaller charge and/or larger size (i.e. those that are deflected least rapidly towards the boundary of the second fluid flow at the channel wall).

The flow separator 7 is placed across a part of the second fluid flow to collect a part of the second fluid flow. Diverted flow passes into a detection channel 8 of the downstream detection zone 9. The flow separator 7 and detection channel 8 is shown in greater detail in FIG. 5B.

The flow separator 7 is placed across a part of the second fluid flow to collect a part of the second fluid flow. Diverted flow passes into a detection channel 8 of the downstream detection zone 9. The diverting step is typically undertaken before component in the first fluid flow has deflected to the boundary of the second fluid flow at the channel wall.

The remaining parts of the laminar flow are collected and permitted to flow to a downstream exit reservoir 10 via collection channels 11a and 11b.

The detection zone 9 comprises a detection channel 8 which is in fluid communication with the upstream flow separator 7. The detection channel 8 is also in fluid communication with an upstream labelling channel 12, which joins the detection channel 8 at a junction 13. The labelling channel is supplied from an upstream labelling reservoir 14. A labelling mixture, optionally containing a denaturant, is provided in the labelling reservoir 14 and is permitted to join the flow in the detection channel at the junction 13, via the labelling channel 12. In this way, a labelling agent may be provided into the flow that is diverted from the separation channel 1 (diverted flow).

The labelling flow joins enters the detection channel 8 and the labelling agent labels the component. The labelling flow and the diverted flow are permitted to intermix for sufficient time to allow for the labelling of the component. A mixing zone is provided upstream of the analytical region 15 for this purpose. The fluid in the detection channel 8 is then analysed in the analytical region 15 of the detection zone 9, for example using fluorescent spectroscopy. Once the analysis is complete, the fluid in the detection channel is permitted to exit the detection zone 9 and is collected in a downstream exit reservoir 10, thereby to recombine the fluid flows from the separation channel 1.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

Experimental

Bulk Quantitative Labelling Experiments

Bovine serum albumin (product #A7906), Lysozyme (#62970), β-lactogloublin (#L3908), sodium dodecyl sulfate (#71725), sodium bicarbonate (#8875), HEPES (#H3375), and ortho-phthalaldehyde (#79760) were obtained from Sigma Aldrich. Sodium carbonate decahydrate was obtained from East Anglia Chemical Company (product #1353). β-mercaptoethanol was obtained from Thermo Scientific (product #35602).

A variety of OPA:BME ratios were surveyed, and 1:1.5 proved optimal. A variety of buffer conditions were also surveyed. Optimal quantitative detection sensitivity was obtained between pH 9.5 and 10.5, using carbonate buffers of high ionic strength (100 to 500 mM). The labelling reaction is tolerant of a variety of buffers. Initially it was thought that buffers containing primary amines, such as Tris, would interfere with the quantitative labelling reaction. However, recent work has suggested that Tris-type buffers are not problematic.

A variety of labelling conditions were surveyed. Initial experiments determined that for determining protein concentrations in the nM to high μM range, final OPA/BME concentrations of 6 mM OPA, 9 mM BME were optimal. A variety of denaturants and surfactants were examined, including 20-40% DMSO, 30-40% EtOH, 2% SDS, alone or in combination with 0.5-5% Tween-20.

A standard labelling solution of 12 mM OPA, 18 mM BME, 4% SDS, and 200 mM carbonate, pH 9.5-10.5 was used for the electrophoretic and diffusional separation and detection experiments. This solution was typically prepared in advance and mixed in a 1:1 volume ratio with the protein solution of interest. The labelling solution can be stored for up to 1 week with no detectable loss of performance, if protected from light. BSA, Lysozyme, and β-lactoglobulin solutions varying in concentration were prepared in 5 mM HEPES buffer, pH 7 and mixed with the labelling solution above.

For bulk detection and labelling experiments, three replicates of each condition were loaded into low protein-binding, half-area 96 well plates (Corning, product #3881), and covered with adhesive aluminium sealant sheets (Costar product #6570). An endpoint fluorescence measurement was taken on a BMG labtech FLUOstar OPTIMA Plate Reader, using 350+/−10 excitation, and 440+/−10 emission filters.

Microfluidic Device Fabrication and Operation

The microfluidic diffusion devices were fabricated using standard lithographic approaches (see Kim, P. et al. Biochip Journal 2, 1-11 (2008)). Briefly, devices were designed in Autocad, a binary mask was printed on a sheet of acetate (MicroLitho), with clear regions corresponding to the intended channels in the microfluidic device, and black regions corresponding to the background. A master—the positive impression of the device to be cast—was prepared by spin-coating 25 μm of MicroChem SU-83025 permanent epoxy negative photoresist onto a silicon wafer, laying the mask on top of the photoresist, cross linking the exposed epoxy with collimated UV light, and finally removing areas of the uncrosslinked polymer with a propylene glycol mono methyl ether acetate (PGM EA) developer (MicroChem).

Devices were cast in polydimethylsiloxane. PDMS elastomer and curing agent (Dow Corning, product #184) are mixed 1:1 w/w. It is important to ensure that mixing is complete: manual agitation for 2-5 minutes is important for appropriate cured elastomer performance. When black devices were desired, approximately 20 mg of carbon nano-powder (Sigma, product #633100) was added and mixed thoroughly. Large clumps of nanopowder were sedimented via centrifugation at 3,000 rpm for 10 minutes in an Eppendorf 5804 R centrifuge. The mixed elastomer and curing agent were poured onto the masters, bubbles were removed via vacuum desiccation for approximately 10 minutes, and the devices were baked for 60-75 minutes at 70° C. Once cooled, devices were cut out, and holes punched at the inlets and outlets with 0.75 mm Harris Uni-Core punchers. After removing debris with sticky tape, they were plasma bonded to Thermo Scientific 76×26 mm glass slides (catalogue #8037) using an Electronic Diener Femto Plasma bonder. The bonded devices were baked at 70° C. for 10 minutes.

For the electrophoretic-based separation experiments, electrodes were fabricated in a single step according to published procedures (see Herling et al.). Briefly, electrode channels were delineated with 25 μm PDMS pillars. After devices were bonded, they were headed to 78° C. on a hot plate, and low-melting point solder (an InBiSn alloy composed of 51% In, 32.5% Bi, 16.5% Sn, Conro Electronics) was pushed into the electrode inlets. The high surface tension of the molten solder confined it to the electrode channels, whilst ensuring contact between the electrodes and the aqueous buffer.

The flow in the device was controlled using a neMESYS syringe pump. Brightfield and fluorescence images were acquired using a Zeiss AxioObserver Microscope, fitted with a 365 nm Cairn OptoLED (Photometrics), and a Chromo 49000 DAPI filter for the uorescence images. 2.5×, 5×, 10×, and 20× objectives were used. Exposure times of between 100 ms and 1000 ms were used. Fluorescence images were taken in the dark, and are usually the result of averaging 10 separate images. In some cases images were binned to increase signal to noise ratio. Images were background corrected by subtracting flatfield images taken with the same exposure settings.

Microfluidic Experiments

Bovine insulin was purchased from Seralab (product #GEM-700-112-P). The insulin contained 0.6% w/w Zn' and was used as received. The remaining experimental protocols are described in detail below.

Electrophoretic PSL experiment: 10 mg/mL BSA and 10 mg/mL lysozyme were each solubilized in 5 mM HEPES, pH 7. To the solutions was added 100 μM rhodamine 6 g (Sigma). The solutions were then filtered through 0.22 μm syringe filters. Labelling solutions containing 11 mM OPA, 16.4 mM BME, and 3.63% SDS in 180 mM carbonate at pH 9.5 were prepared. The solutions were loaded into each of the device inlets, and then the electrodes were soldered to wires which were in turn connected to a DC voltage supply. The position of the rhodamine 6 g tracer (which does not interfere with OPA fluorescence) was used to verify device alignment. Detection was verified by examining the changing position of the rhodamine beam at −5 V, 0 V, and 5 V. Having verified successful detection, OPA fluorescence intensity was measured in the observation region as the voltage was varied between −10 and 8 V. Formation of fluorescence at the mixing interface was also visualized. It was important to avoid applying high voltages for only short periods of time, to avoid gas bubble formation at the electrodes due to electrolysis. The same procedure was repeated for a separate device, loaded with the lysozyme solution.

Labelling

The separation and detection of components described herein uses the fast spatial segregation possibilities of microfluidics. With this approach, unmodified components, such as biomolecules, are spatially separated according to their intrinsic properties like size or charge. These components may then be collected and subsequently detected. The detection step may include exposing separated component to a new set of conditions which promote rapid, complete reaction with a label and subsequent quantitative detection.

Important to the labelling approach is the fusion of two, previously unrelated ideas. The first is the reaction of a component with a latent covalent label (LCL), a molecule which rapidly becomes fluorescent only upon reaction with relevant functional groups on the component. The second is a rapid denaturation step which exposes all of the relevant functional groups to solvent, accelerating and ensuring complete reaction with the latent label.

The latent covalent labelling approach is crucial here as it removes the requirement for sample purification following the labelling reaction. As only the labelled substrate is fluorescent, the unreacted labelling precursor does not need to be removed. This allows the labelling and detection process to directly follow the separation scheme on a microfluidics chip. Additionally, the covalent nature of the labelling reaction ensures that all species are permanently modified, such that relative detection sensitivities does not depend on, for example, differences in dye binding affinity.

Two classes of latent covalent labels can be envisioned. In the first, reaction with a substrate moiety removes a group initially present on the label that quenches its fluorescence. In the second, the fluorophore itself is formed during the labelling reaction, for example through the formation of an extended conjugated system.

One of the limitations of microfluidic approaches is the fast reaction kinetics required for fluid analysis with a microfluidic device. The first approach discussed above was explored, in the expectation that the formation of a fluorophore through the extension of a conjugated 20 system could act as a sufficient driving force for rapid, in-device reaction.

A variety of such fluorogenic compounds was studied, and promising results with obtained using ortho-phthalaldehyde (OPA).

Labelling with OPA

In 1971, Roth et al. discovered that if OPA is reacted with isolated amino acids in the presence of a thiol such as β-mercapto ethanol (BME), a blue fluorescent product is formed (Roth *Analytical Chemistry* 43, 880{882 (1971)}. The observed rapid kinetics then led the authors to develop a related technology for on-line amino acid modification following separation in an ion exchange column (Roth et al. *Journal of Chromatography* 83, 353-356, (1973)). This modification technique was subsequently shown to be superior in terms of detection sensitivity and rapidity of room temperature reaction to more standard peptide modification systems, such as those utilizing ninhydrin (Benson et al. *PNAS* 72, 619-62235 (1975)). Subsequent efforts have described the use of OPA as an amino acid or biomolecule derivtisation reagent prior to, during, or following capillary electrophoresis (Oguriet et al. *Journal of Chromatography A* 787, 253-260 (1997); Jacobson et al. *Anal. Chem.* 1994, 66, 3472). There have been, to the inventors' knowledge, no reported examples of the use of OPA as in-device derivitisation reagent following microfluidic spatial separation.

Figure 25:
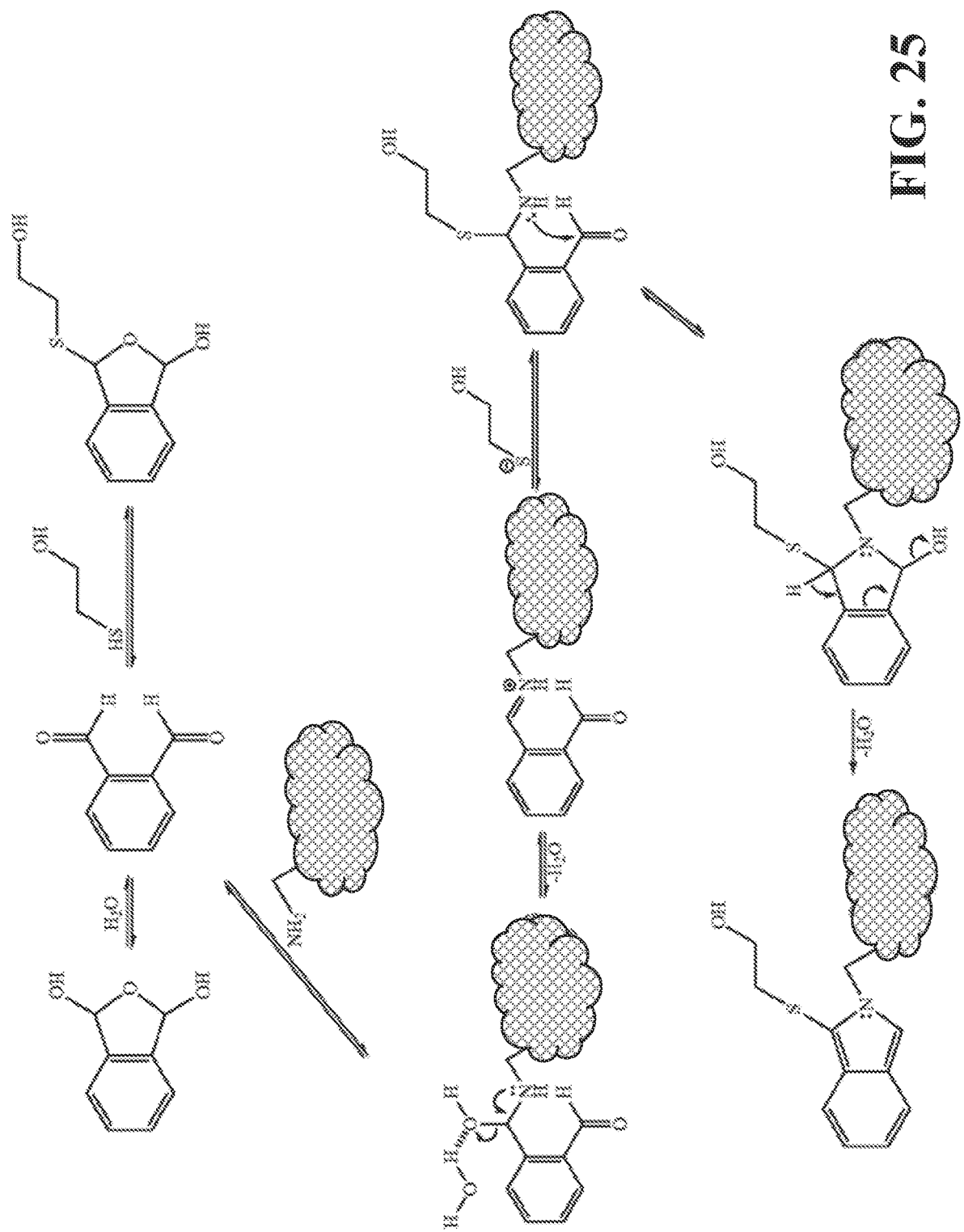
FIG. 25 shows the OPA reaction mechanism under alkaline conditions.

The OPA reaction mechanism under alkaline conditions is as shown in FIG. 25, which is adapted from Sternson and Garcia-Alvarez-Coque (Sternson et al. Anal. Biochem. 144, 233-246 (1985); Garcia-Alvarez-Coque et al. Anal. Biochem. 17, 1-7 (1989)). The OPA dialdehyde is in equilibrium with the hemiacetal and thiohemiacetal forms. The dialdehyde reacts with primary amines exposed on the protein surface, and water is lost, forming a highly reactive imine. Attack of the BME thiolate on the imine releases a secondary amine for attack on the pendant aldehyde, closing the 5-membered ring. The reaction becomes irreversible with the extension of conjugation and loss of water.

Detection Sensitivity

Nanogram detection sensitivity for protein concentration with OPA has been reported in the literature (Zawieja et al. *Analytical Biochemistry* 142, 182-188 (1984)). The literature study obtained this level of sensitivity using μM protein concentrations in <nL sample volumes, however, and allowed for reaction times of at least 30 minutes.

The detection sensitivity for linear protein concentration determination using OPA was determined under the constraints of microfluidic derivitisation.

The microfluidic device design is shown as an inset in FIG. 1A, and is described above in relation to the Exemplary Methods and Devices. The reaction proceeds under flow and thus is at steady state, but the total reaction volume, defined as the total volume of labelled protein at any time point, is 0.38 μL. Fluorescence intensity was measured in a detection zone, shown as an elongate rectangle in FIG. 1A. In this experiment, fluorescence intensity was measured 18 s after dye and protein streams initially contacted one another in the Y junction.

As shown in FIG. 1A, when BSA is labelled with OPA in a microfluidic device, the OPA fluorescence intensity is linear with BSA concentration down to 15 nM. This detection limit could be further decreased by denaturing the protein prior to or during the labelling reaction using suitable, low-background, conditions, as will be discussed below, or by increasing the device path length.

Figure 1B:
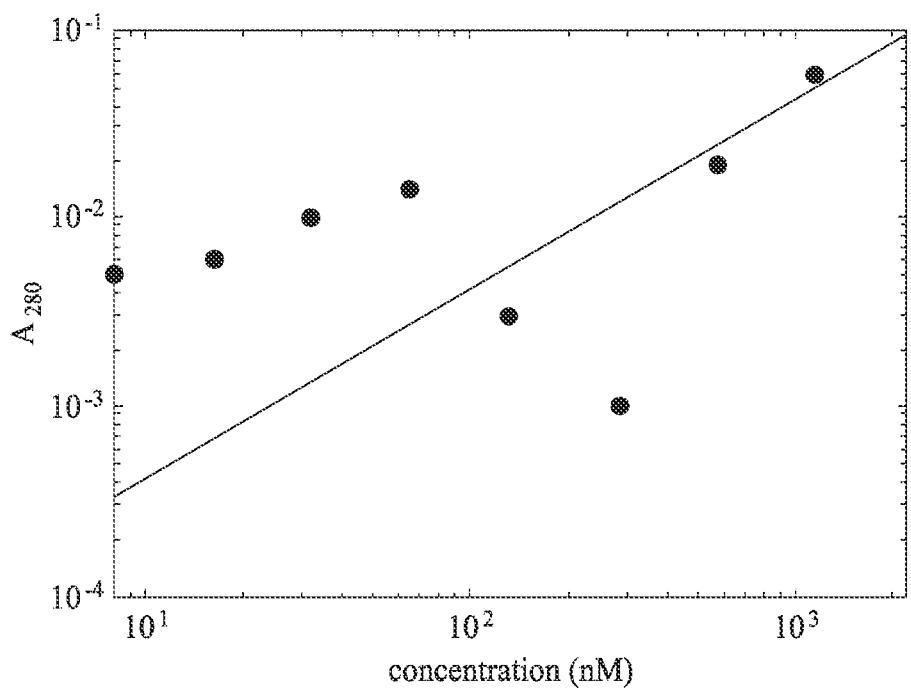
FIG. 1B the change in absorbance intensity at $A_{280}$ with the change in bovine serum albumin concentration. The red dots correspond to measurements for which the sample yielded a lower absorption than the buffer blank. A detection limit of approximately 600 nM was obtained.

The device used for these experiments had a path length of 25 μm, and path lengths of up to 100 μm are attainable without changing the fabrication process. It is expected that the sensitivity for a 100 μM path length device to be reduced to 3.75 nM. In contrast, the absorption detection sensitivity is shown in FIG. 1B. A linear relationship between $A_{280}$ and BSA concentration was only obtained for BSA concentrations greater than 585 nM for a 1 mm path length. Converting to the 25 μm path length used in the microfluidic device, a detection limit of 23.4 μM is expected. Thus, the in-device derivitisation method is over 1,500 times more sensitive than the absorption method at determining the concentration of unmodified protein.

Even in the current configuration, a linear relationship is observed between protein concentration and fluorescence intensity down to 0.38 ng of protein, which is a result comparable to literature values (Zawieja et al. *Analytical Biochemistry* 142, 182-188 (1984)), but for approximately 1,000 fold lower absolute concentrations of protein, and approximately 100 times lower reaction time.

Quantitative Labelling

Another key component of the labelling approach described herein is the recognition that, by denaturing components of interest (e.g. proteins) and exposing all relevant functional groups for reaction (e.g. amino groups), complete labelling is attainable. Using OPA-based labelling, fluorescence intensity can be quantitatively used to determine protein concentration. Denaturation can take place either before or during labelling.

A variety of conditions have been explored, and for several denaturing and labelling mixtures, protein concentration can be quantitatively related to OPA fluorescence intensity, as discussed below. FIG. 3 shows the conditions used in the diffusional and electrophoretic separation and detection methods described below.

Figure 2:
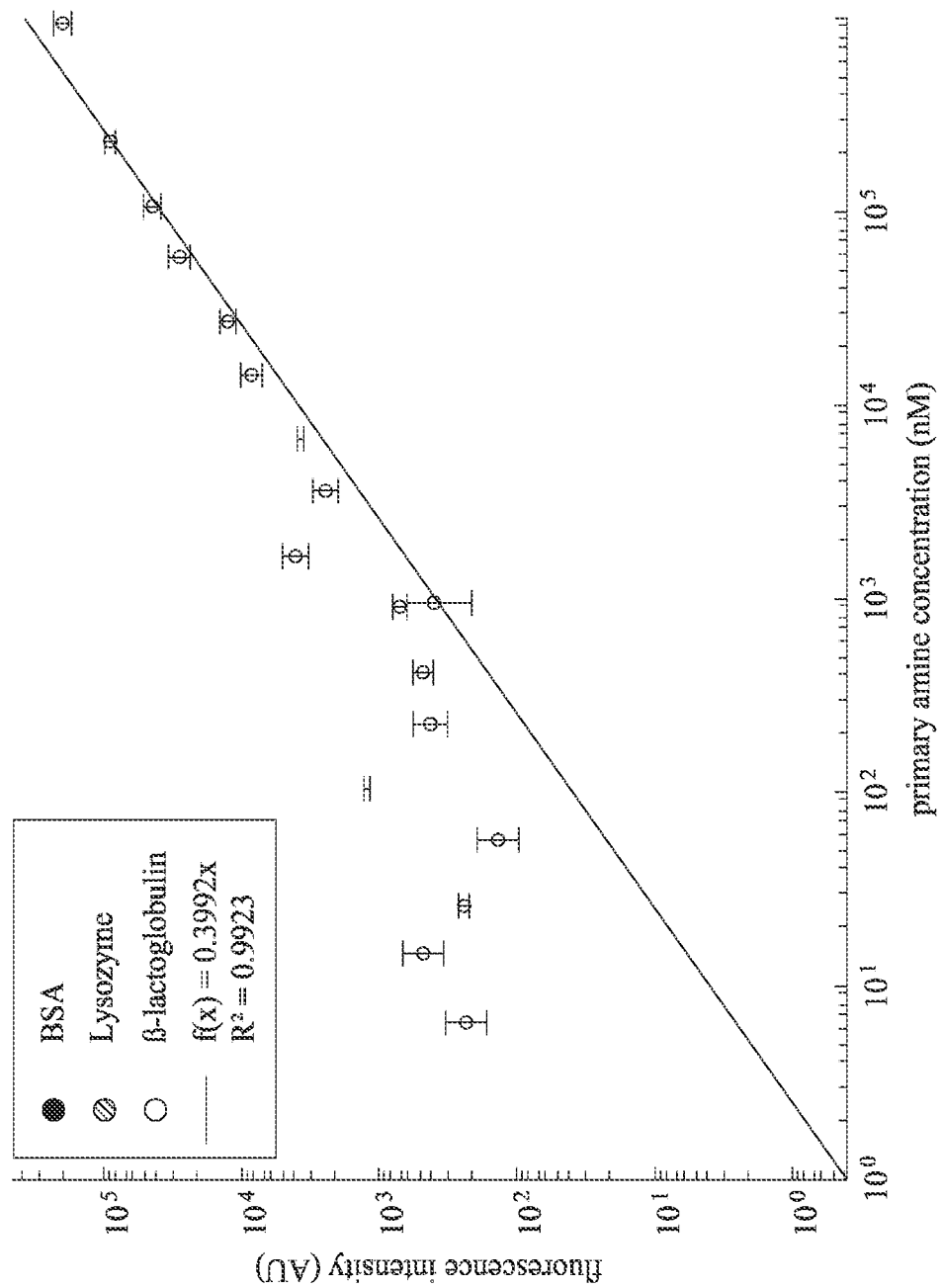
FIG. 2 shows the change in fluorescence intensity with the change in effective primary amine concentration for BSA, lysozyme and β-lactoglobulin. Varying concentrations of BSA, lysozyme, and β-lactoglobulin were denatured and labelled using SDS (sodium dodecyl sulfate), OPA (ortho-phthalaldehyde) and BME (beta-mercaptoethanol) in alkaline buffer. Protein concentrations were converted to primary amine concentrations, and the linear relationship between primary amine concentration and OPA fluorescence intensity is shown. For this set of denaturing conditions, the relationship between primary amine concentration and OPA fluorescence intensity is well described by the linear regression down to 60 nM protein concentration.

As shown in FIG. 2, varying concentrations of BSA, lysozyme, and β-lactoglobulin, three model proteins with widely varying isoelectric points (IEP's), molecular weights, and primary sequences, were mixed with a labelling mixture for final labelling concentrations of 6 mM OPA, 9 mM BME, 2% sodium dodecyl sulfate (SDS), and 100 mM carbonate, pH 10.1. Protein primary sequences were used to convert final protein concentrations to primary amine concentrations, and the relationship between OPA fluorescence intensity and primary amine concentration for the three proteins is plotted. A linear regression yields a 0.99 correlation coefficient. The presence of the SDS in the labelling solution does slightly increase the background from unreacted dye. At the high ionic strengths used in this experiment, SDS micelles form a complex variety of structures (Almgren et al. *Journal of Colloid and Interface Science* 202, 222-231 (1998)), some of which would be expected to scatter the unreacted dye background fluorescence.

The quantitative labelling method can be used to determine unknown peptide concentrations. Amyloid-β(1-42) (Aβ(1-42)) has no tryptophan residues and a low extinction coefficient of 1,400l/Mcm (Walsh et al. *FEBS Journal* 276, 1266-1281 (2009)). The only literature-documented procedure shown to produce reproducible kinetic data for the aggregation of Aβ (1-42) involves expression of the recombinant peptide, purification, and SEC filtration of the purified peptide immediately prior to kinetic analysis in order to remove pre-formed aggregates (Walsh et al. *FEBS Journal* 276, 1266-1281 (2009); Hellstrand et al. *ACS Chemical Neuroscience* 1, 13-18 (2010)). However, this often results in low concentrations of purified monomer which are difficult to detect by absorption. Accordingly, obtaining reproducible kinetic data for Aβ(1-42) depends additionally on comparing only samples which have been prepared from a single batch of purified monomer, such that each sample will have the same relative error in concentration.

Figure 3A:
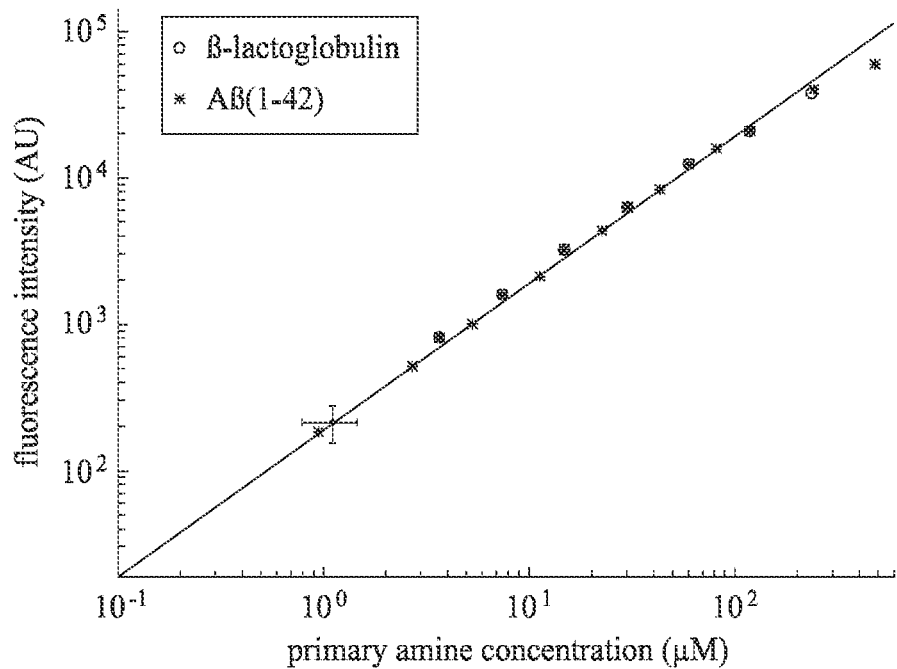
FIG. 3A shows the linear relationship between primary amine concentration and OPA fluorescence intensity, established for a dilution series of β-lactoglobulin of known concentration, which in turn is used to determine the primary amine concentration in an Aβ(1-42) dilution series of unknown concentration.
Figure 3B:
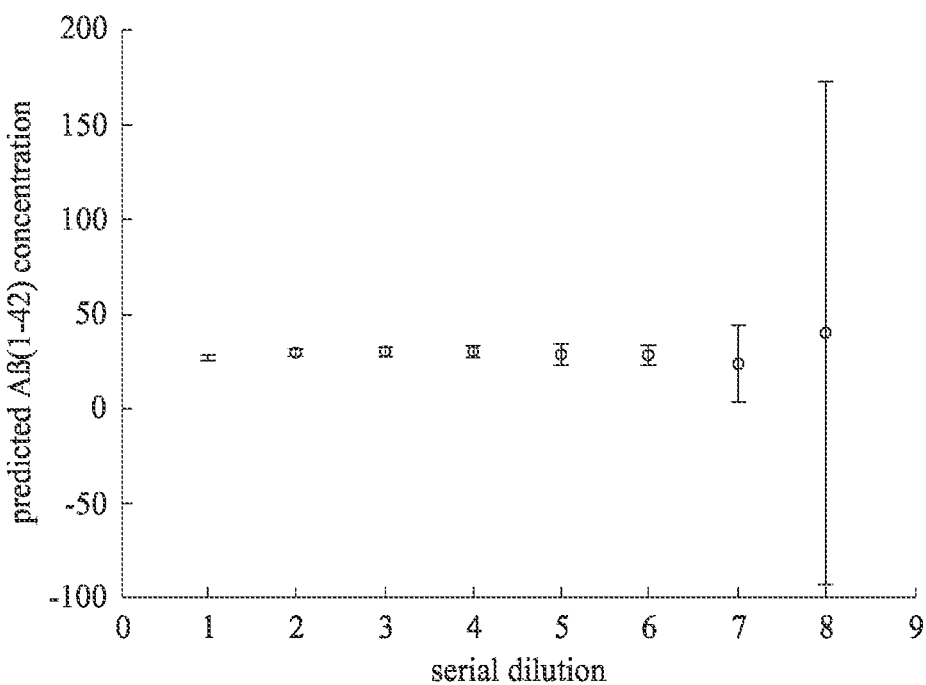
FIG. 3B the conversion of the intensity data to protein concentration accounting for the dilution of each β-lactoglobulin sample in the series, thereby yielding a consistent calculated peptide concentration of around 27 μM.

FIG. 3 shows how the quantitative labelling method presented here can be used to determine the concentration of purified Aβ(1-42) peptide. In FIG. 3A, the linear relationship between primary amine concentration and OPA fluorescence intensity is determined by measuring fluorescence intensity for known concentrations of β-lactoglobulin. Importantly, because the labelling reaction is quantitative, this relationship only needs to be determined once for a given set of measurement conditions.

Fluorescence intensity is measured for unknown concentrations of Aβ(1-42) using the same experimental conditions. In both cases error bars are the standard deviation of three replicates. Because of the linear relationship between protein primary amine concentration and OPA fluorescence intensity, Aβ(1-42) primary amine concentration is thus determined from the observed fluorescence intensity. Panel B shows the corresponding protein concentration determined for each serial dilution, after correcting for the dilution factor. A stable value of approximately 27 µM is obtained across the concentration series. This 35 method can be used in order to rapidly and accurately determine Aβ(1-42) and Aβ(1-40) concentration prior to further biophysical studies. Further, an analogous method can be used to determine the concentration of any protein in a fluid flow, provided that the primary amino acid sequence is known.

Figure 4:
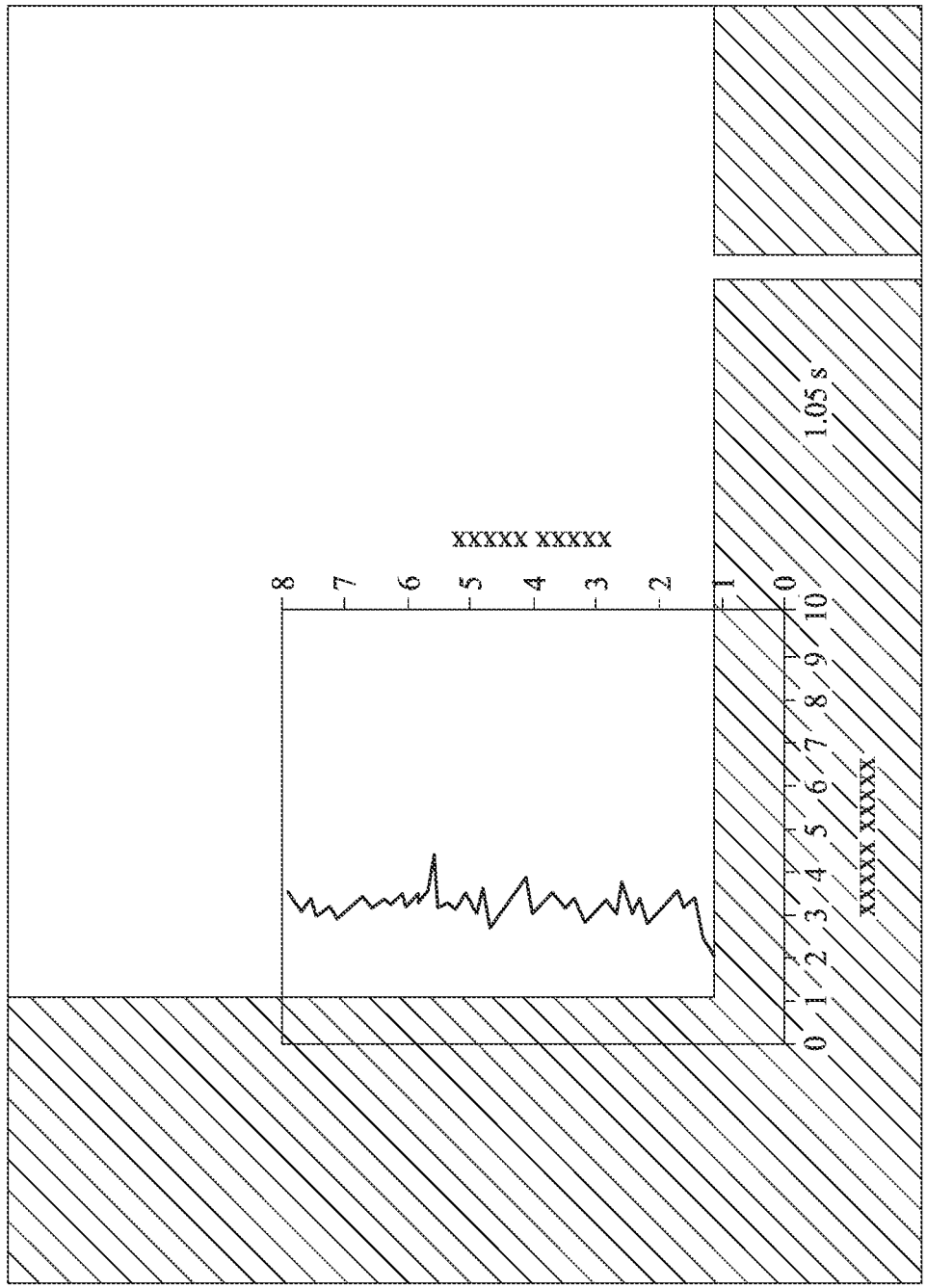
FIG. 4 shows 10 mg/mL BSA was loaded into both inlets of a diffusion device, such as shown in FIG. 6 and FIG. 7A. The flows were permitted to contact in the separation channel, and a portion of the laminar flow collected. The diverted flow is contact with a labelling flow, and this combined flow moves through a mixing loop (for ca. 1.05 s), as shown by the sinuous channel path in FIG. 6 and FIG. 7A. By the time that the sample exits the mixing loop, fluorescence intensity is constant. A representative trace is overlaid, although fluorescence intensity remained constant along the length of the device. This indicates that labelling is complete within the ca. 1 s mixing time.

The ability to quantitatively label components on a fast timescale in a microfluidic experiment was demonstrated. There are few reports of OPA reaction kinetics in the literature (Yoshimura et al. *Anal. Biochem.* 164, 132-137 (1987); Wong et al. *J. Am. Chem. Soc.* 107, 6421-6422 (1985)) and no reports of the rate of modification of full length proteins, or the rate of OPA reactivity in the presence of a denaturant. Using the device shown in FIG. 7A, it was found that the use of the SDS-containing denaturing conditions identified above, BSA modification proceeded to completion in approximately 1 s; fluorescence intensity was constant after protein and the quantitative latent covalent labelling solution had mixed in, and exited the waiting loop. A representative image is shown in FIG. 4, where the constancy of fluorescence intensity is illustrated with an intensity profile.

Described above is a novel quantitative latent covalent labelling approach which allows components to be quantitatively labelled with a fluorogenic dye following lateral separation and diversion in a fluidic device. Because the labelling is quantitative, protein concentration can be directly determined from fluorescence intensity. This approach separates the measurement and detection processes such that the presence of the label does not affect the measurement and analysis. Discussed below is the application of this labelling to methods of separation and detection using electrophoretic and diffusional separations.

Diffusional Separation

When fluids are confined to the millimetre length scale, flows are laminar, rather than convective. Accordingly, when two adjacent streams of fluid meet, such as in a Y- or T-junction, the only mixing between the layers of fluid is due to diffusion (Whitesides *Nature* 442, 368-373 (2006); Squires et al. *Reviews of Modern Physics* 77, 977-1026 (2005)). The diffusion coefficient and hydrodynamic radius of the species of interest is therefore accessible from its spatial distribution. Described herein is a device for the derivitsation and quantification of diffusionally separated species. A representative diffusional device is shown in FIG. 1A. The device has two flow inlets. Looking at FIG. 1, buffer is loaded into one inlet (bottom left), and protein into another inlet (top left). Only protein that diffuses into the buffer flow can be diverted and labelled. After traveling along the length of the diffusion channel, protein that has diffused at least 33 µm into the buffer flow from the laminar boundary between buffer and protein flows is sequestered (diverted) and subsequently mixed with a labelling mixture within the fluidic device. The labelling mixture contains a label (unless otherwise noted, OPA) and a denaturant (unless otherwise noted, SDS).

Fluorescence intensity of the labelled protein is measured in the rectangular observation region. Unlabelled protein is also solubilized, so that it does not form insoluble aggregates, for example as if it passes through the protein isoelectric point when it combines with the alkaline labelled solution.

The extraction of accurate hydrodynamic radii—particularly for heterogeneous mixtures of components—requires comparison of experimental data to simulated spatial diffusion profiles generated for components of known size. Such comparisons are described herein, and with reference to PCT/GB2013/052757.

Insulin

As an initial demonstration of diffusional methods, the depletion of monomer and small oligomers in an insulin aggregation reaction was studied. The effect of pH-induced changes in insulin hexamerization was also studied. Insulin was one of the first systems observed to form amyloid fibrils in vitro (Waugh *J. Am. Chem. Soc.* 68, 247-250 (1946)). Insulin has served as a convenient biophysical model system for oligomerization and amyloid aggregation. Insulin forms well defined dimers, tetramers, and hexamers with changes in pH (Nettleton, E. J. et al. *Biophysical Journal* 79, 1053-1065 (2000); Whittingham et al. *Journal of Molecular Biology* 318, 479-490 (2002)).

The protofilament structure of its amyloid fibrils has been determined by cryo electron microscopy (Jimenez et al. *Molecular basis for insulin fibril assembly PNAS* 99, 9196-9201 (2002)), and the structure of a central segment crucial to the cross-spine by X-ray crystallography (Ivanova et al. *PNAS* (2009)). Recent work (Knowles et al. *Science* 326, 1533-1537 (2009); Cohen et al. *Journal of Molecular Biology* 421, 160-171 (2012)) allows the extraction of microscopic rate constants reflecting discrete steps in the aggregation process from ThT fluorescence data which indirectly monitors (LeVine et al. *Protein Science* 2, 404-410 (1993); Biancalana et al. *Biochimica et Biophysica Acta* 1804, 1405-1412 (2010)) the formation of mature amyloid fibrils. Existing experimental methods for directly following the changing populations of monomer and small oligomers in amyloid aggregation reactions perturb the transient processes under observation, through either transfer into the gas phase (Nettleton, E. J. et al. *Biophysical Journal* 79, 1053-1065 (2000)), exogenous labelling and dilution (73), or long measurement times (Schuck *Anal. Biochem.* 320, 104-124 (2003); Mok et al. *Methods* 54, 67-75 (2011)).

The diffusional separation and detection method described herein is the first direct experimental method capable of non-disruptively following monomer and small oligomer depletion.

Figure 7B:
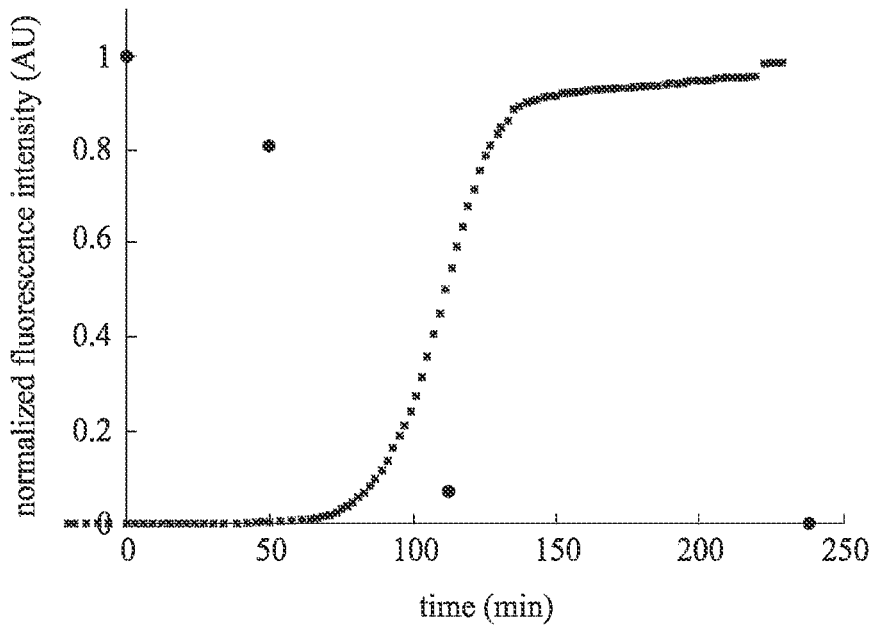

Insulin aggregation was initiated by incubating 2 mg/mL bovine insulin at 60° C. under quiescent conditions. As shown in FIG. 7B, the process of fibrilisation was monitored in real time via an increase in ThT fluorescence. Aliquots from samples without added ThT were removed at time points which corresponded to the unheated monomer at t=0, the first detectable increase in ThT fluorescence, the lag time, and the equilibrium phase.

The aliquots were loaded into the protein inlet of the diffusion device shown in FIG. 7A.

The smallest species from the separation channel were diverted to the detection zone. After diversion, the diverted flow was first mixed with a latent labelling mixture (12 mM OPA, 18 mM BME, 4% SDS, 200 mM carbonate pH 10.3). The labelled insulin species were then detected by fluorescent spectroscopy.

FIG. 7B overlays the normalized fluorescence intensity values for these time points with the corresponding fibrilisation curve. This is believed to be the first non-perturbative direct experimental analysis of the depletion of monomer and small oligomers in an amyloid aggregation reaction.

The separation and analysis methods of the invention have also been used to study pH-induced insulin oligomerization. At low pH, insulin exists primarily as a dimer (61). At neutral and alkaline pH, in the presence of $Zn^{2+}$, insulin exists as a hexamer (76). Accordingly, 2 mg/mL solutions of bovine insulin were prepared at pH 2.0 and 10.5. These solutions were loaded into the upper protein inlet of the device shown in FIG. 1A. Species which diffused 33.33 μm or more were then diverted, and subsequently labelled and the fluorescence intensity of the flow was measured. The insulin was labelled with the OPA labelling mixture used above. The separation, diversion, labelling and detection steps were all performed on a single device under steady state flow conditions.

Figure 7C:
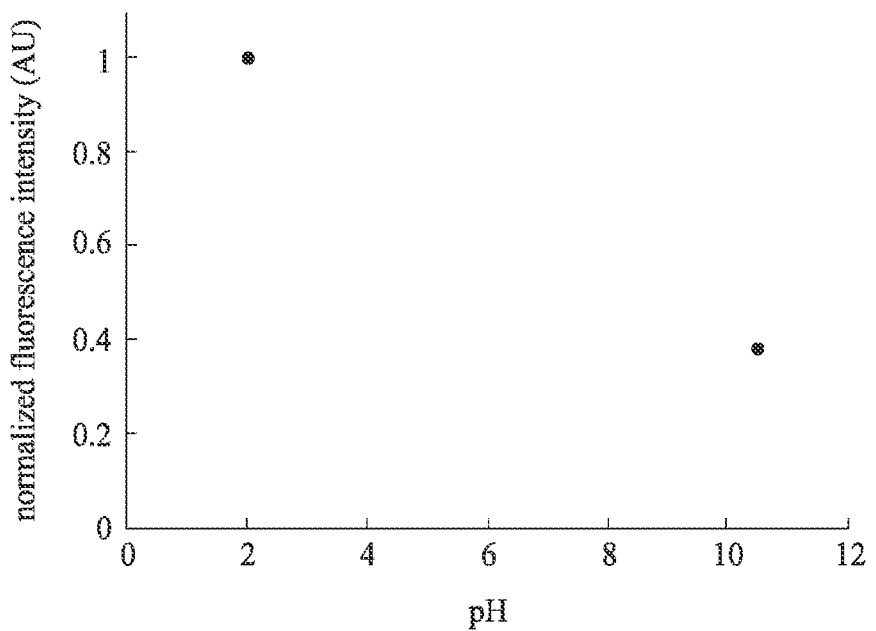

The fluorescence intensities observed at pH 2 and pH 10.5 are plotted in FIG. 7C. It is tempting to speculate that the lower relative fluorescence intensity at alkaline pH corresponds to the insulin hexamer.

Absolute Hydrodynamic Radii

The data recorded in FIG. 7B and FIG. 7C uses differences in relative fluorescence intensity to indicate varying proportions of small species, which diffuse far enough to be labelled. Though these data do yield qualitative information about relative differences between a sample set, it is additionally possible to use diffusion-based separation and detection methods to obtain absolute hydrodynamic radii, by adapting a known numerical simulation algorithm as part of diffusion spectrometry (see PCT/GB2013/052757).

The simulation generates expected particle density profiles—termed "basis functions"—for spherical particles of known hydrodynamic radius. This simulation randomly distributes particles of a known size across a "nozzle" with an initial distribution corresponding to a theoretically predicted and experimentally observed "hat" function. The particles are allowed to propagate through the diffusion channel, taking Brownian motion random steps that account for the non-uniform velocity profile throughout the channel (Lauga et al. URL http://arxiv.org/abs/cond-mat/0501557), and eventually reach a detection zone.

The steady-state distribution of particles of that size is then simulated by summing the distributions obtained for every time point before every particle reaches the observation region. In diffusion spectrometry these basis functions are then used to assess the relative contributions of particles of known sizes to the experimentally observed spatial diffusion profiles through a least square fitting algorithm. There are two related issues to be considered in the application of this known approach to the methods described herein. Spatial diffusion profiles are not typically measured in the separation zone. The reason for this is that components are likely to be unlabelled, and are therefore not easily detectable. In some embodiments of the invention the components may be detectable and therefore diffusion profiles may be measured during the separation step, for example in the separation channel.

Where the diffusion profile cannot be measured during the separation step, the component is analysed later after diversion. For example, diverted component may be fluorescently labelled after diversion and the experimental observable is the integrated fluorescence intensity within the detection zone. Because the labelling step is quantitative, it is possible to relate integrated fluorescence intensity to component concentration within the observation zone. Then, once a calibration curve has been constructed for the settings used, a hydrodynamic radius can theoretically be obtained by relating that apparent component concentration to the known loaded component concentration (provided that only a single component has been loaded). The experimentally observed ratio can then be compared to similar particle density ratios derived from simulations where particles of known hydrodynamic radii are allowed to diffuse throughout the separation channel.

Figure 6:
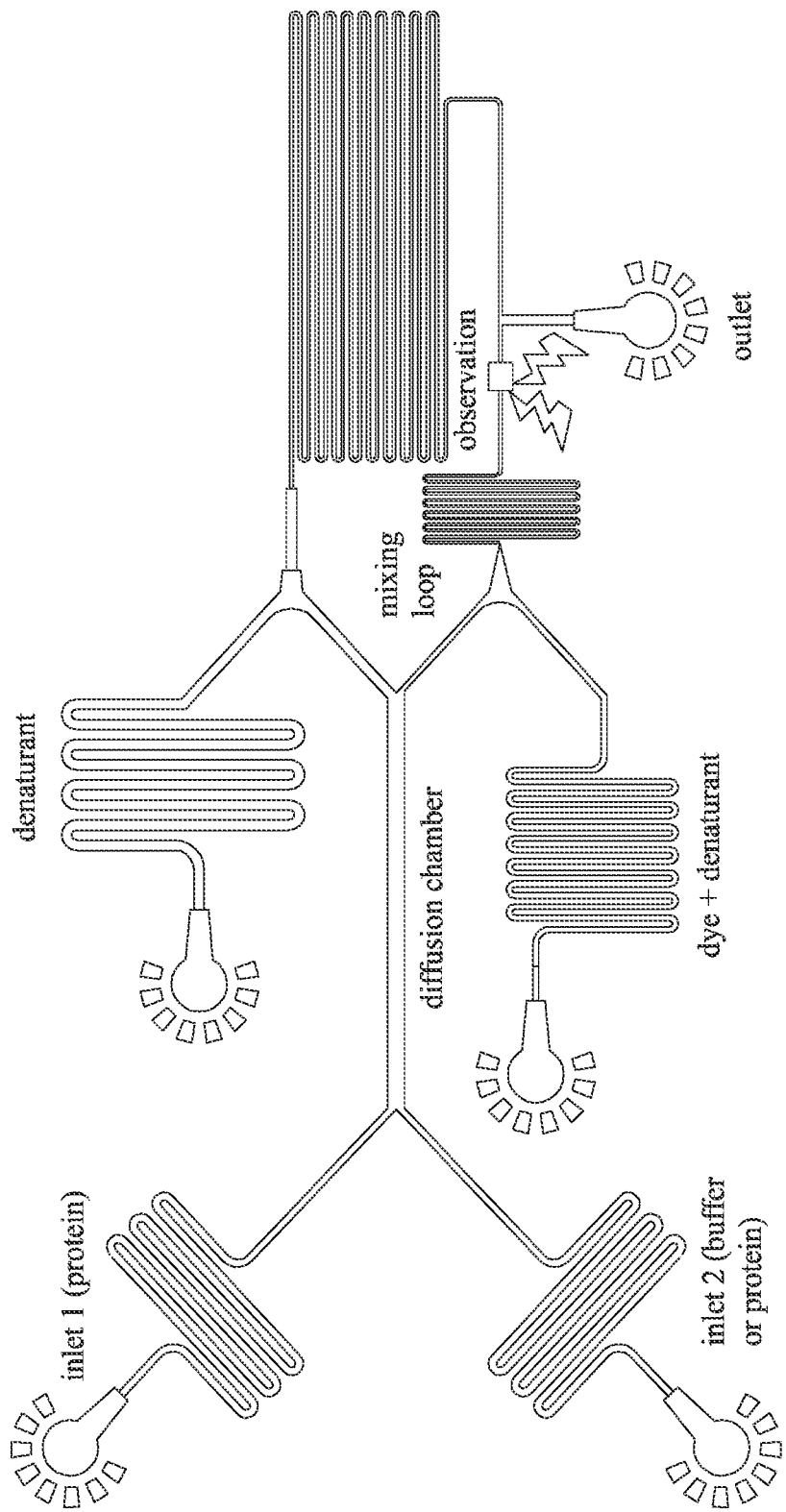
FIG. 6 shows a schematic of a diffusion microfluidic device according to an embodiment of the invention.

Relying on absolute fluorescence intensities, however, is experimentally problematic, as the absolute fluorescence intensity and thus apparent concentration obtained will vary depending upon imaging settings, and practically even on precise differences in optic alignment. Such variability can be eliminated by instead internally correcting for these factors by including an additional experimental and theoretical data point: the fluorescence intensity (or particle density) observed when component is loaded into both inlets, as shown in FIG. 6. The ratio of these values gives the proportion of the total loaded component concentration that has diffused far enough to be labelled, which can be compared to corresponding simulation results to yield an exact value for the sample hydrodynamic radius.

Figure 8:
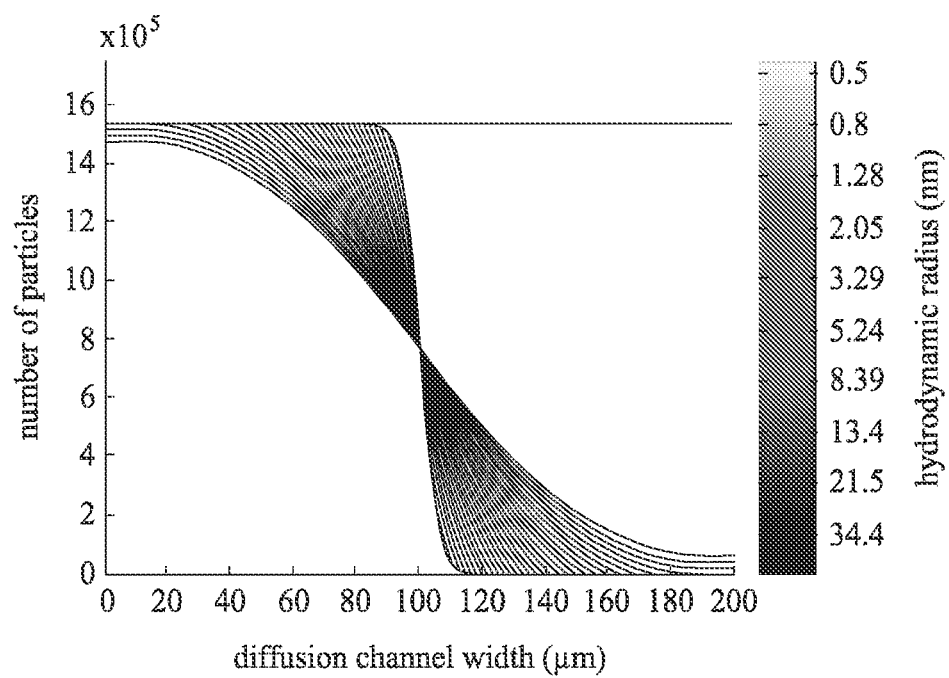
FIG. 8 shows the simulated number of particles across a diffusion channel for particles having different hydrodynamic radii. In the simulation, particles of known hydrodynamic radii were loaded into one or both inlets of a diffusion device like the one shown in FIG. 6. The simulation strategy is described in the text, and the simulation results correspond to the steady-state particle intensity distribution at the end of the diffusion channel as a function of horizontal distance across the channel. Hydrodynamic radii are indicated colorometrically. When particles are loaded into both inlets, their steady state distributions do not change as a function of hydrodynamic radius (dark horizontal line in the figure), but they vary predictably with hydrodynamic radius when particles are loaded into one inlet (evolving hat function).
Figure 9:
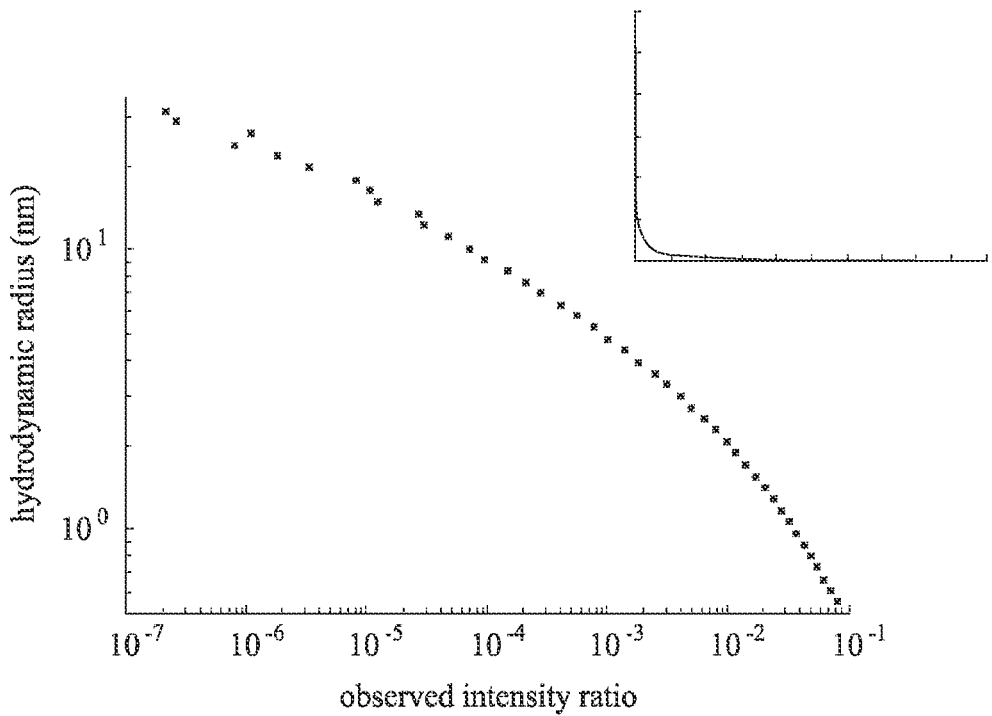
FIG. 9 shows the correlation between hydrodynamic radius (nm) and observed intensity ratio for particles that have diffused by at least 33 μm in the separation channel of the device of FIG. 6. Thus, the diversion step captures those components having the smallest hydrodynamic radius (and are therefore diffuse most rapidly towards the second flow boundary at the channel wall). The inset graph is a replot with the intensity ratio and hydrodynamic radius in natural (non-logarithmic) scale.

The results of these simulations are shown in FIG. 8 and FIG. 9. In FIG. 8, the diffusion of particles with known hydrodynamic radii was simulated. The hydrodynamic radii were logarithmically spaced between 0.5 and 50.0 nm, a size regime relevant to the detection of species ranging in size between small molecules and large protein complexes or aggregates.

The steady state distribution of components at the end of the diffusion channel was simulated (after which species of interest are diverted and for optional labelling, and subsequent analysis). The simulation was based on a system where particles are loaded into one device inlet and the situation where the particles are loaded into both device inlets, as shown in FIG. 6. The results of these simulations are color-coded according to hydrodynamic radii and shown in FIG. 9. As expected, the steady-state distribution of particles does not change as a function of hydrodynamic radius where a component (here, a protein) is provided in both fluid inlets: the uniformity of the initial condition diffusion leads to no net change in the particle distribution at steady-state. In contrast, for the situation where component is provided in only one (the top inlet in FIG. 6), the steady-state distribution at the detection zone varies predictably with hydrodynamic radius.

Based on the device design shown in FIG. 6, species have to diffuse at least 33 µm in order to be diverted by the downstream flow separator. After diversion the component mixes with the labelling solution in a waiting loop, and the labelled component is then detected by fluorescence methods. Accordingly, the proportion of species which have diffused far enough to be labelled are those which at the end of the separation channel and at steady state are located between 133 and 200 µm along the width of the channel, taking 0 µm as the far wall of the protein inlet.

In order to capture this proportion, the corresponding region of the particle distribution profiles, for the conditions where component is provided in both inlets, was integrated. The ratio of these intensities gives the proportion of the total loaded component concentration that has diffused far enough to be diverted for each of the known hydrodynamic radii. By comparing experimentally observed ratios to simulated ones, an absolute sample hydrodynamic radius can be obtained.

In FIG. 9, the dependence of hydrodynamic radii on experimentally observed diffusion ratio is demonstrated. The main figure is shown in double logarithmic format, and the inset is shown in linear format. The largest four hydrodynamic radii give diffusion ratios (to a numerical approximation) of 0, so these points are removed from the logarithmic plot. To a first order approximation, the data can be reasonably well fitted to a power-law:

$$f(x) = ax^b$$

with a=1.13 and b=0.22, with an $R^2$ of 0.97, and the predictability of the simulation results demonstrate how experimentally observed diffusion ratios can be unambiguously related to hydrodynamic radii.

Unless the analyzed sample is monodisperse, however, the technique above is expected to yield an average hydrodynamic radius. Hydrodynamic radii from multiple components of complex protein mixtures may be obtained through expanding the series of experimental conditions for which species diffusion is modelled. As shown in FIG. 10A, variants of 40 the fluidic device which select and quantitatively label multiple portions of the diffusing sample have been designed. Here, the flow from the separation channel is separated (diverted) into three equal components.

Region 1 corresponds to the component that have diffused the furthest (at least 33 µm) from the component flow. Region 2 collects the central third of components, and Region 3 the final third, or the components which are in steady state at the end of the diffusion chamber within 66 µm of the far component wall. Each diverted flow is, in this configuration, separately denatured, and then the denatured components in the flow are labelled with the OPA-containing mixture.

FIG. 1013 illustrates the dependence of reference sample hydrodynamic radius on diffusion ratios 1, 2, and 3. The diffusion ratios were calculated as above. By extending the theoretical treatment to cover a variety of flow rates (the basis functions shown here correspond to a single withdrawal rate of 37.5 µL/hr in the diffusion channel), it is possible to plot, for each hydrodynamic radius, the dependence of diffusion ratios, 1, 2, and 3, on flow rate. The relative contributions of these basis curves to the observed experimental data will be determined with a least-squares fitting procedure. This yields a list of hydrodynamic radii within the heterogeneous sample of interest. Because the labelling reaction is quantitative, the relative abundance of each hydrodynamic radius within the experimental sample can be determined.

Solubility

Figure 11:
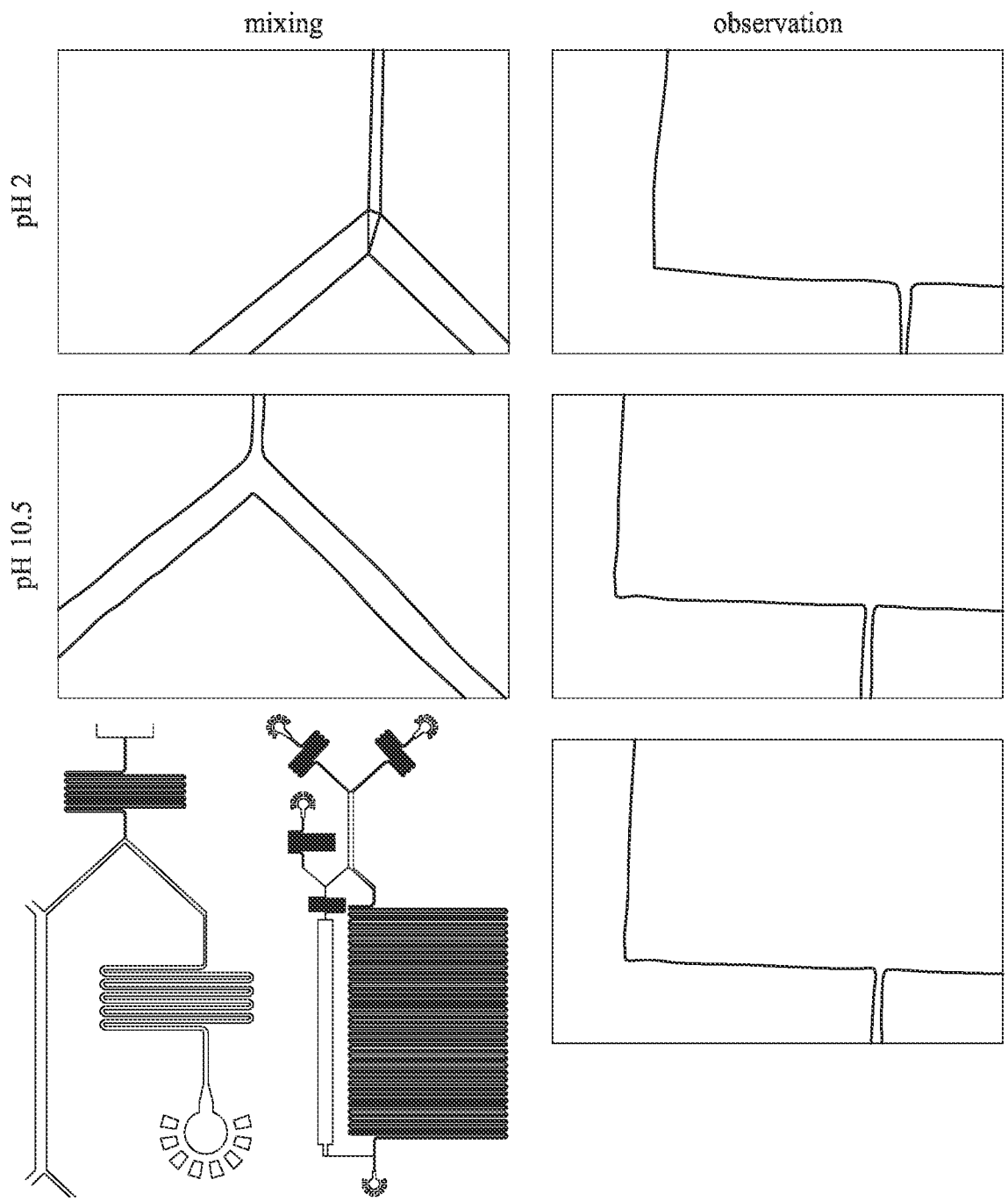
FIG. 11 shows the raw images which correspond to the pH-induced insulin hexamerization data displayed in FIG. 7C. They have been annotated according to pH and type. The pH 2 image shows how when the pH 2 insulin contacts the high ionic strength pH 10.5 labelling solution, protein crashes out and is deposited at the laminar flow interface between the two streams of fluid. Though ultimately solubilized again downstream, the deposition of this protein can cause flow-rate variation.

The preliminary insulin aggregation and hexamerization data presented here is qualitative, and it does no relate changes in intensity to direct changes in sample hydrodynamic radii. The reason for this is related to a solubility issue that causes irregular deviations of the flow-rate from the selected value. If a flow containing a component is altered, e.g. during the labelling of the component, such that the isoelectric point is passed, then the component "crashes out" at the laminar flow interface where the component and the labelling mixture meet. Representative images corresponding to the pH-induced insulin hexamerization experiment shown in Panel C of FIG. 7 are shown in FIG. 11. The plug of aggregated protein is ultimately solubilized, but the presence of precipitated protein at the mixing region between the two streams blocks the flow and causes unpredictable flow-rate changes, which given the sensitivity of the diffusion profiles to flow-rate, would make extraction of quantitative hydrodynamic radii from the relative fluorescence intensity changes problematic.

This problem is not unique to insulin and the same problem has been observed for a variety of systems when the protein of interest passes through its isoelectric point upon labelling.

In order to present a truly general method for quantitative separation and detection methods that will work with any protein system of interest, the solubility issues have been addressed in a variety of ways.

When an insulin labelling reaction is repeated in bulk no insoluble species are formed. For example, insulin at pH 2 was rapidly mixed with an equal volume of 12 mM OPA, 18 mM BME, and 4% SDS in 200 mM bicarbonate, pH 10.5, and the pH of the resulting solution was 10.5.

Accordingly, the solution is effectively buffered to a pH where monomeric insulin is soluble in isolation, and complete mixing does result in a soluble mixture. This indicates that insulin is protected against aggregation near the pH when it is effectively solubilized with a denaturant. It is hypothesized that solutions of this type were crashing out at the laminar flow interface because the pH of the protein solution at the interface would be changed before the protein was able to bind detergent micelles, simply because of the differences in $H^+$ concentrations and micelle diffusion coefficients.

Note, when the insulin solution is left at room temperature, precipitation is observed on a timescale of days, although this timescale is irrelevant to that of a fluid flow labelling experiment.

Figure 12A:
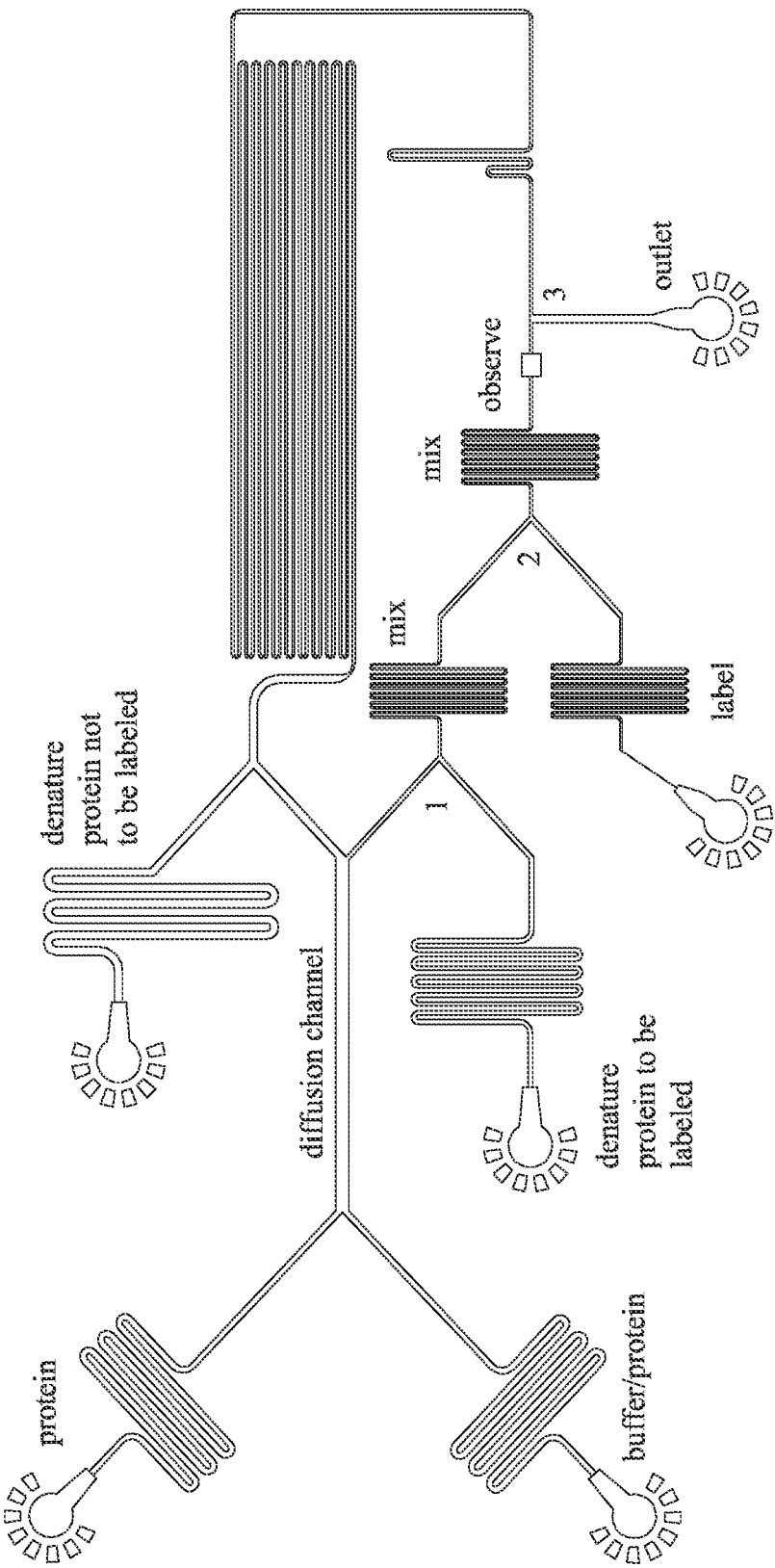
FIG. 12A shows a schematic of a diffusion microfluidic device according to an embodiment of the invention.

Accordingly, a method was developed that included separate denaturation and labelling steps. The device for use in that method is shown in as shown in FIG. 12A. After diversion, a component, such as protein, to be labelled was first completely mixed with a denaturant then subsequently mixed with a labelling mixture. Additionally, unlabelled component present in the undiverted flow was mixed with the denaturant to prevent the component from precipitating when it is subsequently recombined with the diverted flow near the device outlet.

Figure 12B:
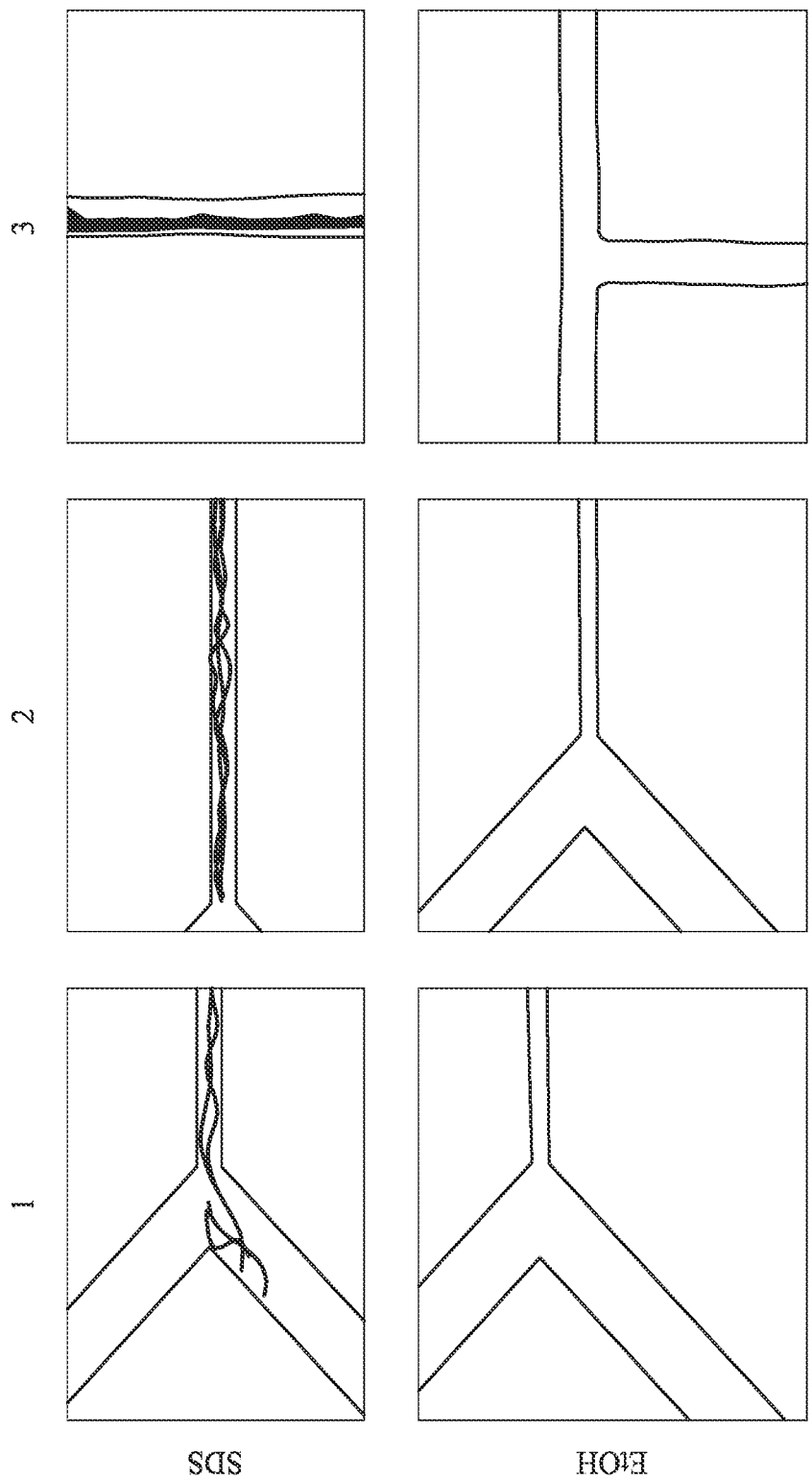
FIG. 12B images of the channels at points 1, 2 and 3 of FIG. 12A for the solvents SDS (top panels) and EtOH (bottom panels)

FIG. 12B shows the results when 9.1 mg/mL insulin at pH 2 is mixed on-chip with two separate denaturing and labelling solutions. Interface 1 corresponds to the mixing of the unlabelled protein and the denaturant, interface 2 to the denatured protein and the labelling mixture, and interface 3 to the mixing of the unlabelled protein (which has also been previously mixed with the denaturant) and the labelled and denatured protein mixture. When SDS is used as the denaturant prior to the labelling step, gross aggregate formation at the laminar flow interfaces is observed, which is much more significant than the temporary blockage formed when SDS denaturation and labelling proceeded in a single step. Though 35 SDS is traditionally thought to solubilize all proteins, it can also electrostatically interact with positively charged residues, such as lysine and arginine, forming a hydrophobic ion pair. This effect is particularly relevant for proteins below their isoelectric points, and insulin-SDS interactions which diminish insulin aqueous solubility have been specifically reported (Powers et al. *Biopolymers* 33, 92-932 (1993)).

A variety of other ionic and nonionic surfactants (such as Tween-20 and Triton-X) were considered together with varying protein denaturation mechanisms (Otzen *Biochim. Biophys. Acta.* 1814, 562-591 (2011); Otzen *Biophys. J.* 83, 2219-2230 (2002)), alkaline and alkaline earth salts (Ahmad *Can J. Biochem. Cell Biol.* 63, 1058-1063 (1985)), and organic solvents which have been reported to denature proteins (Brandts et al. *J. Am. Chem. Soc.* 89, 4826-4838 (1967); Hirota et al. *Protein Science* 6, 416-421 (1997)), and combinations thereof (Flockhart et al. *Journal of Colloid Science* 12, 557-565 (1957)), for their ability to both solubilize proteins during the analysis step. The survey of surfactant and denaturant space has revealed that there are a variety of conditions which ensure quantitative labelling including, for example, mixtures of organic solvents such as EtOH and SDS yield data similar to that shown in FIG. 2. Only one condition has been shown to reliably solubilize protein passing through the isoelectric point in the flow, however: an equal volume fraction of protein and 100% EtOH prior to labelling.

Figure 12C:
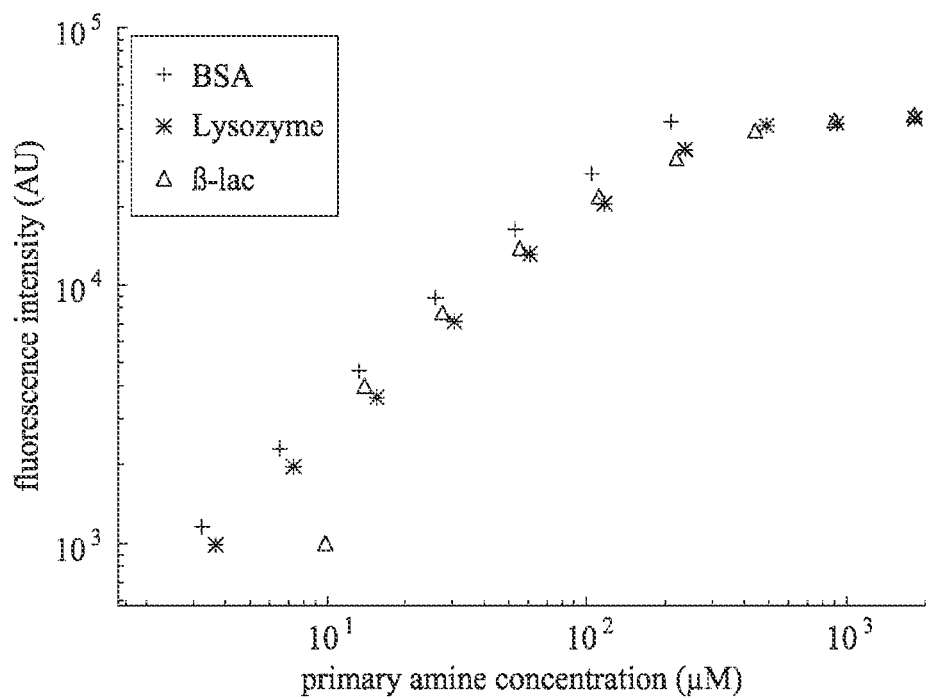
FIG. 12C a plot of fluorescent intensity with change in primary amine concentration for BSA, lysozyme and β-lac for labelling with EtOH solvent, showing that EtOH does not solubilize, or quantitatively label, all proteins.

The improved solubility observed with this condition is shown in FIG. 12B. As shown in FIG. 12C, this condition does not result in quantitative labelling. A strong linear correlation between primary amine concentration and fluorescence intensity is not observed, and the lysozyme solutions becomes turbid in the bulk labelling experiment, which indicates that in addition to incomplete labelling, the solubility that the EtOH mixture confers on low isoelectric point proteins examined is not general.

Finally, spatially practical fabrication of diffusion devices incorporating separate denaturing steps requires the use of several stretches of very long, narrow channels which act as waiting loops where diffusional mixing takes place. The dimensions of these channels (on the order of 20 μm wide, 25 μm high, and 30 mm long) can be difficult to fabricate and are to microbubble formation in use, for example when due to unfavourable wetting properties during filling (Monahan et al. *Analytical Chemistry* 73, 3193-3197 (2001)). The presence of microbubbles severely affects the flow rates attained. Due to the sub-atmospheric pressures within the channel, microbubbles grow at the expense of solution flow through the device, causing variable low rates (Kang et al. *Lab on a Chip* 8, 176-178 (2008)).

Figure 12D:
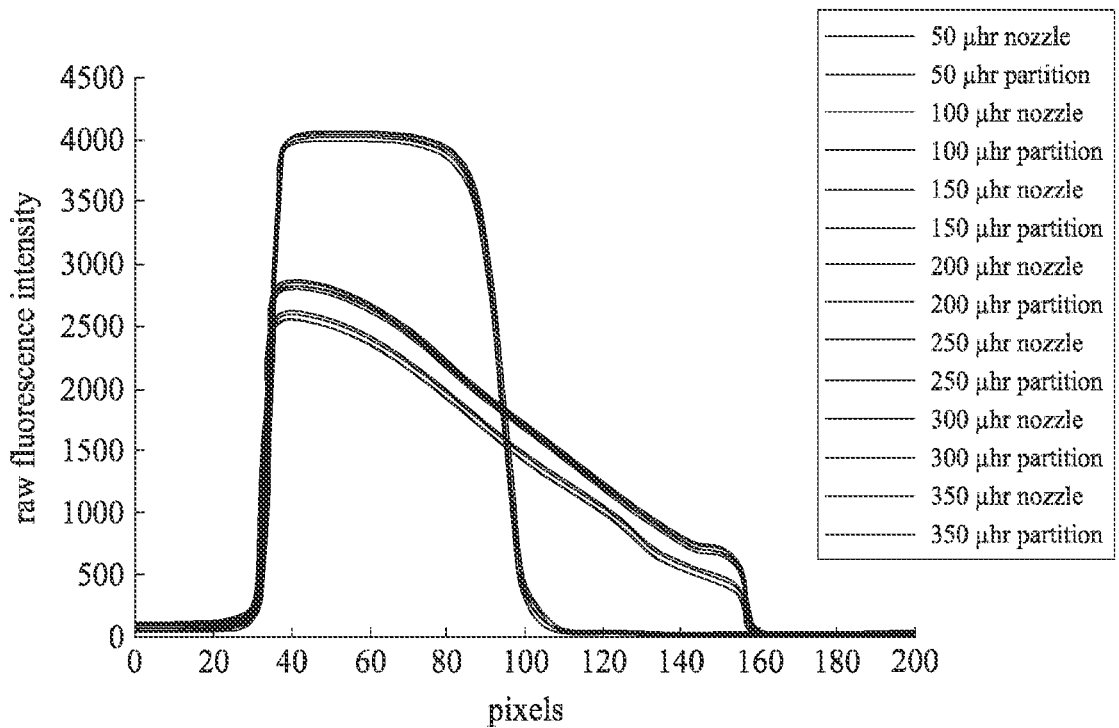
FIG. 12D a plot of fluorescent intensity with change in pixel location for a range of different flow rates as recorded at the nozzle and partition points in FIG. 12A, showing the unpredictable flow with the diffusion channel.

After initial efforts at obtaining absolute hydrodynamic radii for model proteins (as described above) using the separate denaturing device shown in FIG. 12A yielded unphysical diffusion ratios, diffusion profiles for an intrinsically fluorescent small molecule of known size (fluorescein) were studied at a range of flow rates. FIG. 12D shows that, as expected, the "hat function" initial distributions at the junction were as expected, but that the diffusion profiles did not change predictably as a function of flow rate. It is therefore concluded that unpredictable flow rates within the diffusion channel—likely caused by the presence of microbubbles within devices of this complexity—results in the deviation from the predicted diffusion ratios.

In summary, FIG. 12 demonstrates that a set of (extensively surveyed) chemical conditions does not exist that satisfies both the chemical requirements of component, particularly protein, solubilization and denaturation, and the physical requirement of predictable operation, without sacrificing other factors such as detection sensitivity. Time course studies (not shown here) demonstrate that protein which crashes out at the laminar flow interface is ultimately resolubilized. Hence in the absence of conditions associated with permanent diminished aqueous solubility like the separate denaturing conditions shown in FIG. 12B, the problem is not a true lack of solubility but the variable flow rates observed when temporarily aggregated protein blocks the flow at the mixing junction.

After having explored a variety of mixing junction geometries (data not shown) and having found no change in clogging behaviour, the effect is believed to be due to a more fundamental property of microfluidic fluid behaviour. The no-slip boundary condition results in zero velocity at the channel edges and a varying velocity distribution throughout the channel (Lauga et al. URL http://arxiv.orgiabsicond-mat/ 0501557). It is believed that insoluble protein at the laminar flow interface, before diffusional mixing has occurred, sediments in the regions of low velocity, clogging the device.

In order to test this hypothesis and ideally alleviate the solubility issues described above, the present inventors are currently developing 3-dimensional separation and detection devices, in which the component will be vertically flanked by sheaths of dye and denaturant, such that there is no region of low velocity at the laminar flow interface. Additionally microfluidic devices with active mixing components are under investigation, such as rotating magnetic beads or particles (Stone et al. *Annual Review of Fluid Mechanics* 36, 381-411 (2004); Rida et al. *Analytical Chemistry* 76, 6239-6246 (2004); Lee et al. *Lab on a Chip* 9, 479-482 (2009)), in order to quickly solubilize the protein following initial contact, and disrupt any sedimentation that may occur.

The device and method of the invention allow for the separation of components based on their electrophoretic and diffusional properties, and the subsequent detection of those components, optionally together with a labelling step.

Where diffusion is used as the separation method, it is possible to extract absolute hydrodynamic radii by relating experimental "diffusion ratios" with similar ratios simulated for species of known hydrodynamic radius, and to extend the analysis to heterogeneous mixtures of species by extracting diffusion ratios for multiple "bins" of diffusing species over multiple flow rates, and comparing these to simulated results for species of known hydrodynamic radii.

The device and method of the invention provide a general technology which can be used for the non-perturbative detection and concentration determination of any protein species of interest, regardless of solution conditions and isoelectric point.

Hydrophilic Channels

The use of hydrophilic channels in a fluidic device was investigated as part of labelling study. A fluidic device was prepared having a convergent mixing channel that was supplied by upstream first and second supply channels (see FIG. 15D). The channels in the device were standard PDMS channels that were plasma treated to produce hydrophilic silanol groups on the channel surfaces. The channels are then filled with water, resulting in the maintenance of the hydrophilic surface for several days. The plasma treatment step was performed on the freshly bonded microfluidic device.

The first supply channel supplied component (insulin) in a liquid flow and the second supply channel provided label (an OPA mixture) in a liquid flow. The fluids from the first and second channels were permitted to contact at a junction at the upstream end of convergent mixing channel (see brightfield FIG. 15B. The fluids converged (see brightfield image FIG. 15B and fluorescence FIG. 15E) and were later analysed within a detection zone (see brightfield image FIG. 15C and fluorescence FIG. 15F).

The insulin-containing fluid contained 10 mg/mL of insulin at pH 2. The labelling fluid contained 12 mM OPA, 18 mM BME, 4% SDS, and 200 mM carbonate at pH 10.5.

FIG. 15A, FIG. 15B and FIG. C show that although an interface is clearly visible (expected for solutions of different viscosity), insulin does not stick to the treated PDMS channels and instead dissolves downstream. This is the case even though a high concentration insulin fluid is used in the device. In this case it is to be expected that some insoluble protein is present at the laminar flow interface as that protein that is passing through its isoelectric point. Insoluble protein does not stick to the PDMS channels and instead dissolves downstream.

The images here are in contrast to the insoluble materials that are visible in the images of FIG. 11 and FIG. 12B.

FIG. 15G shows that a substantially stable flow is generated in the device of FIG. 15D. This is due to the minimisation of blockages and the prevention of microbubble formation (owing to better wetting).

The use of hydrophilic channels is believed to eliminate the need for a separate denaturation Step in the methods of the invention. Protein which is temporarily insoluble before complete mixing will not stick to the channel walls and will be solubilised later downstream.

Electrophoretic Separation Electrophoresis is a common biological technique for separation of nucleic acids, peptides, and cells. Gel electrophoresis, in which analyte charge-to-size ratio is assessed via retardation in a solid matrix upon the application of an electric field, is the most common technique, though this is not well suited for the study of weak protein association events as the act of matrix sieving itself can disrupt interactions. Capillary Electrophoresis (CE) involves the temporal separation of analytes based on their differential electrophoretic mobility and electroosmotic flow throughout a channel. In Free-Flow Electrophoresis (FFE), the sample moves throughout a planar channel through pressure-driven flow, and separation upon application of an electric field is perpendicular to the direction of flow. Because FFE is a steady-state technique, injection and separation are performed continuously. Microfluidic Free-Flow Electrophoresis (µFFE), a microfluidic miniaturization of FFE, has the advantage of improving separation resolution by reducing the effect of Joule heating, and facile on-line integration with other separation techniques (Turgeon et al. *Micro free-flow electrophoresis: theory and applications* 394, 187-198 (2009). URL http:// dx.doi.org/10.1007/s00216-009-2656-5).

One of the limitations of µFFE has historically been the integration of electrodes within microfluidic devices, with challenging multi-step processes necessary to ensure direct contact between the electrodes and conductive aqueous media (Kohlheyer et al. *Lab on a Chip* 6, 374-380 (2006); Cheng et al. *Lab on a Chip* 11, 2316-2318 (2011)). Recently, some of the present inventors have developed a microfluidic device having electrodes placed alongside a channel, and suitable for electrophoresis (Herling, T. W. et al.).

Herling et al. describe the incorporation of 3-dimensional electrodes into a microfluidic device in a single photolithography step, and the authors have used the microfluidic device to quantify the net-solvated charge of small molecules (Herling, T. W. et al. *Applied Physics Letters* 102, 184102-4 (2013)). In the initial work, however, fluorescent dyes were used in order to permit detection. Application of this technique to the separation of biomolecules requires the use of biomolecules which have been fluorescently labelled. The presence of an exogenous fluorescent label, which affects molecular size, charge, and interactions, has the potential to affect the process under observation. In practice exogenous labels have proven to be particularly problematic in electrophoretic separations.

As previously discussed, in preferred embodiments, the present invention provides methods for the separation and subsequent labelling of a component, such as a protein, within a fluidic device. Labelling after separation avoids the issues that are discussed above. Thus, the behaviour of the component prior to and during separation is not affected, as no label is present.

The present inventors have developed an electrophoretic separation that is coupled to a detection step, which step includes a post-separation labelling. FIG. 5A and FIG. 5B show the designs of a device according to the invention that may be used in a method of the invention.

Figure 5A:
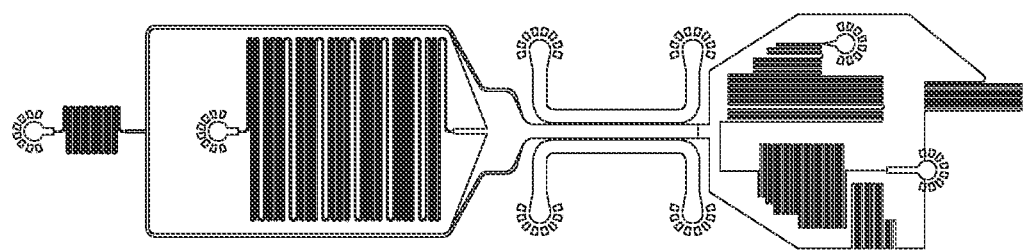
FIG. 5A shows a schematic of an electrophoretic microfluidic device according to an embodiment of the invention.
Figure 5B:
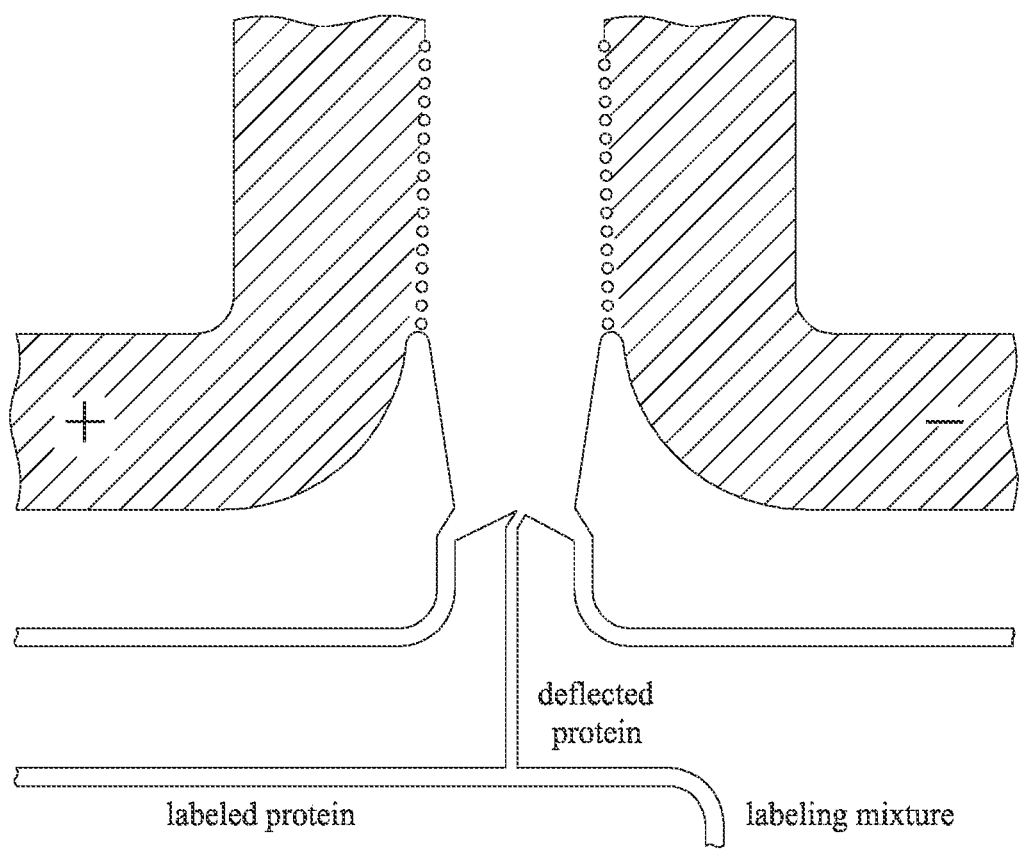
FIG. 5B a schematic of the electrophoretic microfluidic device showing a part of the separation channel in fluid connection with a downstream flow separator, and a labelling channel which joins with an outlet from the flow separator.

Protein and buffer are loaded into device inlets shown at left in FIG. 5A. The buffer fluid flow is provided either side of the protein fluid flow. The fluid flows contact in a large cross section channel, and the combined laminar fluid flows pass into a small cross section channel. Some of the present inventors have previously established that the use of a large cross section channel minimise fluid stagnation at the junction.

Electrodes are provided either side of the small cross section channel and are for use in deflecting the component across the channel. The large and small cross section channels make up the separation channel. At the downstream end of the small cross section channel there if provided a flow separator, which diverts a part of combined fluid flow. In the device of FIG. 5A, the flow separator diverts a part of the buffer flow.

FIG. 5B is a close up view of the device of FIG. 5A showing the flow separator, which is located offset the longitudinal centre line of the small cross section channel.

The diverted flow in the flow separator is permitted to join with a flow of a labelling mixture. The flow of the labelling mixture is provided from a reservoir, as shown in FIG. 5A. Components in the diverted flow are labelled and are then subsequently analysed. The flow channels that are downstream of the flow separator make up the detection zone.

The resistances are such that, when the device is operated through the application of a pressure drop in withdrawal mode, the buffer volumetric flow rate is ten times that of the protein volumetric flow rate, such that the protein distribution is that of a sharp, "hat" function, flanked by sheathes of buffer. The "beam" of protein, which is the central fluid flow, passes through the separation channel, which is provided with electrodes at either side of the channel. When a voltage is applied across the channel, the protein is deflected into a buffer flow, and the degree of deflection is related to the protein charge-to-size ratio. Deflection directs the protein towards or away from the flow separator, which diverts a part of the buffer fluid flow. The flow separator shown in FIG. 5A and FIG. 5B is designed to divert about 10% of the total flow volume leaving the separation channel. The flow is diverted to the 35 detection zone, where the protein is labelled and subsequently detected.

Undiverted flow from the separation channel is also collected and is recombined with the diverted fluid flow exiting the detection zone (as shown in FIG. 5A).

Diverted protein is mixed in a 1:1 ratio with the latent covalent labelling (LCL) solution, (here 11 mM OPA, 16 mM BME, 180 mM carbonate, pH 9.5). The solutions mix in a channel (also known as a waiting loop) over several seconds, which both denatures and quantitatively labels the protein. The fluorescence intensity of the fluid flow is then measured.

The devices were cast in Polydimethylsiloxane (PDMS), which was tinted black to reduce fluorescent background by adding approximately 0.2% w/v carbon nanopowder prior to curing. The black devices were aligned, and beam deflection was verified, by loading together with the protein a fluorescent dye with excitation and emission spectra that do not interfere with the protein label (e.g. OPA label) absorption, excitation, or emission. Here, Rhodamine 6G was chosen as a tracer dye. After aligning the device and verifying appropriate deflection for the tracer dye, the applied voltage was varied and fluorescence intensity in the detection zone was measured. Because labelling is typically quantitative (with OPA, for example), fluorescence intensity is directly proportional to the concentration of deflected protein.

Figure 5C:
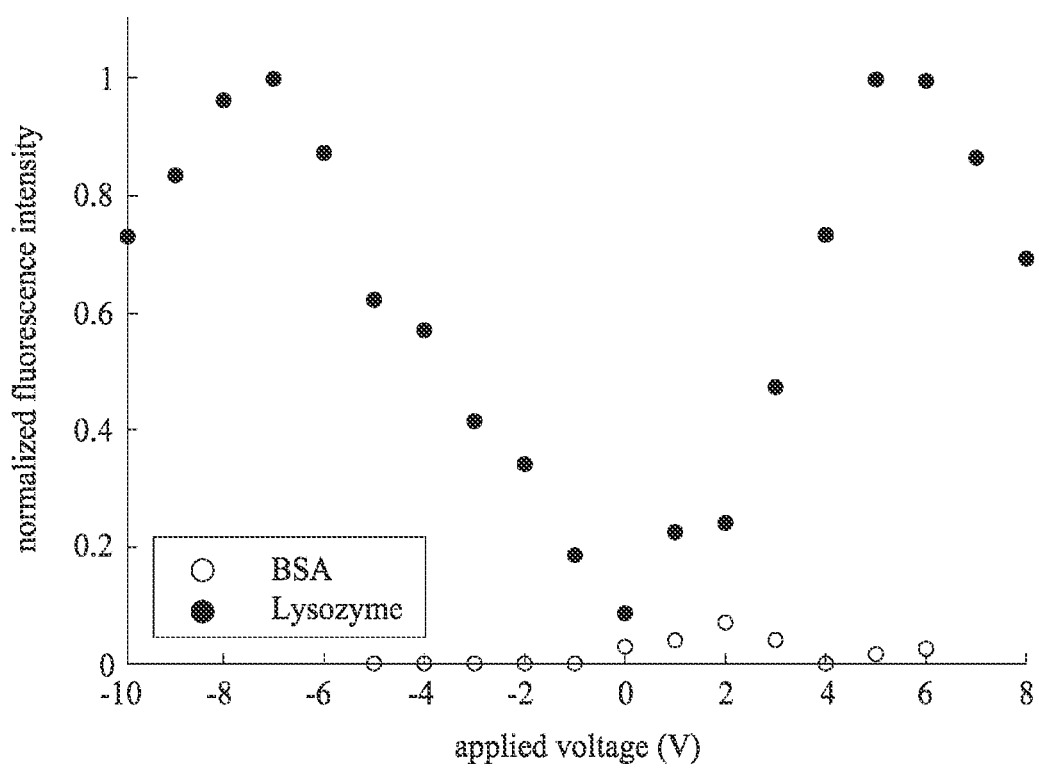
FIG. 5C the change in normalised fluorescence intensity for deflected BSA and lysosome with the change in the voltage applied across the separation channel at pH 7. BSA and lysozyme are oppositely charged at pH 7 due to their differing isoelectric points.

The device was used to separate and detect the proteins BSA and lysozyme, across a range of voltages in the separation channel. FIG. 5C shows the voltage dependent deflection profiles for BSA and lysozyme. BSA has an isoelectric point of 4.7 (Ge et al. *J. Biomater. Sci. Polym. Ed.* 9, 131-150 (1998)) and should be negatively charged at pH 7.

Lysozyme has an isoelectric point of 11.4, and should be positively charged at pH 7 (Wetter et al. *Journal of Biological Chemistry* 192, 237-242 (1951)). Thus, BSA and lysozyme are deflected in opposite directions within the separation channel, with Gaussian-like voltage-deflection profiles. The tightness of the voltage-deflection profiles can likely be further reduced by increasing the flow rate or reducing the volume fraction of protein which is spatially diverted for detection.

Additional Experimental

Additional experiments in support of the invention are provided below. The inventors have 30 explored the use of diffusive techniques to characterise component interactions, such as protein-protein interactions. The inventors have also prepared further embodiments of their fluidic devices, and have used such devices to separate and label components within fluid flows.

Additional Bulk Labelling Measurements

A variety of fluorogens, stoichiometries, and denaturing conditions were surveyed using a fluorescence spectrometer (Varian, Cary Eclipse) and fluorescence microplate reader (BMG LabTech), in quartz fluorescence cuvettes (Helima), or half-area non-protein binding microplates (Corning, product #3881), respectively.

The quantitative labelling mixtures used in the additional work included: 12 mM OPA, 18 mM BME, and 4% w/v SDS in 200 mM carbonate buffer, pH 10.5. Labelling solutions were protected from light at room temperature, and used within 3 days of preparation, or frozen and used within 14 days of preparation. This labelling solution was typically mixed 1:1 v/v with a sample of interest.

Unless otherwise stated, protein solutions were prepared in 5 mM HEPES, pH 7.0, and their concentrations were determined spectrophometrically on a NanoDrop UV-Vis spectrophotometer.

Time controlled fluorescence measurements were performed using a CLARIOstar microplate reader (BMG LabTech) fitted with an injector module. The measurements were performed in 'well mode,' meaning that each well was treated separately. The injector module injected 50 µL dye into a single well at a speed of 430 µL/s, agitated the plate for 1 s, and then measured the sample every 0.25 s for a duration of 125 s, before moving on to the next well. Each sample, and dye background solution, was prepared in triplicate.

Additional Microfluidic Design and Fabrication

As before, microfluidic devices were designed using AutoCAD software (Autodesk, Inc.). An acetate binary mask is then obtained (MicroLithography Services), with clear regions corresponding to channels in the microfluidic device, and black regions corresponding to the background. A device having the design shown in FIG. 24 was prepared.

Microfluidic devices were fabricated using standard soft-lithography techniques. A silicon master which presents positive impressions of the device to be cast was prepared. The device height was set by spin-coating the desired thickness of negative epoxy photoresist (MicroChem, product #SU-83025, depending on the desired thickness) onto a silicon wafer. Devices used in the additional work described herein were 25 μm high. Positive features ultimately corresponding to negative device channels were created by blocking a portion of the photoresist with the acetate mask, cross-linking the exposed areas with collimated UV light, and removing uncross-linked polymer with propylene glycol mono methyl ether acetate (PGM EA) developer (Micro-Chem), according to the manufacturer's instructions.

Microfluidic devices were cast in polydimethylsiloxane (PDMS). PDMS elastomer and curing agent (Dow Corning, product #184) were mixed in a 10:1 weight ratio, respectively. It was important that mixing was thorough: manual agitation for at least 5 min. was important for optimal cured elastomer performance. If black PDMS was cast, this was prepared by adding approximately 1 mg/mL of carbon nanopowder (Sigma, product #633100) to the 40 elastomer/curing agent, and mixing thoroughly.

Figure 24:
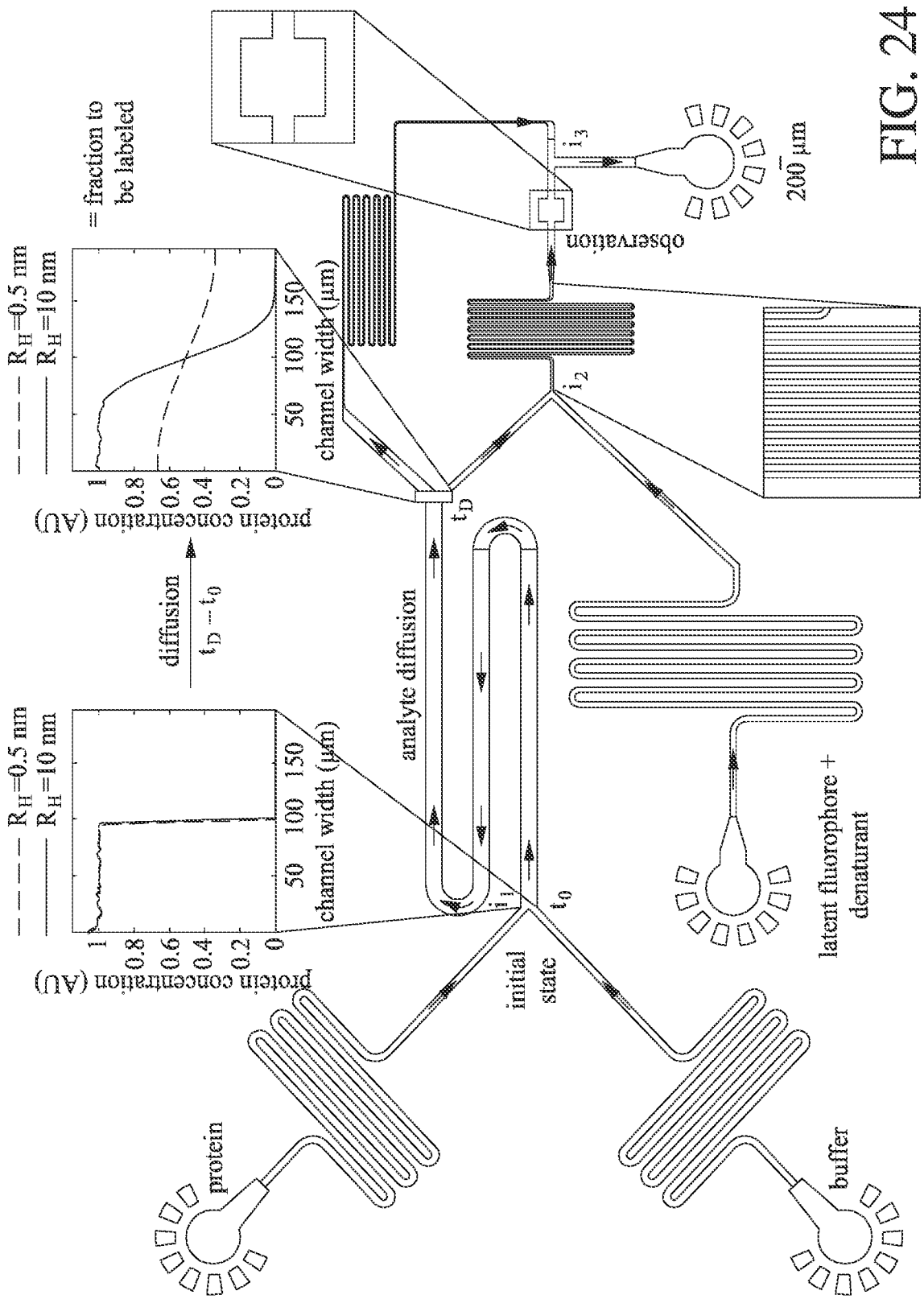
FIG. 24 is a schematic of a diffusion microfluidic device according to an embodiment of the invention, and representing an adaptation of the device shown in FIG. 13.

The device was operated via withdrawal of fluid at the outlet. The dimensions of the channels were thus chosen to control the relative rates of fluid flow through the device, based on analogy between hydraulic and electrical circuits. In a representative diffusion-based device as shown in FIG. 24, a protein solution and a buffer solution contact in a 1:1 volume ratio at the upstream end of a separation channel, and the contacting flows of protein and buffer solutions travel downstream in the separation channel at a rate of 25 μL/hr. One third of the resulting stream (which contains protein having diffused the furthest from the initial protein-containing flow) is then diverted from the combined flow. This diverted portion, which is a part (only) of the buffer flow is then contacted with a flow of the OPA fluorescent labelling mixture in flow, in a 1:1 volume ratio. The volume ratios may be varied depending on the system of interest.

Based on the kinetics measurements set out in FIG. 23, fluorescent detection takes place 3.1 s after the initial contact of the OPA fluorescent labelling flow and the diverted flow.

It was found that components, such as proteins, which passed through their isoelectric point during the in-flow labelling reaction had a tendency to adhere to the hydrophobic PDMS of the flow device. This problem was eliminated (and the general flow rate stability increased) if the PDMS channels were made more hydrophilic.

To achieve this increased hydrophilicity, sealed PDMS channels were subjected to a second extended plasma oxidation step, to create silanol groups on the channel surface, as is described below.

However, oxidized black devices were more vulnerable to non-specific protein adsorption than were oxidized clear devices, likely because the presence of carbon imperfections at the surface could render the silanol layer more prone to cracking and hydrophobic recovery.

Accordingly, a 'sandwich' device was developed, where the channels were cast in a thin layer of clear PDMS, which was then covered at the top and sides with black PDMS to reduce fluorescence background.

Accordingly, an approximately 2 mm thick layer of clear PDMS was cast and baked for 60 min. Clear PDMS devices were cut and reversibly bonded, channel side down, to a Petri dish which had been cleaned with nitrogen. It was important to ensure a clean cut was made around the clear PDMS devices: imperfections along the edge were found to cause poor bonding and would allow black PDMS to seep under the clear PDMS and into the channel features To further reduce seepage, black PDMS is advisably prepared from a clear device which has been allowed to cure at room temperature for several hours to increase the viscosity of the substrate. Black PDMS may then be poured into the top of the reversibly bonded clear device, for a total added height of about 3 mm. The sandwich device is baked for 75 minutes.

After baking, the hybrid devices were easily removed from the Petri dish, and the devices were cut out. Holes were punched at the inlets and outlets using 0.75 mm diameter Uni-Core punches (Harris). Debris was removed with 'magic tape' (Scotch) and IPA sonication, prior to bonding. It was important to remove residual IPA (which is absorbed into the PDMS) prior to bonding, so devices were blown dry with nitrogen, and baked for 15 minutes before the bonding step.

The initial bonding involved a 10 s generation of oxygen plasma. After devices were sealed, they were baked for 10 min. to allow for the formation of a complete seal. Subsequently, the sealed devices were oxidized again, with a 500 s oxygen plasma generation at high power. The devices were filled with water immediately after the oxidation step (using protex 0.38 mm internal diameter, 1.09 mm external diameter tubing, connected to 1 mL plastic Air-Tite syringes) which prevented hydrophobic recovery within the channels. Inlets and outlets were blocked with water-filled gel-loading tips. With this treatment, devices successfully resisted non-specific protein adsorption for at least seven days following bonding and oxidation.

Use of Microfluidic Device

An exemplary device of the invention is shown in FIG. 24, for use in diffusion-based separation methods. Equal portions of folded, unlabelled, native protein molecules and buffer were loaded into the microfluidic device. When fluids are confined to the micron scale, flows are laminar, rather than convective, such that when streams of component and buffer are brought into contact in a microfluidic channel, the spatial distribution of the component across the channel after any defined residence time is entirely determined by the analyte diffusion coefficient.

Crucially, measurement is initiated once the system has reached a well-defined starting state. Because of the absence of turbulent mixing in the microfluidic regime, at to, components of all $R_H$ have the same initial distribution, occupying half the width of the diffusion channel. This situation is illustrated in FIG. 24 by the equivalence of the lateral concentration gradients for simulated 0.5 and 10 nm species. The system is then allowed to evolve for a defined period of time as diffusion takes place. After diffusion over time $t_D$-$t_0$, the smaller 0.5 nm species have diffused further than the 10 nm species.

Spatial separation perpendicular—rather than temporal separation parallel—to the direction of flow, observed for a microfluidic system operating at steady state, allows for the continual diversion of a fraction of the spatial distribution to downstream modules, without resolution loss.

Relative fluid flows throughout the device are precisely set by varying the pressure difference along possible paths, which is achieved by controlling the hydrodynamic resistance with the channel dimensions. In this manner, the fraction of the distribution which has diffused at least one sixth of the channel width in time $t_D$-$t_0$ (rectangles), is at time $t_D$ directed to the labelling module. At this location, the conditions are changed, via the introduction of the labelling solution at co-flow junction $i_2$, to permit quantitative modification
of all reactive protein groups.

Because the latent fluorophore is itself not fluorescent, no purification steps are required. Provided the protein sequence, and thus number of reactive groups, is known, measurement of fluorescence intensity allows for determination of the absolute protein concentration.

Buffer and loaded samples were initially filtered through a 0.22 µm filter (Millipore) prior to use, to eliminate particulate matter which could clog the devices. Devices were loaded by filling from the outlet with the appropriate native buffer.

Generally, either a 1 mL Hamilton glass syringe or a 1 mL plastic Air-Tite syringe (connected through a 27 gauge needle to Portex tubing) was used to control the flow of fluid through the device.

No difference was noted between the performance of glass and plastic syringes at the flow rates used in these experiments. Pressure was applied simultaneously at the inlets and the syringe to remove any bubbles formed during the loading process, and reagents were introduced with gel loading tips at the device inlets.

Reagent loading varied between 10 and 200 µL, depending on the experiment. It is noted that smaller volumes may be used in the methods of the invention.

As with the earlier described experiments, fluid was withdrawn through the device with a neMESYS syringe pump. In order to initially draw reagents through the device and minimize effects of any inlet cross-flow during the loading step, 20 µL fluid was initially withdrawn at a flow rate of 300 µL/hr. For the diffusion-based devices used in the experiments, a 25 µL/hr flow rate in the separation channel was used, which corresponded to a 33.3 µL/hr withdrawal rate at the outlet of the device. The flow rate was allowed to equilibrate for at least 18 minutes prior to the start of image acquisition.

Brightfield and fluorescence images were acquired using a Zeiss AxioObserver Microscope, fitted with a CoolSNAP MYO CCD camera (Photometrics), 365 nm Caim OptoLED (Photometrics), and a Chromo 49000 DAPI Filter (Photometrics) for the fluorescence images. 2.5×, 5×, 10×, and 20× objectives were used. Exposure times of between 10 ms and 10 s were used in the additional work, and generally between 10 and 60 images were averaged during each acquisition.

When the fluorescence signal was low, EM gain was used, or adjacent pixels were binned. For each set of measurements and imaging settings, at least one dye background image was taken to account for the minimal fluorescence of the unreacted dye. A flatfield background image was also acquired. Measurements were taken in a dark environment, and the temperature during analysis was maintained at 25° C.

Image Analysis and Fitting

Images of the junctions (such as the upstream region of the separation channel), channels (such as the detection channel, where the labelling flow is brought into contact with the diverted flow) and flow separator were routinely acquired. Where these images revealed altered flow profiles due to clogging, or other abnormalities, images acquired in the detection zone were discarded.

Basic image analysis was performed in ImageJ. A flatfield background image was subtracted from each image acquired. Briefly, a region of interest was defined directly upstream of a residence time marker (discarding the regions near the device walls, where due to the no-slip boundary condition flow rates are significantly reduced). Mean fluorescence within this region was calculated, and from this mean fluorescence in flatfield regions of the chip directly above and below the channel was subtracted, which reduced the effects of variation in in the illumination source intensity over time, and sample adsorption onto the PDMS.

Sample hydrodynamic radius was calculated via comparison of experimental intensity ratios to those simulated for reference particles of known size. Thus for each sample, the following ratio was calculated:

$$\phi = \frac{\gammaت - \gamma d}{\gamma 2 - \gamma d}$$

where ø is the intensity ratio comparing diffusing and homogeneously distributed sample used in subsequent analysis, $y_1$ is the background corrected fluorescence intensity in the detection zone, which is observed when the sample is loaded into one device inlet, $y_2$ is the background corrected fluorescence intensity in the detection zone, which is observed when a sample is loaded into both inlets of the device, and $y_d$ is the background corrected intensity of the OPA labelling mixture. ø is used to determine the hydrodynamic radius of each sample based on interpolation from that observed for the basis functions.

On-Chip Absorption

Bulk absorption measurements were performed using standard protein $A_{280}$ settings on a NanoDrop spectrophotometer, although similar results were obtained when a Varian UV/Vis spectrophotometer was used. This is described in the Bulk Absorption section below.

On-chip UV absorption measurements were performed using a commercial cyclic olefin copolymer chip (ThinXXS, channel cross section 320×320 µm) and an ActiPix D100 UV area imaging detector (Paraytec). The total device thickness was 1.7 mm, and all measurements were taken in a dark environment.

A solution containing 150 µM BSA was permitted to flow through one inlet of the device and Milli-Q water through the other at a rate of 50 µL/h each to form an interface. The channel was illuminated by 8 consecutive signal bursts by the instrument's pulsed xenon lamp (band-pass filtered at 280 nm) with 10 ms delay between bursts. The ensuing light intensity was integrated over a time span of 100 ms. Background correction with a measurement taken with a channel filled with just water gives a signal-to noise ratio of around 120. This results in a detection limit for this device set up of several µM.

It should be noted that in fused silica capillaries, concentrations of down to around 100 nM BSA have been detected.

Bulk Absorption

The sensitivity observed for bulk absorption measurements was compared against the methods of the present case.

It was found that approximately 600 nM protein was required to accurately determine protein concentration via bulk absorption (see FIG. 20), whereas sub-nM protein concentrations could be accurately determined in bulk with the methods of the present case, where they make use of the OPA-labelling procedure.

Figure 20:
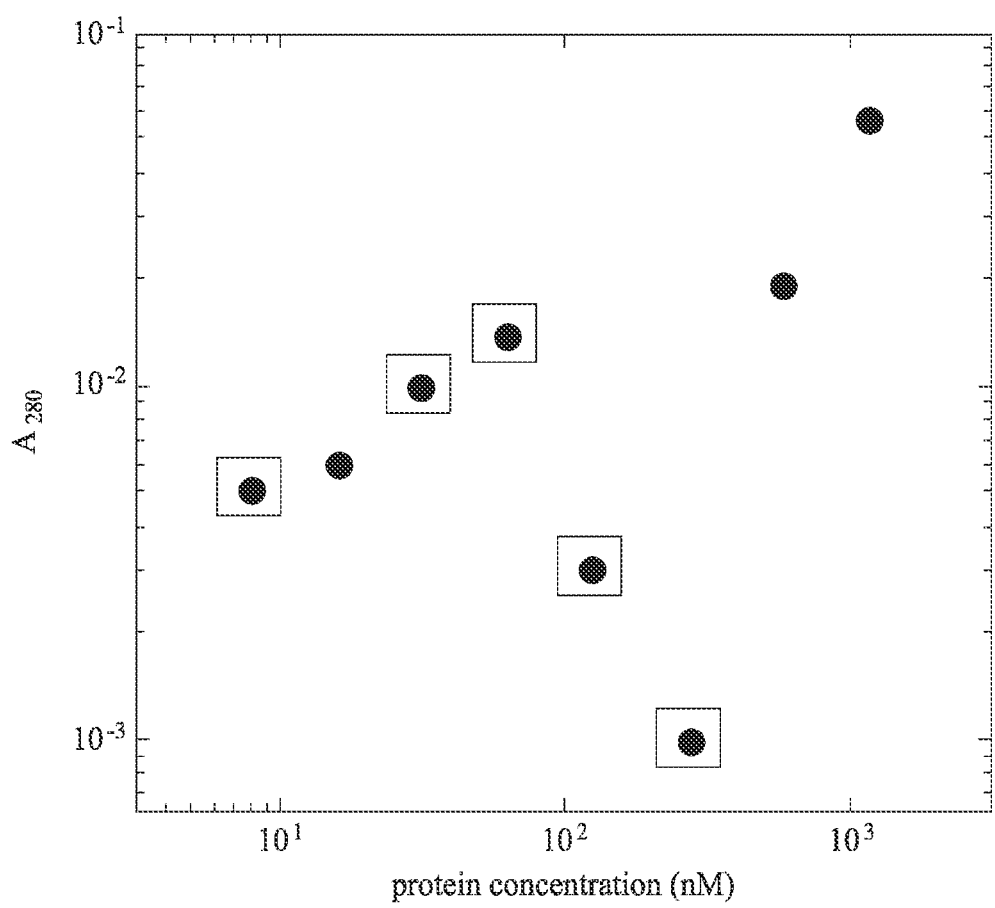
FIG. 20 shows the change in recorded bulk absorption at $A_{280}$ with change in protein concentration (nm) for a series of BSA solutions prepared from a stock sample of known concentration. The squares represented data points where the recorded absorption was less than the buffer blank.

A number of BSA samples were prepared of varying concentration by diluting from a concentrated stock solution, whose concentration had been spectrophotometrically determined. $A_{280}$ was plotted as a function of protein concentration (nM) as shown in FIG. 20. Where a marker is placed in a square, this indicates that the sample absorbed less light than the buffer blank. Approximately 600 nM BSA was required to accurately determine protein concentration from $A_{280}$.

Non-Specific Protein Adsorption and Flow Stability

The microfluidic devices of the invention are typically fabricated in polydimethysiloxane (PDMS). The advantages of PDMS soft lithography techniques are well recognized, most notably rapid prototyping, low cost, and high throughput compare to other lithographic methods. However, a problem emerges where components such as proteins are transported through a fluidic device at a pH below the isoelectric point of the component.

In the preferred labelling steps of the present case, the labelling mixture increases the alkalinity of the fluid flow to around pH 10.5.

When a component such as a protein passes through its isoelectric point (IEP) on chip, component that is present at the laminar flow interface between the component-containing flow (such as might be present in the diverted flow) and labelling streams is rendered temporarily uncharged, and the component is seen to adhere to the PDMS channel surface. Such adherence blocks microfluidic junctions, causing flow disruptions. This can cause a significant variation in the generated fluorescence in the detection zone over time. This makes quantitative interpretation of recorded results difficult and sometimes impossible.

In order to address this issue it is helpful to perform an additional plasma oxidation step on PDMS devices which have already been bonded to the glass surface. This additional oxidation treatment forms a hydrophilic, glassy siloxane layer on exposed surfaces of the PDMS channels, which reduces nonspecific component adsorption and greatly improves flow stability.

However, these beneficial properties are lost when channels are cast in black PDMS, most likely due to accelerated hydrophobic recovery in the presence of carbon imperfections at the siloxane surface. In this work the inventors have developed sandwich devices which combine the benefits of effective channel oxidation and reduced fluorescence background.

FIG. 21 shows the change in normalised fluorescence (AU) over time (s) for bovine insulin passed through its IEP in a fluidic device, where FIG. 21A is a standard PDMS fluidic device according to an embodiment of the invention; FIG. 21B is a standard PDMS fluidic device that has been subjected to an additional plasma treatment; and FIG. 21C is a standard black PDMS fluidic device that has been subjected to an additional plasma treatment.

In a standard device (one that is not subjected to an additional plasma treatment) significant aggregate deposition is observed in the fluid channels. It follows that there is a significant change in the normalised fluorescence signal over time (as seen in FIG. 21A). Extended plasma oxidation of the PDMS surface creates a silanol-rich hydrophilic layer which resists protein adsorption. When clear PDMS channels are oxidised in this manner, they resist protein deposition at laminar flow interfaces, which allows for significantly improved flow stability (as seen in FIG. 21B). However when black channels are oxidised, some resistance to nonspecific protein adsorption is lost, resulting in a slight decrease in flow stability as compared to the clear devices (compare FIG. 21C with FIG. 21B). To address this, the inventors have used a hybrid 'sandwich' device, in which the channels are formed from clear PDMS to facilitate effective and lasting oxidation, while a black PDMS covering at the top and sides reduces fluorescence background.

$R_H$ determination

In the flow systems of the present case, the system operates at steady state. The measurement of a component concentration downstream in the detection zone reveals the total concentration of the component that was diverted for labelling. Although the spatial distribution is not directly visualised in the analytical data, the component $R_H$ is accessible when an additional measurement is made.

Figure 22A:
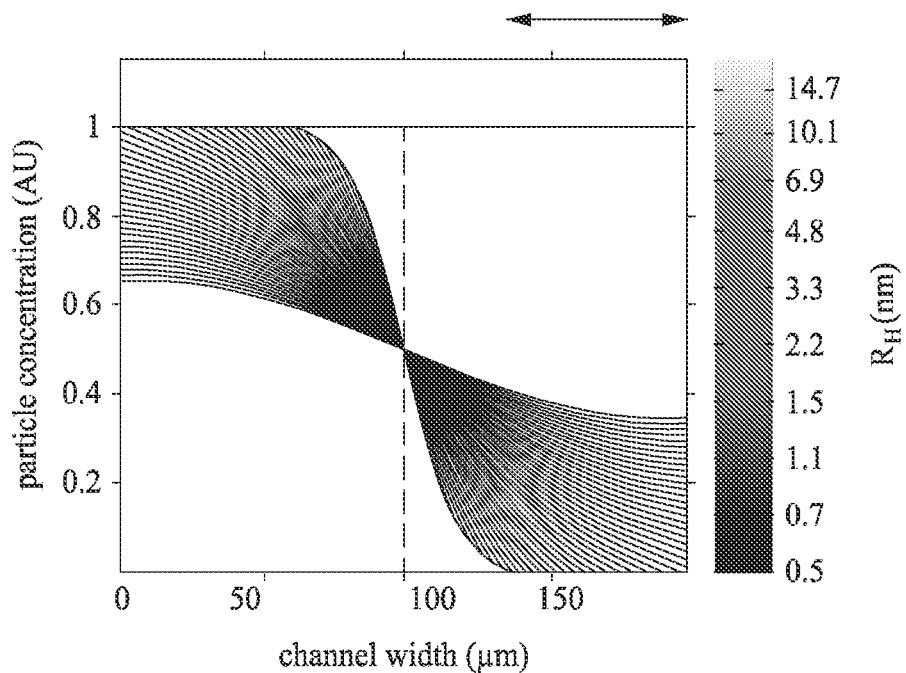
FIG. 22A shows the particle concentration (AU) for reference components of known hydrodynamic radius $R_H$ (nm) in a simulated diffusion gradient at time $t_D$, where the components diffuse from a first fluid flow (left of dashed line) to a second fluid flow (right of dashed line) in a modelled channel having a width of 200 µm, and the component population is viewed laterally across the diffusion channel.

FIG. 22A shows a homogeneous reference distribution of a component of known concentration at time tip (line, at 1.0 particle concentration). In practice, this distribution can be easily achieved by providing the component in both the first and second fluid flows.

Figure 22B:
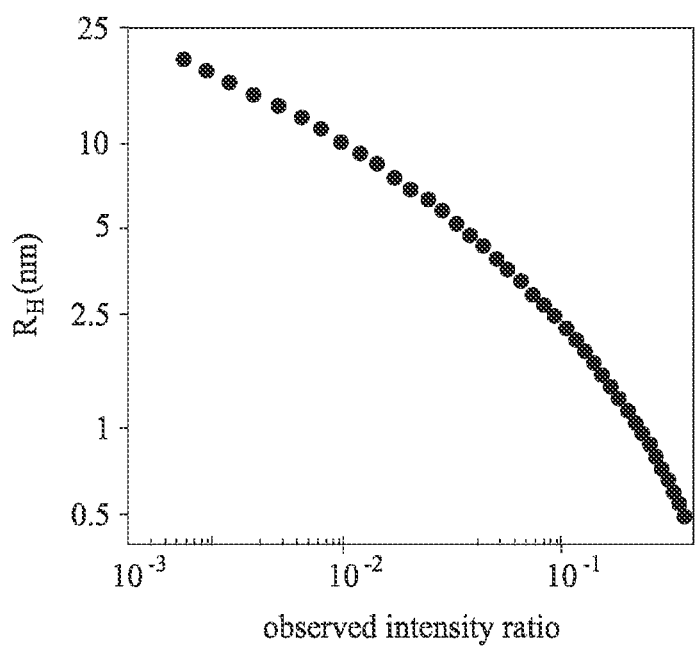
FIG. 22B shows the observed intensity ratios for components of hydrodynamic radius $R_H$ (nm), where these components are diverted from a part of the second fluid flow, which part is shown in FIG. 22A.

Species of each $R_H$ (indicated colorimetrically in FIG. 22A) have a characteristic fraction of diffusing versus homogeneously distributed species diverted for labelling (the diverting step diverts the species that have diffused furthest into the second flow). As labelling is essentially quantitative, this is easily assessed by comparing the fluorescence intensities observed for these species in the detection zone (FIG. 22B). As expected, smaller species predominate, as these species have diffused furthest during the separation step.

The data in FIG. 22A and FIG. 22B are variations of, and consistent with, the data in FIG. 8 and FIG. 9.

To test the ability of the methods and apparatus to size components using diffusive separation and labelling, a sizing ladder was developed and tested. The ladder included biomolecules varying in over three orders of magnitude in molecular weight ($M_w$). The sizing ladder additionally included proteins which varied in secondary and tertiary structure, unfolded as well as folded proteins, and protein complexes.

Figure 22C:
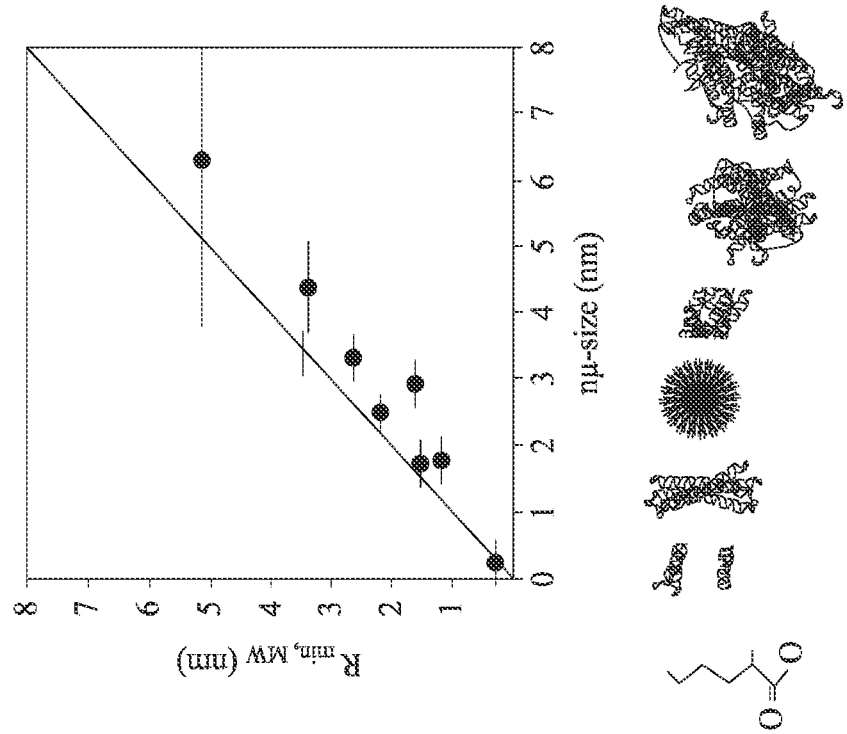
FIG. 22C and FIG. 22D are sizing ladder experiments, contrasting the hydrodynamic radius $R_H$ values determined by diffusion-based methods ("nu-size"; nm) against the values determined by AUC and PFG-NMR FIG. 22C and predicated minimum radii based on the component molecular weights FIG. 22D, for lysine, a heterogeneous mixture of insulin monomer and dimer, β-lactoglobulin dimer, α-synuclein, BSA, BSA dimer, and β-galactosidase.

FIG. 22C shows a comparison between the reported literature hydrodynamic radii values for the various biomolecules as determined by analytical ultracentrifugation (AUC) and pulsed-field gradient NMR (PFG-NMR), and the experimentally derived values from the diffusion-based methods of the present case. In particular, PFG-NMR was used for low $M_w$ weight species with low extinction coefficients, and AUC for higher $M_w$ weight species. Both values were reported where possible. Importantly, neither AUC nor PFG-NMR was suitable over the entire molecular weight range studied.

In contrast, the hydrodynamic radii obtained with the methods of the present case closely paralleled those obtained with the composite of AUC and NMR techniques over the entire $M_w$ range studied.

Uncertainty in in the high molecular weight range can be reduced by labelling a different fraction of the distribution e.g. by collecting a different part of the second flow which has a higher concentration of the higher molecular weight species, or by collecting a part of the first flow (which will be depleted in lower molecular weight species).

Figure 22D:
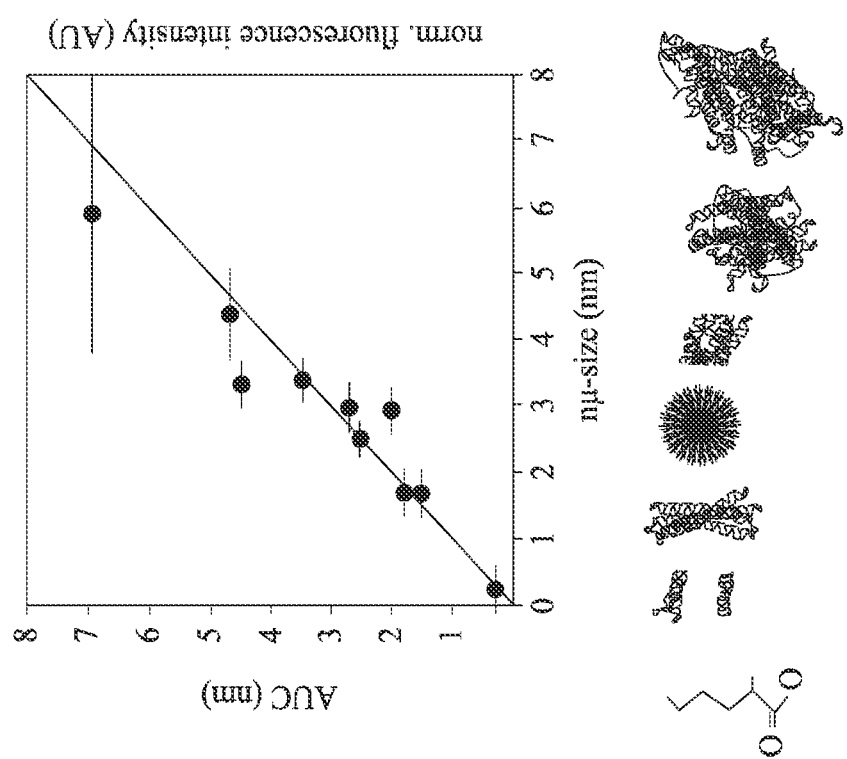

A further comparison of the diffusion-based $R_H$ values was made against predicted 'naive' diffusion hydrodynamic values: this is the hydrodynamic radius of the smallest sphere ($R_{min}$) which could contain a protein of the indicated molecular weight. The comparison is shown in FIG. 22D.

The accuracy of the $R_{min}$ predictions decreased systemically with increasing $M_w$, likely reflecting the non-spherical conformations accessible to proteins with longer sequences.

The sizing ladder includes proteins and protein complexes that can be challenging to characterise using traditional sizing methods. The protein a-synuclein plays an essential role in Parkinson's disease. Because the natively unfolded structure of a-synuclein is not compact, the calculated $R_{min}$, and the $R_H$ obtained from AUC measurements were considerably smaller than those obtained with either PFG-NMR or the diffusion methods of the present case.

The diffusion-based methods of the invention were used to analyse heterogeneous mixtures of protein. An aqueous sample containing $Zn^{2+}$-free bovine insulin was prepared, where the monomer and dimer forms are in equilibrium. The $R_H$ values determined from the diffusive methods was 1.64±0.16 nm, which reflects the proportions of monomer and dimer present in the sample.

Component Interactions

The methods of the present case may be used to investigate the assembly of components, such as proteins, with changes in the component concentration. For example, diffusive separation techniques may be used to study changes in the hydrodynamic radii for species within solution.

A composite hydrodynamic radii can be calculated based on the relative abundance of the composite species, and the radii of the pure components. In a general case, when a single component is analysed:

$$r_H = f_s(\phi)$$

where, $r_H$ is the observed hydrodynamic radius, ø the experimentally observed intensity ratio for diffusing versus homogeneously distributed particles, and $f_s$ is a sizing function which interpolates the size of an unknown sample based on comparing ø to that simulated for the basis functions, as described herein and in relation to WO 2014/064438. In the case of a heterogeneous mixture:

$$r_H = \sum_{i=1}^{n} f_s(\phi_i P_i)$$

a linear combination of the intensity ratio, øi, and proportion, $P_i$ of each i of n mixture components gives $r_H$. It is noted that $P_i$ describes the proportion of primary amines that component i contributes to the total primary amine concentration, and not the total protein concentration.

A series of experiments was undertaken in order to explore whether the composite $R_H$ could be used to extract binding constants, and sizes of pure mixture components, for the quantitative characterisation of protein-protein interactions. The results from the diffusive separation methods of the invention were compared with results obtained by dynamic light scattering, a commonly used diffusional sizing technique.

The oligomierxation of β-lactoglobulin was studied. Although β-lactoglobulin is a commonly used biophysical model protein, equilibrium constants varying in more than an order of magnitude have been reported in the literature, and there is disagreement as to whether oligomerization under physiological concentrations provides dimers only, or whether tetramers and octamers are also present within the population.

Figure 16A:
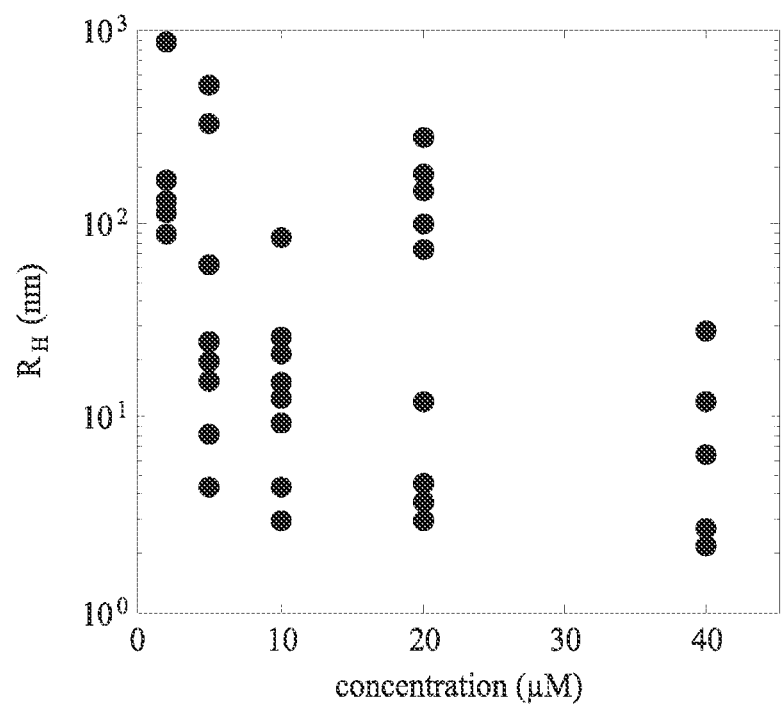
FIG. 16A-FIG. 16B shows the change in measured hydrodynamic radius $R_H$ (nm) with increased β-lactoglobulin concentration (μM) as measured by FIG. 16A dynamic light scattering and FIG. 16B the diffusion-based flow methods as described herein. The data shows the unreliability of the dynamic light scattering approach to determining hydrodynamic radius in comparison with the methods of the present invention.

A series of β-lactoglobulin solutions were prepared at neutral pH and 5 mM ionic strength, with the concentration of β-lactoglobulin ranging from 2 to 40 μM. The solutions were analysed by DLS and the diffusion separation methods described herein. The oligomerisation results are presented in FIG. 16, where the calculated hydrodynamic radii $R_H$(nM) for different concentrations of β-lactoglobulin in solution (μM) is shown for DLS experiments FIG. 16A and diffusion experiments FIG. 16B. The data is presented as the Zave values.

In the DLS experiments, it was only at the highest protein concentrations that sizes reminiscent of the values reported for the protein dimer obtained. However, there is still significant variation in the data and there was still significant variation in the data. By DLS it was not possible to observe the protein monomer in the population.

Figure 16B:
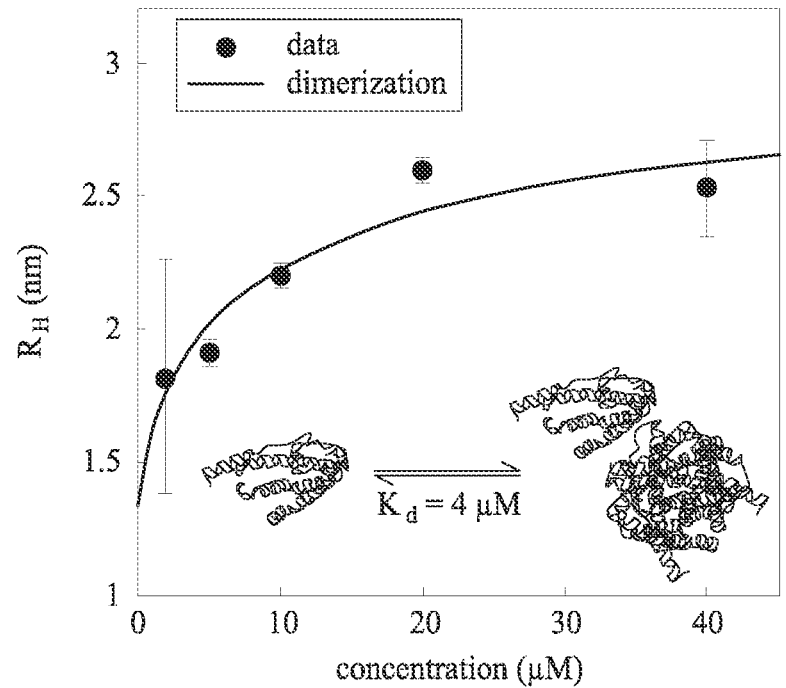

The composite $R_H$ obtained by the diffusive methods of the present case is shown in FIG. 16B). The hydrodynamic radius increases 1.83 and 2.60 nm over the concentration range studied, corresponding to a size increase of 1.4. This is consistent with a dimerization event. To shed further light on the oligomerization mechanism, the data was fitted to obtain $\phi_i$, and $P_i$, for the pure monomer and dimer, as described above. Classically, in a homodimerization event:

$$K_d = \frac{[M][M]}{[D]}$$

$$[M] + 2[D] = C_T$$

where M and D are the molar concentrations of the monomer and dimer respectively, $C_T$ is the total concentration of all species present in the mixture, and $K_d$ is the dimerization constant. Solving the combined quadratic equation yields the monomer concentration, and taking into account the stoichiometry the proportion of primary amines contributed by the monomer $M_{pa}$ $$[M_{pa}] = \frac{K_d}{4}\left\{\left(1 + \frac{8C_T}{K_d}\right)^{\frac{1}{2}} - 1\right\}$$

Equivalently, the dimer primary amine concentration is readily determined to be:

$$[D_{pa}] = [C_T] - [M_{pa}]$$

$$P_m = \frac{M_{pa}}{M_{pa} + D_{pa}}$$

$$P_d = \frac{D_{pa}}{M_{pa} + D_{pa}}$$

yielding the relevant $P_i$ fit parameters. Fitting the data in this manner, a disassociation constant of 4.1 μM was obtained, along with extrapolated sizes of 1.34 and 3.21 nm for the pure monomer and dimer, respectively.

Using the methods of the present case, the measured hydrodynamic was observed to increase by 1.42 nm over the concentration range studied (from ca. 1 μM to 40 μM). The radii presented are composite values, taking into account all mixture components.

To facilitate quantitative analysis of protein-protein interactions the inventors have previously developed an approach to extract equilibrium constants and the sizes of pure mixture components from such composite data, for example as described herein and as described in WO 2014/064438.

As noted above, the data obtained in the study fitted well to a dimerisation model, which revealed a disassociation constant of 4.1 μM, shedding new light on conflicting literature reports of the β-lactoglobulin dimerisation event.

Accordingly, the methods of the invention may be used to identify monomer and assembled components in a mixture.

Separation of Protein Ternary Mixtures

Free-flow electrophoretic separations are more efficient than diffusional separations at separating components of complex mixtures of species. With diffusional separations, low molecular weight species can be separated from high molecular weight species, but the high molecular weight species elute with a background of low molecular weight species. In contrast, with free-flow electrophoretic separations, high resolution can be obtained, and pure components may be isolated, by varying the device geometry (see also Herling et al.).

Figure 17A:
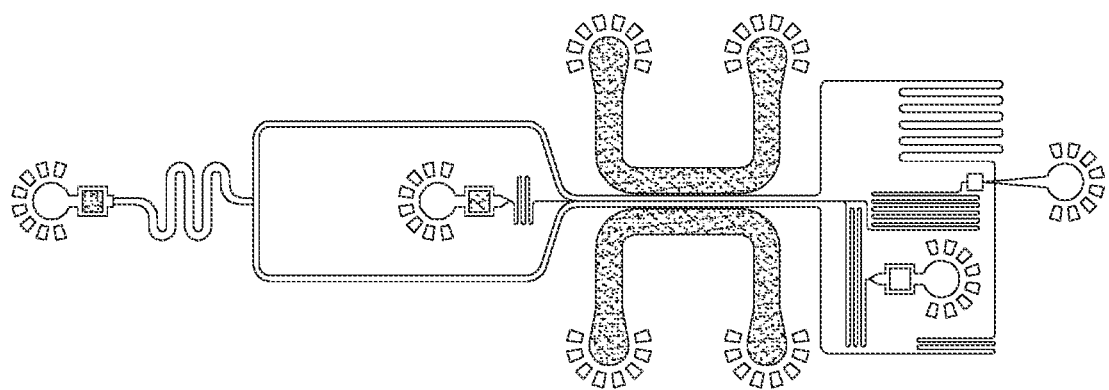
FIG. 17A shows a schematic of an electrophoretic microfluidic device according to an embodiment of the invention.

A fluidic device was prepared incorporating an electrophoretic separation channel, with a downstream flow separator and a detection zone. Providing fluid connection between the flow separator and the detection zone was a labelling channel. A schematic of the device is shown in FIG. 17A. The device is an adaption of the devices of FIG. 5 and FIG. 14. The device incorporates a steady state post-separation labelling step after a free-flow electrophoretic separation and diversion. The device was prepared using standard PDMS soft lithography techniques, such as described above in the Device Fabrication section.

A well-defined 'beam' of a component, such as a protein, is established by providing flows of buffer either side of a component flow. A laminar flow is established. The width of the component flow within the separation channel is tunable based on varying the relative flow rates of the component and buffer flows.

When no voltage is applied across the separation channel (across the width of the laminar flow), the component is not diverted into a neighbouring buffer flow. Accordingly, in the absence of an applied field, components within the component flow are not diverted to the labelling channel and the detection zone. The flow separator is provided to divert a part (only) of the buffer flow at the downstream end of the separation channel. Component present in the component flow at the downstream end of the separation channel is simply collected in a waste channel.

When an electric field is applied across the separation channel, a component may be deflected from the component flow into a buffer flow, and which of the two flanking buffer flows will depend upon the charge of the component and the direction of the applied field. A component that is deflected into a buffer flow may be diverted by the flow separator, and the diverted flow is taken downstream. In the downstream region the diverted component may be labelled, such as fluorescently labelled, for detection in the detection zone.

The flow separation device was tested using five different protein solutions. Three protein solutions were prepared containing one of BSA, β-lactoglobulin, and lysozyme (1.0 mg/mL), a binary solution containing BSA and lysozyme was also prepared (1.0 mg/mL total protein concentration; 0.5 mg/mL for each protein), as well as a ternary solution containing BSA, β-lac, and lysozyme (1.0 mg/mL total protein concentration; 0.33 mg/mL for each protein). Lysozyme containing solution additionally comprised 1% v/v Tween surfactant, in order to 10 minimise precipitation of the lysozyme during the labelling step.

Flows of each protein solution were established in the fluid device, and the protein flow was permitted to pass along the separation channel. The applied field across the channel was varied, and the deflection of each protein in response to the applied field was monitored. Protein deflected into the buffer flow could be collected by diversion of a part of the buffer flow at the downstream end of the separation channel. Diverted buffer flow, containing protein, was then contacted with a labelling flow, in order to fluorescently label the protein for detection. The labelling flow included a denaturant and the latent label OPA, which was used as described herein. After labelling, the protein was detected by fluorescence spectroscopy. The intensity of the recorded signal was directly proportional to the concentration of protein diverted from a part of the buffer flow at the downstream end of the separation channel.

Figure 17B:
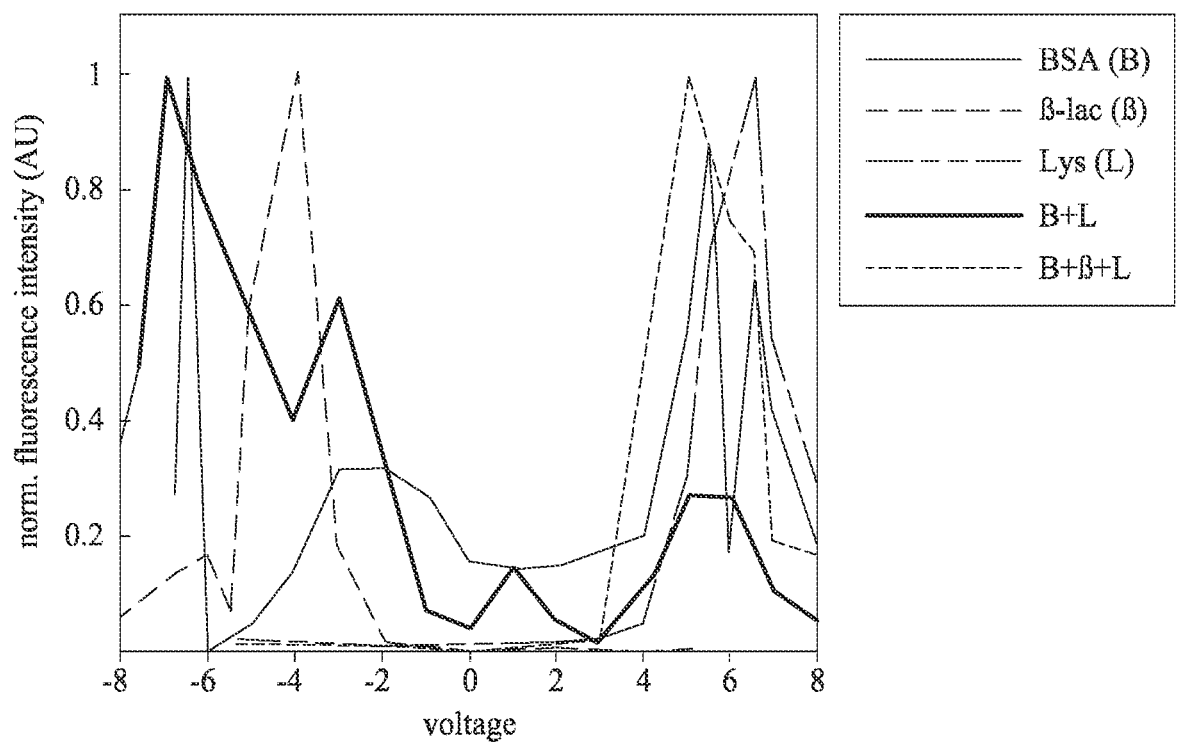
FIG. 17B the change in normalised fluorescence intensity (AU) with change in the voltage (V) applied across the separation channel in the electrophoretic microfluidic device for five different protein solutions, where a BSA solution has a maximum fluorescence intensity at around 4.0 V, a β-lactoglobulin solution has a maximum fluorescence intensity at around 6.0 V, a lysozyme solution has a maximum fluorescence intensity at around −4.0 V, a BSA- and lysozyme-containing solution has fluorescence maxima at around −7.0 V and 5.0 V, and a BSA-, β-lactoglobulin- and lysozyme-containing solution has fluorescence maxima at around −6.0 V, −2.0 V, 5.0 V and 6.0 V.

FIG. 17B shows the change in normalised fluorescence intensity (AU) with change in the field (V) applied across the separation channel for each of the five solutions described above.

For the BSA-containing flow, the fluorescence intensity recorded in the detection zone was at a maximum when the applied field across the separation channel was around 4.0 V.

The fluorescence intensity for the β-lactoglobulin-containing flow was at a maximum when the applied field across the separation channel was around 6.0 V. The fluorescence intensity for the lysozyme-containing flow was at a maximum when the applied field across the separation channel was around −6.0 V. The deflection profiles were voltage dependent and corresponded to the expected deflections of the protein based on the charge of that protein at the experimental pH (pH 7.0 for each solution).

The application of a particular voltage across the separation channel may be used to preferentially deflect a component of interest in a multicomponent flow. In this way, one component may be separated from other components in a multicomponent mixture. The binary and tertiary mixtures described above were used to validate the free-flow electrophoretic separation and labelling of one component from one or more other components. Distinct peaks were observed in the binary and ternary mixtures, which correspond to the peaks observed for the individual proteins.

Of particular interest is the apparent resolution between BSA and β-lactoglobulin, which have similar isoelectric points.

The broad peak observed for the ternary sample near zero voltage could reflect a distribution of oligomers arising from electrostatic interactions between the oppositely charged proteins. Further work is currently underway to investigate this.

Quantitative Labelling: Kinetics

The present inventors have investigated a variety of strategies for achieving quantitative labelling. Because the fluorophore formed during an OPA-labelling reaction lacks chemical stability, techniques like mass spectrometry are not ideally suited to assess the extent of component labelling.

An assay was designed in which quantitative labelling could be assessed directly at a defined time after mixing. Proteins were used as test components. Fluorescence intensity was compared to the concentration of reactive groups (protein concentration x number of primary amines in the protein sequence) for well-characterised proteins with varying secondary and tertiary structures.

The reference set included bovine serum albumin (BSA), β-lactoglobulin (β-lac) at pH 2 and pH 7, lysozyme (Lys), calmodulin (CaM), and a myosin kinase peptide (P7). The reference set included proteins which passed through, or were brought near, their isoelectric points during the labelling reaction The labelling reaction for proteins in the set was compared with the labelling reactions for free glycine and lysine, which have reactive primary amine groups analogous to those modified during the labelling reaction, but which are entirely solvent accessible (see FIG. 23A).

Figure 23A:
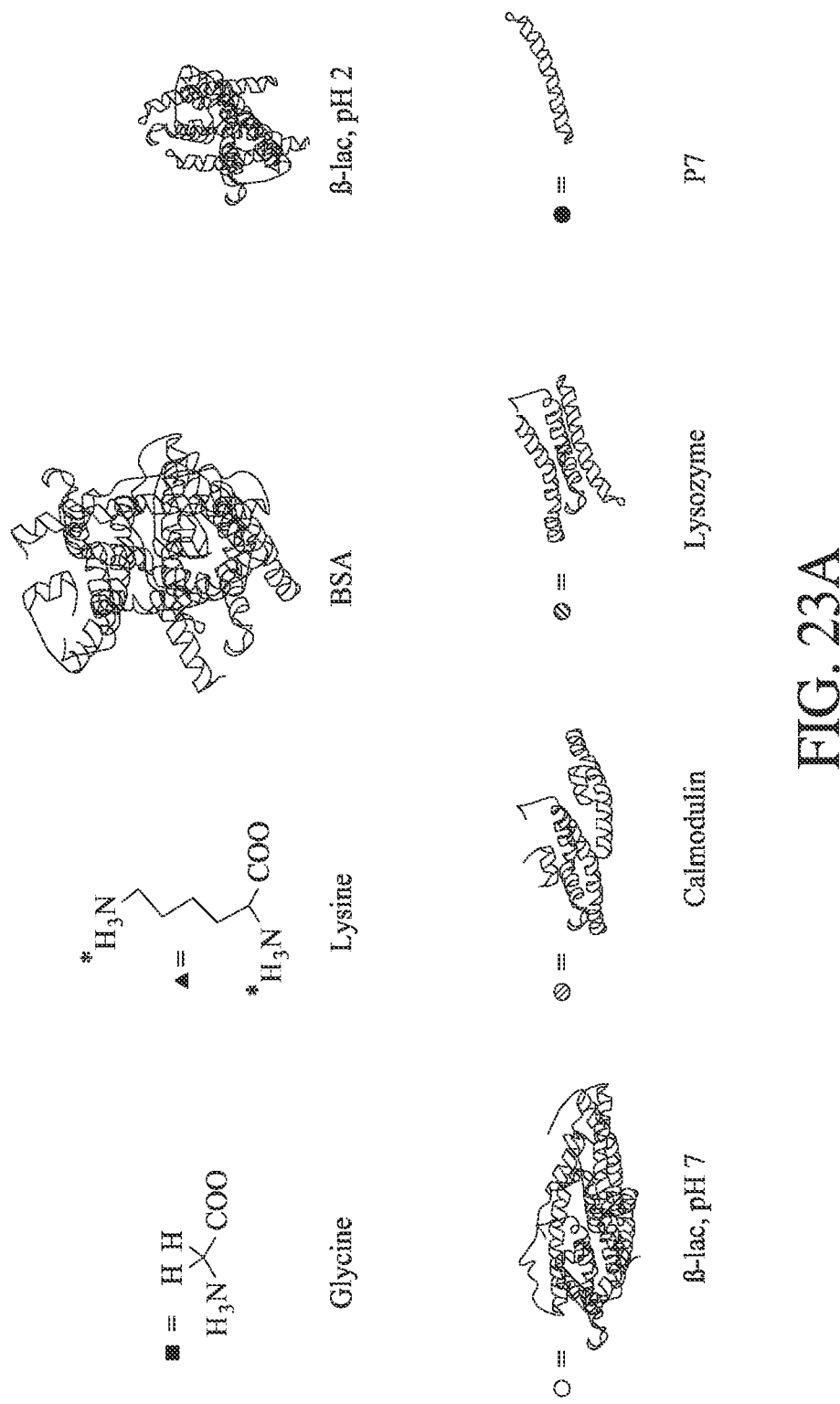
FIG. 23A shows a schematic of the structures of the proteins used in the quantitative labelling tests.
Figure 23B:
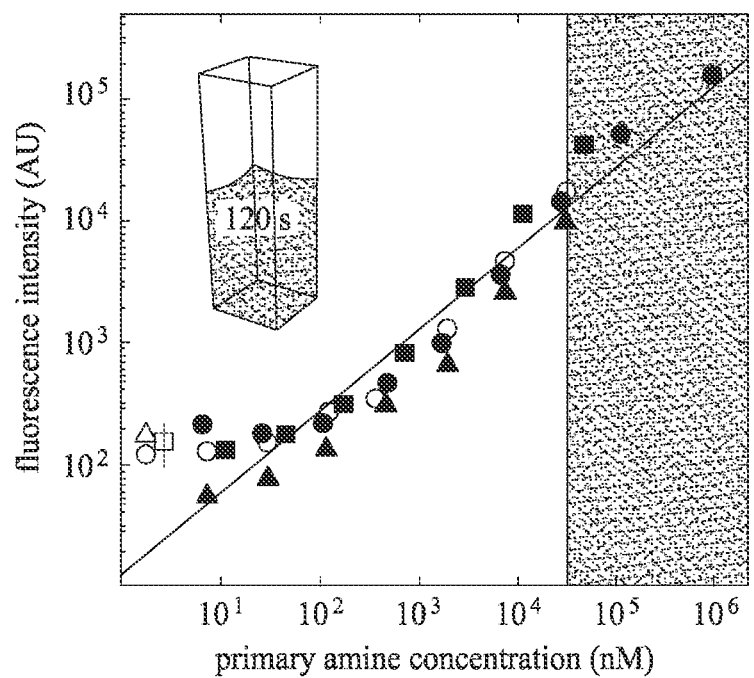
FIG. 23B shows the change in recorded fluorescence intensity (AU) with change in primary amine concentration for the proteins 120 s after they are exposed to the OPA labelling mixture.

It was found that a combined denaturation strategy—which included the addition of 4% sodium dodecyl sulfate (SDS), an excess of BME, and a highly alkaline reaction mixture—resulted in a linear relationship between primary amine concentration and fluorescence intensity when fluorescence intensity was measured in bulk 120 s after mixing (FIG. 23B).

The data reveal sigmoidal character, however, with higher and lower than expected fluorescence intensities for mixtures of low and high primary amine concentration respectively. Further there are systematic differences in the labelling efficiencies of glycine and lysine, with trends visible for individual proteins within these bounds.

Figure 23C:
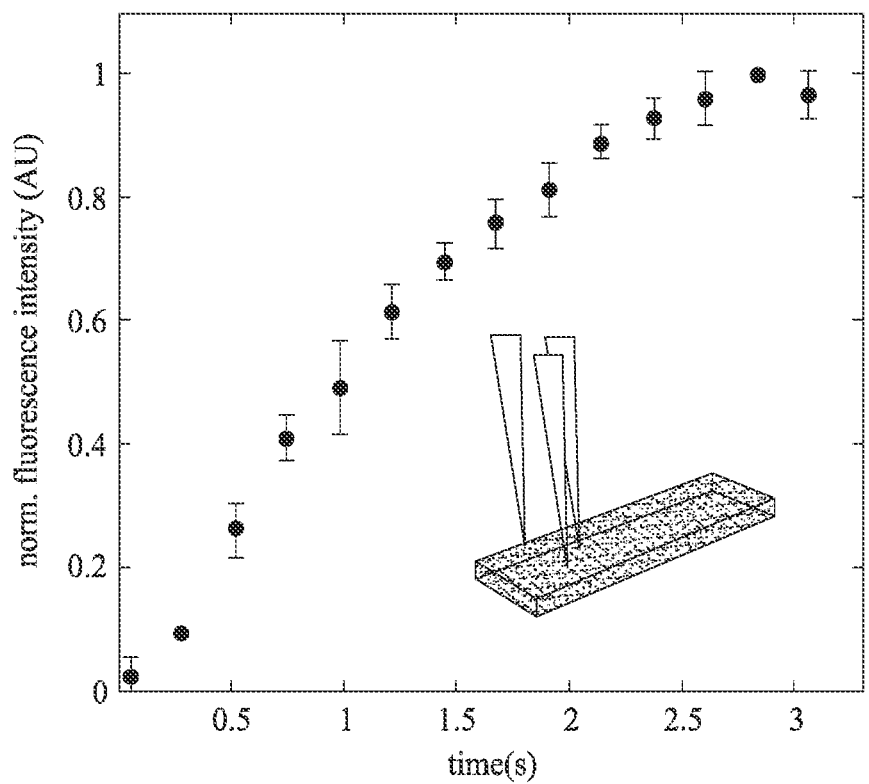
FIG. 23C shows the increased in normalised fluorescence intensity (AU) over time (s) for the BSA protein treated with the OPA labelling mixture at time 0.

Due to the low chemical stability reported for OPA-modified amines, it was hypothesized that these effects could be partially kinetic in origin. The time required for the generation of maximum fluorescence intensity was measured within a microfluidic mixing device, as shown in FIG. 23C, and observed that the labelling reaction reaches completion within 3 s. At later time points, fluorescence intensity generally decreases in a complex substrate and concentration dependent manner.

Due to the reported lack of chemical stability of the substituted isoindole formed in the fluorescence-generating OPA-labelling reaction, we investigated in detail the kinetics of the formation and degradation of the fluorescent species was studied.

Figure 23D:
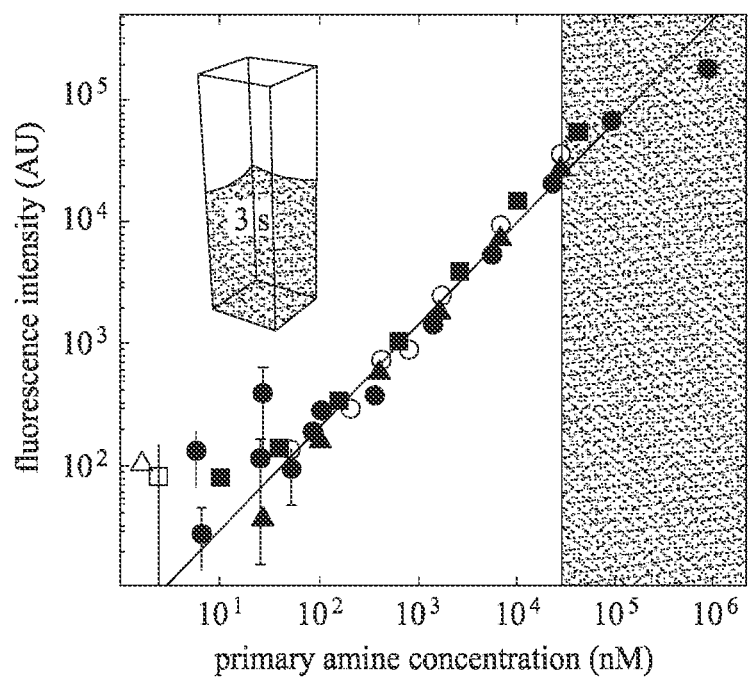
FIG. 23D shows the change in recorded fluorescence intensity (AU) with change in primary amine concentration for the proteins 3 s after they are exposed to the OPA labelling mixture.
Figure 23E:
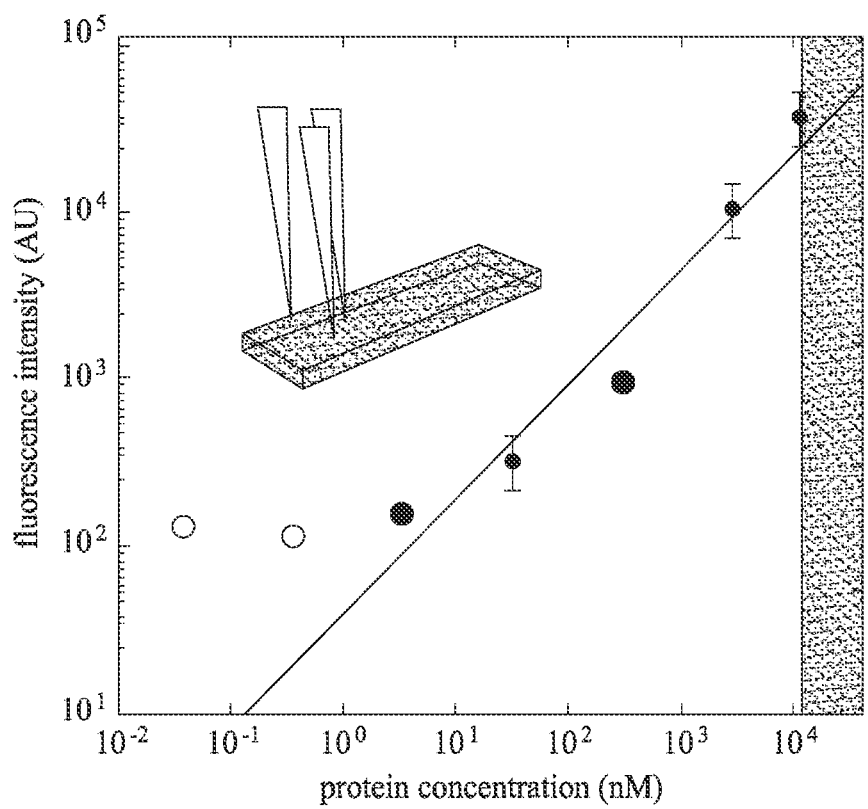

An analogous quantitative labelling assay was constructed at the 3 s time point, aiming to measure the fluorescence intensity before degradation mechanisms have had a significant effect (see FIG. 23D). Crucially, when fluorescence intensity is measured rapidly after reaction completion, sequence dependent variation collapses, and linearity extends over a primary amine concentration range covering four orders of magnitude, enabling the measurement of sub-nM protein concentrations. For reference, the range of concentrations routinely accessible through bulk absorption measurements is highlighted with a grey rectangle. Given the low path lengths characteristic of microfluidic systems, this detection limit was verified in the devices for use in the invention, which incorporate a 3 s reaction loop.

It was noted that the concentration of BSA could be determined quantitatively from fluorescence intensity for values between 3.75 nM and 15 uM. Given that the volume of the portion of the detection region in which fluorescence intensity is quantified in the microfluidic device is only 2.25 nL, this result reveals that less than 9 attomol BSA can be quantified on a flow device.

Figure 18:
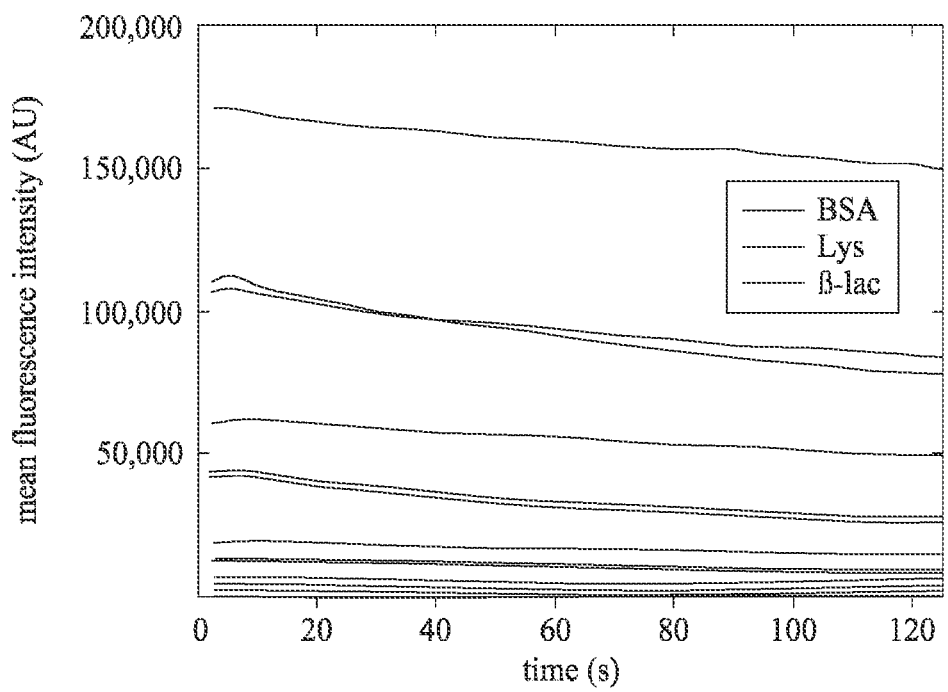
FIG. 18 shows the change in recorded fluorescence intensity (AU) over time (s) for a range of protein samples at different protein concentrations. The proteins are BSA, Lys and β-Lac, and the proteins have been labelled with an OPA fluorescent labelling mixture, as described herein.

Varying concentrations of BSA, β-lac and lysozyme were mixed with the OPA-labelling mixture, and the mean fluorescence intensity (AU) was measured over time (s). The results are shown in FIG. 18. For each protein, the mean fluorescence intensity was seen to decrease over time, with a noticeable drop in mean fluorescence intensity over 60 s.

A slight decrease in fluorescence intensity with time is observed, likely due to the lack of chemical stability of the formed isoindole. Additionally for low protein concentrations, an increase in fluorescence intensity around 40-60 s is observed, perhaps due to competing pathways which can be operative under forcing conditions. As discussed in the present case, measuring fluorescence intensity promptly after the protein is reacted with a label minimizes these effects.

Figure 19:
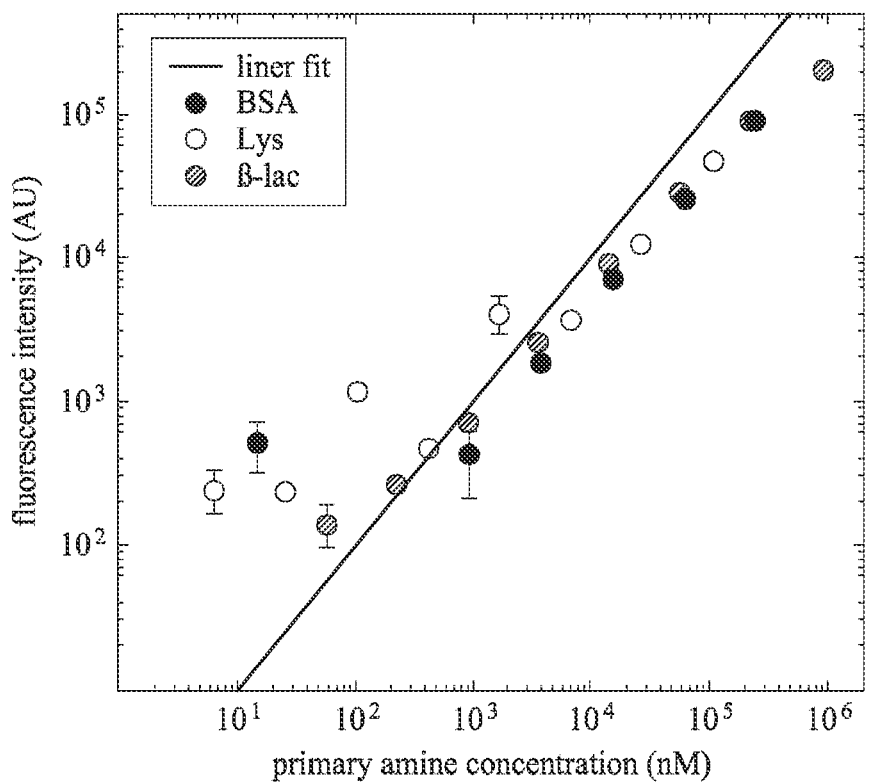
FIG. 19 shows the change in recorded fluorescence intensity (AU) with change in primary amine concentration for a range of protein samples that have been treated with an OPA fluorescent labelling mixture for 30 minutes. The proteins were BSA, Lys and β-Lac. The linear fit is shown.

The decrease in dynamic range with time was further elucidated by examining the change in the mean fluorescence intensity over a longer time frame. Thus the mean fluorescence intensity was measured after 30 minutes from the initiation of the labelling reaction. In this experiment, dye and protein solutions were allowed to sit at room temperature after mixing. The results are shown in FIG. 19, where the mean fluorescence intensity (AU) is shown as a function of the primary amine concentration (nM) within the solution. The double logarithm of the data were fitted to the equation $f(x)=0.99x$, revealing an $r^2$ of 0.67.

Deviations from linearity at low protein concentrations are more significant after longer reaction time. For fluorescence measurements at 30 minutes a primary amine concentration in excess of 1 µM is required for the accurate determination of protein concentration from fluorescence intensity. At primary amine concentrations below 1 µM and at very high amine concentrations, there is a deviation of the recorded mean fluorescence intensity from a linear relationship with the amine concentration. It is thought that this deviation results from competing reaction pathways, are here more significant.

From these results, the inventors now understand that is beneficial to measure fluorescence intensity soon after a component, such as a protein, is fluorescently labelled.

REFERENCES

All documents mentioned in this specification are incorporated herein by reference in their entirety.
Ahmad *Can J. Biochem. Cell Biol.* 63, 1058-1063 (1985)
Almgren et al. *Journal of Colloid and Interface Science* 202, 222-231 (1998)
Benson et al. *PNAS* 72, 619-622 (1975)
Biancalana et al. *Biochimica et Biophysica Acta* 1804, 1405-1412 (2010)
Brandts et al. *J. Am. Chem. Soc.* 89, 4826-4838 (1967)
Brody et al. *Sensors and Actuators A: Physical*, 58(1):13-18, 1997
Cheng et al. *Lab on a Chip* 11, 2316-2318 (2011)
Cohen et al. *Journal of Molecular Biology* 421, 160-171 (2012)
Flockhart et al. *Journal of Colloid Science* 12, 557-565 (1957)
Garcia Alvarez-Coque et al. *Anal Biochem* 178, 1-7 (1989)
GB 1320127.2
Ge et al. *J. Biomater. Sci. Polym. Ed.* 9, 131-150 (1998)
Hatch et al. *Nature Biotechnology*, 19(5):461-465, 2001
Hellstrand et al. *ACS Chemical Neuroscience* 1, 13-18 (2010)
Herling, T. W. et al. *Applied Physics Letters* 102, 184102-4 (2013)
Hirota et al. *Protein Science* 6, 416-421 (1997)
Ivanova et al. *PNAS* (2009), 106 (45), 18990-18995
Jacobs et al. *Analytical Biochemistry* 1986, 156, 334
Jacobson et al. *Anal. Chem.* 1994, 66, 4127
Jacobson et al. *Anal. Chem.* 1994, 66, 3472
Jimenez et al. *PNAS* 99, 9196-9201 (2002)
Kamholz et al. *Biophysical Journal* 80(4):1967-1972, 2001
Kang et al. *Lab on a Chip* 8, 1713-178 (2008))
Kim, P. et al. *Biochip Journal* 2, 1-11 (2008)
Knowles et al. *Science* 326, 1533-1537 (2009)
Kohlheyer et al. *Lab on a Chip* 6, 374-380 (2006)
Lauga et al. URL http://arxiv.org/abs/cond-mat/0501557
LeVine et al. *Protein Science* 2, 404-410 (1993)
Lee et al. *Lab on a Chip* 9, 479-482 (2009)
Liu et al. *Anal. Chem.* 2000, 72, 4608
Mok et al. *Methods* 54, 67-75 (2011)
Monahan et al. *Analytical Chemistry* 73, 3193-3197 (2001)
Nakamura et al. *Analytical Letters* 1982, 15, 1393-1410

Nettleton, E. J. et al. *Biophysical Journal* 79, 1053-1065 (2000)
Oguriet et al. *Journal of Chromatography A* 787, 253-260 (1997)
Otzen *Biochim. Biophys. Acta.* 1814, 562-591 (2011)
Otzen *Biophys. J.* 83, 2219-2230 (2002)
PCT/GB2013/052757 (WO 2014/064438)
Powers et al. *Biopolymers* 33, 92-932 (1993)
Rida et al. *Analytical Chemistry* 76, 6239-6246 (2004)
Roth et al. *Analytical Chemistry* 43, 880{882 (1971)
Roth et al. *Journal of Chromatography* 83, 353-356, (1973)
Saito et al. *Analytical Chemistry* 1994, 66, 134-138
Schuck *Anal. Biochem.* 320, 104-124 (2003)
Squires et al. *Reviews of Modern Physics* 77, 977-1026 (2005)
Sternson et al. *Anal. Biochem.* 144, 233-246 (1985)
Stone et al. *Annual Review of Fluid Mechanics* 36, 381-411 (2004)
Tan et al. *Biomicrofluidics* 4, 032204 (2010)
Turgeon et al. *Micro free-flow electrophoresis: theory and applications* 394, 187-198 (2009).
URL http://dx.doi.org/10.1007/s00216-009-2656-5
US 2002/0186263
US 2006/0263903
US 2010/0032349
US 2011/264380
US 2012/0135507
Walsh et al. *FEBS Journal* 276, 1266-1281 (2009)
Waugh *J. Am. Chem. Soc.* 68, 247-250 (1946)
Wetter et al. *Journal of Biological Chemistry* 192, 237-242 (1951)
Whitesides *Nature* 442, 368-373 (2006)
Whittingham et al. *Journal of Molecular Biology* 318, 479-490 (2002)
Wong et al. *J. Am. Chem. Soc.* 107, 6421-6422 (1985)
Yoshimura et al. *Anal. Biochem.* 164, 132-137 (1987)
Zawieja et al. *Analytical Biochemistry* 142, 182-188 (1984)

The invention claimed is:

1. A method of analysing a component, the method comprising the steps of:
   providing a first fluid flow comprising the component;
   providing a second fluid flow comprising a buffer or water;
   providing a distribution of the component across the first and second fluid flows which are in contact;
   diverting part of the first and second fluid flows and analysing the component in the diverted part of the fluid flows to obtain a first analytical signal indicative of at least one property of the component; and
      providing a first diverted fluid flow comprising the component;
      providing a second diverted fluid flow comprising the component;
      providing a distribution of the component across the first and second diverted fluid flows which are in contact;
      diverting part of the first and second fluid diverted flows and analysing the component in the diverted part of the diverted fluid flows to obtain a second analytical signal indicative of at least one property of the components;
      comparing the first and second analytical signals.

2. The method according to claim 1, wherein the steps leading to the second analytical signal are performed before the steps leading to the first analytical signal.

3. A method of analysing a component, the method comprising the steps of:
   providing a first fluid flow comprising the component;
   analysing the component in the first fluid to obtain an analytical signal indicative of at least one property of the component;
   providing a second fluid flow comprising a buffer or water;
   providing a distribution of the component across the first and second fluid flows;
   diverting part of the first and second fluid flows; and
   analysing the component in the diverted part of the fluid flows to obtain an analytical signal indicative of at least one property of the component; and
      comparing the analytical signal from the component in the diverted part with the analytical signal from the component in the first fluid.

4. The method according to claim 1, wherein the comparison of the analytical signals provides a ratio between the component in the diverted part and the first fluid.

5. The method according to claim 4, wherein the ratio is used to calculate the property of the component on which the lateral distribution is created.

6. The method according to claim 3, wherein the analysis of the component in the first fluid occurs after the diversion step.

7. The method according to claim 1, wherein the distribution is created by diffusion and the property of the component relates to the mass of the component.

8. The method according to claim 1, wherein the distribution is created by electrophoresis and the property of the component is an electrical property of the component.

9. The method according to claim 1, wherein the component is a protein.

10. The method according to claim 1, wherein the component is in its native state.

11. The method according to claim 1, wherein the method further comprises the step of labelling the component in the diverted part of the fluid flow.

12. The method according to claim 3, wherein the method further comprises the step of labelling the component in the first fluid.

13. A flow apparatus for detecting a component in a mixture, the apparatus comprising:
   a separation channel;
   a first inlet configured to introduce a first fluid comprising a first component into the separation channel;
   a second inlet configured to introduce a second fluid comprising a second component into the separation channel;
   wherein the separation channel is configured to permit lateral movement of the first and second components between the first and second fluids which are in contact in the separation channel;
   a downstream flow separator in fluid communication with the separation channel, wherein the flow separator is configured to divert a part of the first fluid, a part of the second fluid, or parts of the first fluid and the second fluid, from the separation channel, and
   a detection zone comprising:
   a detection channel provided downstream of and in fluid communication with the flow separator and configured to receive one or more of diverted flows from the flow separator; and
   a label channel configured to label each of the first and/or second components in one or more of the diverted flows from the flow separator; and an observation zone configured to record an analytical signal indicative of the quantity and/or the properties of each of the first and/or second components in one or more of the diverted parts.

14. The flow apparatus according to claim 13, wherein the first and second components are the same.

15. The flow apparatus according to claim 13, wherein the first and second components are different components.

16. The flow apparatus according to claim 13, wherein the separation channel permits lateral movement by diffusion and the observation zone is configured to record an analytical signal indicative of the mass of each of the first and/or second components in one of the diverted parts.

17. The flow apparatus according to claim 13, further comprising electrodes alongside the separation channel for deflecting charged components across the channel and the observation zone is configured to record an analytical signal indicative of the electrical properties of each of the first and/or second components in one of the diverted parts.

18. The flow apparatus according to claim 13, further comprising a waste channel at the downstream end of the observation zone.

19. The flow apparatus according claim 18, wherein the waste channel is at the downstream end of the separation channel.

* * * * *